US008058242B2

(12) United States Patent
Alewood et al.

(10) Patent No.: US 8,058,242 B2
(45) Date of Patent: Nov. 15, 2011

(54) CHIMERIC PROTEINS WITH NATRIURETIC ACTIVITY

(75) Inventors: Paul Alewood, Pullenvale (AU); Geoffrey A. Head, Camberwell (AU); Bryan Fry, Kalorama (AU)

(73) Assignees: The University of Queensland, St. Lucia, Queensland (AU); Baker Heart Research Institute, Prahran, Victoria (AU)

( * ) Notice: Subject to any disclaimer, the term of this patent is extended or adjusted under 35 U.S.C. 154(b) by 0 days.

(21) Appl. No.: 11/623,233

(22) Filed: Jan. 15, 2007

(65) Prior Publication Data

US 2008/0153747 A1 Jun. 26, 2008

Related U.S. Application Data

(63) Continuation-in-part of application No. PCT/AU2005/001047, filed on Jul. 15, 2005.

(60) Provisional application No. 60/588,243, filed on Jul. 15, 2004.

(51) Int. Cl.
*A61K 38/22* (2006.01)
*A61K 38/12* (2006.01)
*C12P 21/04* (2006.01)
*A61K 38/16* (2006.01)
*C07K 14/00* (2006.01)

(52) U.S. Cl. ............... 514/12.4; 435/69.7; 514/21.3; 530/317; 530/323

(58) Field of Classification Search .................. None
See application file for complete search history.

(56) References Cited

U.S. PATENT DOCUMENTS

| 4,339,440 A * | 7/1982 | Bajusz et al. ............ 514/18 |
| 4,824,937 A * | 4/1989 | Deghenghi et al. ...... 530/326 |
| 5,846,932 A | 12/1998 | Lowe et al. |
| 6,028,055 A | 2/2000 | Lowe et al. |
| 6,407,211 B1 | 6/2002 | Burnett et al. |
| 6,818,619 B2 | 11/2004 | Burnett et al. |
| 7,384,917 B2 | 6/2008 | Burnett et al. |
| 2004/0116657 A1 * | 6/2004 | Flatt et al. ................ 530/333 |

FOREIGN PATENT DOCUMENTS

| EP | 0911034 A1 | 4/1999 |
| WO | WO 88/03537 A1 | 5/1988 |
| WO | WO 89/09611 A1 | 10/1989 |
| WO | WO 90/00561 A1 | 1/1990 |
| WO | WO 95/28952 A1 | 11/1995 |
| WO | WO 98/45329 A1 | 10/1998 |
| WO | WO 00/71576 A2 | 11/2000 |
| WO | WO 01/44284 A2 | 6/2001 |
| WO | WO 02/074234 A2 | 9/2002 |
| WO | WO 03/079979 A2 | 10/2003 |
| WO | WO 03/081246 A1 | 10/2003 |
| WO | WO 2004/011498 A2 | 2/2004 |
| WO | WO 2004/047871 A2 | 6/2004 |
| WO | WO 2005/116655 A2 | 12/2005 |

OTHER PUBLICATIONS

Stadtman T, Selenocysteine, Annu. Rev. Biochem. 65, 83-100, 1996.*
Koide et al., Syntheses and Biological Activities of Selenium Analogs of alpha-Rat Atrial Natriuretic Peptide, Chem. Pharm. Bull. 41, 1596-1600, 1993.*
Amininasab, M. et al. 2004 "Functional and structural characterization of a novel member of the natriuretic family of peptides from the venom of *Pseudocerastes persicus*" *FEBS Letters* 557:104-108.
Barbouche, R. et al. 1996 "Novel anti-platelet aggregation polypeptides from *Vipera lebetina* venom: isolation and characterization" *FEBS Letters* 392:6-10.
Lisy, O. et al. 1999 "Renal actions of synthetic Dendroaspis natriuretic peptide" *Kidney International* 56:502-508.
PubMed Protein ID P83231 Venom natriuretic peptide OxsSNPc, available online Sep. 15, 2003.
PubMed Protein ID P83230 Venom natriuretic peptide OxsSNPc, available online Sep. 15, 2003.
PubMed Protein ID P83225 Venom natriuretic peptide OxsSNPc, available online Sep. 15, 2003.
PubMed Protein ID P83226 Venom natriuretic peptide OxsSNPc, available online Sep. 15, 2003.
PubMed Protein ID P83224 Venom natriuretic peptide OxsSNPc, available online Sep. 15, 2003.
PubMed Protein ID P83228 Venom natriuretic peptide OxsSNPc, available online Sep. 15, 2003.
PubMed Protein ID P83229 Venom natriuretic peptide OxsSNPc, available online Sep. 15, 2003.
PubMed Protein ID P83227 Venom natriuretic peptide OxsSNPc, available online Sep. 15, 2003.
PubMed Protein ID P22642 Ventricular natriuretic peptide, available online Aug. 1, 1991.
PubMed Protein ID 046541 Brain natriuretic peptide precursor, available online Jun. 15, 2002.
PubMed Protein ID P07634 Brain natriuretic peptide precursor, available online Nov. 1, 1991.
PubMed Protein ID P16859 Brain natriuretic peptide precursor, available online Nov. 1, 1990.
PubMed Protein ID P13204 Brain natriuretic peptide precursor, available online Dec. 1, 1992. PubMed Protein ID P56283 C-type natriuretic peptide precursor, available online Feb. 1, 1998.
PubMed Protein ID P55207 C-type natriuretic peptide precursor, available online Oct. 1, 1996.
PubMed Protein ID P18104 C-type natriuretic peptide precursor, available online Mar. 1, 1992.
PubMed Protein ID Q61839 C-type natriuretic peptide precursor, available online Nov. 1, 1997.
PubMed Protein ID P23582 C-type natriuretic peptide precursor, available online Dec. 1, 1992.
PubMed Protein ID P55206 C-type natriuretic peptide precursor, available online Oct. 1, 1996.
PubMed Protein ID P18145 C-type natriuretic peptide precursor, available online Feb. 1, 1991.
PubMed Protein ID P16860 C-type natriuretic peptide precursor, available online Feb. 1, 1991.
Fry, B.G. et al. 2005 "Novel natriuretic peptides from the venom of the inland taipan (*Oxyuranus microlepidotus*): isolation, chemical and biological characterisation" *Biochemical and Biophysical Research Communications* 327:1011-1015.
Luis Bolaños Cea, "Natriuretic Peptide Family: New Aspects", *Curr. Med. Chem.* 2005, 3: 87-98.

* cited by examiner

*Primary Examiner* — Elly-Gerald Stoica
(74) *Attorney, Agent, or Firm* — Knobbe, Marten, Olson & Bear, LLP

(57) ABSTRACT

The present invention discloses proteinaceous compounds that comprise at least a biologically active portion of a taipan natriuretic peptide (TNP) or a variant or derivative thereof. The invention also relates to the use of these compounds in methods for stimulating vasodilation, natriuresis, diuresis, renin-suppression, bactericidal activity, weight-loss or bone growth in a mammalian host. In specific embodiments, the compounds are useful in the treatment of congestive heart failure.

26 Claims, 11 Drawing Sheets

```
Ring position              12345678901234567
ANP mouse              SLRRSSCFGGRIDRIGAQSGLGCNSFRYRR         SEQ ID NO: 108
ANP rat                SLRRSSCFGGRIDRIGAQSGLGCNSFRYRR         SEQ ID NO: 109
ANP human              SLRRSSCFGGRMDRIGAQSGLGCNSFRY           SEQ ID NO: 82
BNP human              SPKMVQGSGCFGRKMDRISSSSGLGCKVLRRH       SEQ ID NO: 63
BNP rat            IQERLRNSKMAHSSSCFGQKIDRIGAVSRLGCDGLRLF     SEQ ID NO: 110
DNP                    EVKYDPCFGHKIDRINHVSNLGCPSLRDPRPNAPSTSA SEQ ID NO: 65
TNPa                   SDSKIGDCCFGLPLDHIGSVSGLGCNRPVQNRPKK    SEQ ID NO: 68
TNPb                   SDPKIGDCCFGLPLDHIGSVSGLGCNRPVQNRPKK    SEQ ID NO: 69
TNPc                   SDSKIGNCCFGFPLDRIGSVSGLGCNRIMQNPPKKFSGE SEQ ID NO: 70
VNP                    AKTAKSFNSCFGTRMDRIGSWSGLGCNSLKNGTKKKIFGN SEQ ID NO: 193
PNP                GENEPPKKKAPDCFGHKIDRIGSHSGLGCNKFKPGH       SEQ ID NO: 87
Lebetin 2          GDNKPPKKGPPNCCFGHKIDRIGSHSGLGCNKVDDNKG     SEQ ID NO: 86
```

FIGURE 2

6a
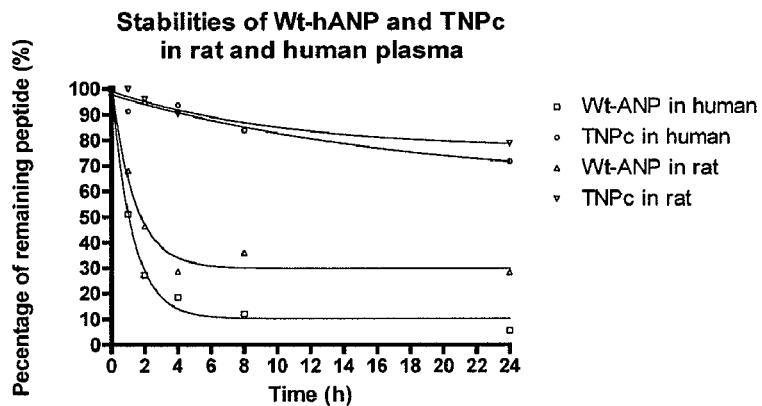
6b
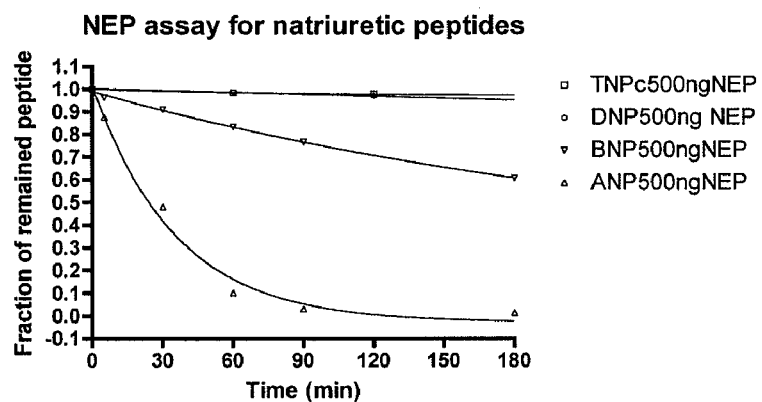
6c
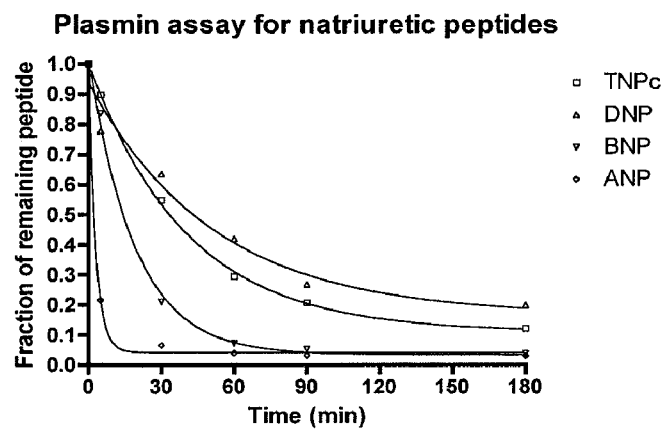
FIGURE 6

SEQUENCE LISTING

```
<160> NUMBER OF SEQ ID NOS: 204

<210> SEQ ID NO 1
<211> LENGTH: 10
<212> TYPE: PRT
<213> ORGANISM: Oxyuranus microlepidotus

<400> SEQUENCE: 1

Asn Arg Ile Met Gln Asn Pro Pro Lys Lys
1               5                   10

<210> SEQ ID NO 2
<211> LENGTH: 11
<212> TYPE: PRT
<213> ORGANISM: Oxyuranus microlepidotus

<400> SEQUENCE: 2

Asn Arg Ile Met Gln Asn Pro Pro Lys Lys Phe
1               5                   10

<210> SEQ ID NO 3
<211> LENGTH: 12
<212> TYPE: PRT
<213> ORGANISM: Oxyuranus microlepidotus

<400> SEQUENCE: 3

Asn Arg Ile Met Gln Asn Pro Pro Lys Lys Phe Ser
1               5                   10
```

<210> SEQ ID NO 4
<211> LENGTH: 13
<212> TYPE: PRT
<213> ORGANISM: Oxyuranus microlepidotus

<400> SEQUENCE: 4

Asn Arg Ile Met Gln Asn Pro Pro Lys Lys Phe Ser Gly
1               5                   10

<210> SEQ ID NO 5
<211> LENGTH: 14
<212> TYPE: PRT
<213> ORGANISM: Oxyuranus microlepidotus

<400> SEQUENCE: 5

Asn Arg Ile Met Gln Asn Pro Pro Lys Lys Phe Ser Gly Glu
1               5                   10

<210> SEQ ID NO 6
<211> LENGTH: 17
<212> TYPE: PRT
<213> ORGANISM: Oxyuranus microlepidotus

<400> SEQUENCE: 6

Cys Phe Gly Phe Pro Leu Asp Arg Ile Gly Ser Val Ser Gly Leu Gly
1               5                   10                  15

Cys

<210> SEQ ID NO 7
<211> LENGTH: 8
<212> TYPE: PRT
<213> ORGANISM: Oxyuranus microlepidotus

<400> SEQUENCE: 7

Ser Asp Ser Lys Ile Gly Asn Gly
1               5

<210> SEQ ID NO 8
<211> LENGTH: 5
<212> TYPE: PRT
<213> ORGANISM: Artificial sequence
<220> FEATURE:
<223> OTHER INFORMATION: A portion of a natriuretic peptide

<400> SEQUENCE: 8

Asn Ser Phe Arg Tyr
1               5

<210> SEQ ID NO 9
<211> LENGTH: 7
<212> TYPE: PRT
<213> ORGANISM: Artificial sequence
<220> FEATURE:
<223> OTHER INFORMATION: A portion of a natriuretic peptide

<400> SEQUENCE: 9

Asn Ser Phe Arg Tyr Arg Arg
1               5

<210> SEQ ID NO 10
<211> LENGTH: 6
<212> TYPE: PRT
<213> ORGANISM: Artificial sequence
<220> FEATURE:
<223> OTHER INFORMATION: A portion of a natriuretic peptide

```
<400> SEQUENCE: 10

Lys Val Leu Arg Arg His
1               5

<210> SEQ ID NO 11
<211> LENGTH: 6
<212> TYPE: PRT
<213> ORGANISM: Artificial sequence
<220> FEATURE:
<223> OTHER INFORMATION: A portion of a natriuretic peptide

<400> SEQUENCE: 11

Asp Gly Leu Arg Leu Phe
1               5

<210> SEQ ID NO 12
<211> LENGTH: 15
<212> TYPE: PRT
<213> ORGANISM: Artificial sequence
<220> FEATURE:
<223> OTHER INFORMATION: A portion of a natriuretic peptide

<400> SEQUENCE: 12

Pro Ser Leu Arg Asp Pro Arg Pro Asn Ala Pro Ser Thr Ser Ala
1               5                   10                  15

<210> SEQ ID NO 13
<211> LENGTH: 8
<212> TYPE: PRT
<213> ORGANISM: Artificial sequence
<220> FEATURE:
<223> OTHER INFORMATION: A portion of a natriuretic peptide

<400> SEQUENCE: 13

Asn Lys Val Asp Asp Asn Lys Gly
1               5

<210> SEQ ID NO 14
<211> LENGTH: 4
<212> TYPE: PRT
<213> ORGANISM: Artificial sequence
<220> FEATURE:
<223> OTHER INFORMATION: A portion of a natriuretic peptide

<400> SEQUENCE: 14

Phe Ser Gly Glu
1

<210> SEQ ID NO 15
<211> LENGTH: 10
<212> TYPE: PRT
<213> ORGANISM: Artificial sequence
<220> FEATURE:
<223> OTHER INFORMATION: A portion of a natriuretic peptide

<400> SEQUENCE: 15

Asn Arg Ile Val Gln Asn Arg Pro Lys Lys
1               5                   10

<210> SEQ ID NO 16
<211> LENGTH: 10
<212> TYPE: PRT
<213> ORGANISM: Artificial sequence
<220> FEATURE:
<223> OTHER INFORMATION: A portion of a natriuretic peptide

<400> SEQUENCE: 16
```

Asn Arg Leu Val Gln Asn Arg Pro Lys Lys
1               5                   10

<210> SEQ ID NO 17
<211> LENGTH: 14
<212> TYPE: PRT
<213> ORGANISM: Artificial sequence
<220> FEATURE:
<223> OTHER INFORMATION: A portion of a natriuretic peptide

<400> SEQUENCE: 17

Asn Arg Ile Met Gln Asn Pro Pro Lys Lys Phe Ser Gly Glu
1               5                   10

<210> SEQ ID NO 18
<211> LENGTH: 14
<212> TYPE: PRT
<213> ORGANISM: Artificial sequence
<220> FEATURE:
<223> OTHER INFORMATION: A portion of a natriuretic peptide

<400> SEQUENCE: 18

Asn Arg Phe Met Gln Asn Arg Pro Lys Lys Phe Ser Gly Glu
1               5                   10

<210> SEQ ID NO 19
<211> LENGTH: 14
<212> TYPE: PRT
<213> ORGANISM: Artificial sequence
<220> FEATURE:
<223> OTHER INFORMATION: A portion of a natriuretic peptide

<400> SEQUENCE: 19

Asn Arg Ile Leu Gln Asn Pro Pro Lys Lys Phe Ser Gly Glu
1               5                   10

<210> SEQ ID NO 20
<211> LENGTH: 14
<212> TYPE: PRT
<213> ORGANISM: Artificial sequence
<220> FEATURE:
<223> OTHER INFORMATION: A portion of a natriuretic peptide

<400> SEQUENCE: 20

Asn Arg Pro Met Asn Asn Pro Pro Lys Lys Phe Ser Gly Glu
1               5                   10

<210> SEQ ID NO 21
<211> LENGTH: 14
<212> TYPE: PRT
<213> ORGANISM: Artificial sequence
<220> FEATURE:
<223> OTHER INFORMATION: A portion of a natriuretic peptide

<400> SEQUENCE: 21

Asn Arg Ile Val Gln Asn Pro Pro Lys Lys Phe Ser Gly Glu
1               5                   10

<210> SEQ ID NO 22
<211> LENGTH: 14
<212> TYPE: PRT
<213> ORGANISM: Artificial sequence
<220> FEATURE:
<223> OTHER INFORMATION: A portion of a natriuretic peptide

<400> SEQUENCE: 22

Asn Arg Ile Met Gln Asn Arg Pro Lys Lys Phe Ser Gly Glu

<210> SEQ ID NO 23
<211> LENGTH: 14
<212> TYPE: PRT
<213> ORGANISM: Artificial sequence
<220> FEATURE:
<223> OTHER INFORMATION: A portion of a natriuretic peptide

<400> SEQUENCE: 23

Lys Arg Ile Met Gln Asn Pro Pro Lys Lys Phe Ser Gly Glu
1               5                   10

<210> SEQ ID NO 24
<211> LENGTH: 14
<212> TYPE: PRT
<213> ORGANISM: Artificial sequence
<220> FEATURE:
<223> OTHER INFORMATION: A portion of a natriuretic peptide

<400> SEQUENCE: 24

Asn Ser Ile Met Gln Asn Pro Pro Lys Lys Phe Ser Gly Glu
1               5                   10

<210> SEQ ID NO 25
<211> LENGTH: 14
<212> TYPE: PRT
<213> ORGANISM: Artificial sequence
<220> FEATURE:
<223> OTHER INFORMATION: A portion of a natriuretic peptide

<400> SEQUENCE: 25

Asn Arg Leu Met Gln Asn Pro Pro Lys Lys Phe Ser Gly Glu
1               5                   10

<210> SEQ ID NO 26
<211> LENGTH: 14
<212> TYPE: PRT
<213> ORGANISM: Artificial sequence
<220> FEATURE:
<223> OTHER INFORMATION: A portion of a natriuretic peptide

<400> SEQUENCE: 26

Asn Arg Phe Met Gln Asn Pro Pro Lys Lys Phe Ser Gly Glu
1               5                   10

<210> SEQ ID NO 27
<211> LENGTH: 14
<212> TYPE: PRT
<213> ORGANISM: Artificial sequence
<220> FEATURE:
<223> OTHER INFORMATION: A portion of a natriuretic peptide

<400> SEQUENCE: 27

Lys Arg Ile Val Gln Asn Pro Pro Lys Lys Phe Ser Gly Glu
1               5                   10

<210> SEQ ID NO 28
<211> LENGTH: 14
<212> TYPE: PRT
<213> ORGANISM: Artificial sequence
<220> FEATURE:
<223> OTHER INFORMATION: A portion of a natriuretic peptide

<400> SEQUENCE: 28

Asn Arg Ile Met Gln Gln Pro Pro Lys Lys Phe Ser Gly Glu
1               5                   10

<210> SEQ ID NO 29
<211> LENGTH: 14
<212> TYPE: PRT
<213> ORGANISM: Artificial sequence
<220> FEATURE:
<223> OTHER INFORMATION: A portion of a natriuretic peptide

<400> SEQUENCE: 29

Asn Arg Ile Asn Gln Asn Pro Pro Lys Lys Phe Ser Gly Glu
1               5                   10

<210> SEQ ID NO 30
<211> LENGTH: 14
<212> TYPE: PRT
<213> ORGANISM: Artificial sequence
<220> FEATURE:
<223> OTHER INFORMATION: A portion of a natriuretic peptide

<400> SEQUENCE: 30

Asn Arg Ile Met Gln Ala Pro Pro Lys Lys Phe Ser Gly Glu
1               5                   10

<210> SEQ ID NO 31
<211> LENGTH: 14
<212> TYPE: PRT
<213> ORGANISM: Artificial sequence
<220> FEATURE:
<223> OTHER INFORMATION: A portion of a natriuretic peptide

<400> SEQUENCE: 31

Asn Arg Leu Met Gln Gln Pro Pro Lys Lys Phe Ser Gly Glu
1               5                   10

<210> SEQ ID NO 32
<211> LENGTH: 14
<212> TYPE: PRT
<213> ORGANISM: Artificial sequence
<220> FEATURE:
<223> OTHER INFORMATION: A portion of a natriuretic peptide
<220> FEATURE:
<221> NAME/KEY: MISC_FEATURE
<222> LOCATION: (7)..(7)
<223> OTHER INFORMATION: Xaa=hydroxyproline

<400> SEQUENCE: 32

Asn Arg Ile Met Gln Ala Xaa Pro Lys Lys Phe Ser Gly Glu
1               5                   10

<210> SEQ ID NO 33
<211> LENGTH: 14
<212> TYPE: PRT
<213> ORGANISM: Artificial sequence
<220> FEATURE:
<223> OTHER INFORMATION: A portion of a natriuretic peptide
<220> FEATURE:
<221> NAME/KEY: MISC_FEATURE
<222> LOCATION: (7)..(7)
<223> OTHER INFORMATION: Xaa=hydroxyproline

<400> SEQUENCE: 33

Asn Arg Ile Met Gln Gln Xaa Pro Lys Lys Phe Ser Gly Glu
1               5                   10

<210> SEQ ID NO 34
<211> LENGTH: 14
<212> TYPE: PRT
<213> ORGANISM: Artificial sequence
<220> FEATURE:
<223> OTHER INFORMATION: A portion of a natriuretic peptide

<400> SEQUENCE: 34

Asn Arg Ile Met Gln Asn Pro Pro Lys Lys Phe Ser Gly Glu
1               5                   10

<210> SEQ ID NO 35
<211> LENGTH: 14
<212> TYPE: PRT
<213> ORGANISM: Artificial sequence
<220> FEATURE:
<223> OTHER INFORMATION: A portion of a natriuretic peptide

<400> SEQUENCE: 35

Asn Arg Ile Asn Gln Ala Pro Pro Lys Lys Phe Ser Gly Glu
1               5                   10

<210> SEQ ID NO 36
<211> LENGTH: 14
<212> TYPE: PRT
<213> ORGANISM: Artificial sequence
<220> FEATURE:
<223> OTHER INFORMATION: A portion of a natriuretic peptide

<400> SEQUENCE: 36

Asn Arg Val Asn Gln Ala Pro Pro Lys Lys Phe Ser Gly Glu
1               5                   10

<210> SEQ ID NO 37
<211> LENGTH: 14
<212> TYPE: PRT
<213> ORGANISM: Artificial sequence
<220> FEATURE:
<223> OTHER INFORMATION: A portion of a natriuretic peptide

<400> SEQUENCE: 37

Asn Arg Ile Met Gln Asn Arg Pro Lys Lys Phe Ser Gly Glu
1               5                   10

<210> SEQ ID NO 38
<211> LENGTH: 14
<212> TYPE: PRT
<213> ORGANISM: Artificial sequence
<220> FEATURE:
<223> OTHER INFORMATION: A portion of a natriuretic peptide

<400> SEQUENCE: 38

Asn Arg Val Met Gln Asn Pro Pro Lys Lys Phe Ser Gly Glu
1               5                   10

<210> SEQ ID NO 39
<211> LENGTH: 14
<212> TYPE: PRT
<213> ORGANISM: Artificial sequence
<220> FEATURE:
<223> OTHER INFORMATION: A portion of a natriuretic peptide

<400> SEQUENCE: 39

Asn Arg Ile Met Gln Gln Arg Pro Lys Lys Phe Ser Gly Glu
1               5                   10

<210> SEQ ID NO 40
<211> LENGTH: 14
<212> TYPE: PRT
<213> ORGANISM: Artificial sequence
<220> FEATURE:
<223> OTHER INFORMATION: A portion of a natriuretic peptide

<400> SEQUENCE: 40

```
Lys Arg Ile Met Gln Asn Pro Pro Lys Phe Ser Gly Glu
1               5                   10
```

<210> SEQ ID NO 41
<211> LENGTH: 14
<212> TYPE: PRT
<213> ORGANISM: Artificial sequence
<220> FEATURE:
<223> OTHER INFORMATION: A portion of a natriuretic peptide

<400> SEQUENCE: 41

```
Asn Arg Ile Met Arg Gln Pro Pro Lys Lys Phe Ser Gly Glu
1               5                   10
```

<210> SEQ ID NO 42
<211> LENGTH: 14
<212> TYPE: PRT
<213> ORGANISM: Artificial sequence
<220> FEATURE:
<223> OTHER INFORMATION: A portion of a natriuretic peptide

<400> SEQUENCE: 42

```
Asn Arg Val Met Arg Gln Pro Pro Lys Lys Phe Ser Gly Glu
1               5                   10
```

<210> SEQ ID NO 43
<211> LENGTH: 14
<212> TYPE: PRT
<213> ORGANISM: Artificial sequence
<220> FEATURE:
<223> OTHER INFORMATION: A portion of a natriuretic peptide

<400> SEQUENCE: 43

```
Asn Arg Ile Met Gln Asn Pro Pro Lys Lys Phe Ser Thr Glu
1               5                   10
```

<210> SEQ ID NO 44
<211> LENGTH: 15
<212> TYPE: PRT
<213> ORGANISM: Artificial sequence
<220> FEATURE:
<223> OTHER INFORMATION: A portion of a natriuretic peptide

<400> SEQUENCE: 44

```
Pro Ser Leu Arg Asp Pro Arg Pro Asn Ala Pro Ser Thr Ser Ala
1               5                   10                  15
```

<210> SEQ ID NO 45
<211> LENGTH: 15
<212> TYPE: PRT
<213> ORGANISM: Artificial sequence
<220> FEATURE:
<223> OTHER INFORMATION: A portion of a natriuretic peptide

<400> SEQUENCE: 45

```
Pro Val Leu Arg Asp Pro Arg Pro Asn Ala Pro Ser Thr Ser Ala
1               5                   10                  15
```

<210> SEQ ID NO 46
<211> LENGTH: 14
<212> TYPE: PRT
<213> ORGANISM: Artificial sequence
<220> FEATURE:
<223> OTHER INFORMATION: A portion of a natriuretic peptide

<400> SEQUENCE: 46

```
Asn Arg Leu Val Gln Asn Pro Pro Lys Lys Phe Ser Gly Glu
```

-continued

<210> SEQ ID NO 47
<211> LENGTH: 14
<212> TYPE: PRT
<213> ORGANISM: Artificial sequence
<220> FEATURE:
<223> OTHER INFORMATION: A portion of a natriuretic peptide

<400> SEQUENCE: 47

Asn Arg Ile Met Gln Asn Arg Pro Lys Lys Phe Ser Gly Glu
1               5                   10

<210> SEQ ID NO 48
<211> LENGTH: 15
<212> TYPE: PRT
<213> ORGANISM: Artificial sequence
<220> FEATURE:
<223> OTHER INFORMATION: A portion of a natriuretic peptide

<400> SEQUENCE: 48

Pro Arg Leu Arg Asp Pro Arg Pro Asn Ala Pro Ser Thr Ser Ala
1               5                   10                  15

<210> SEQ ID NO 49
<211> LENGTH: 8
<212> TYPE: PRT
<213> ORGANISM: Artificial sequence
<220> FEATURE:
<223> OTHER INFORMATION: A portion of a natriuretic peptide

<400> SEQUENCE: 49

Ser Asp Pro Lys Ile Gly Asp Gly
1               5

<210> SEQ ID NO 50
<211> LENGTH: 8
<212> TYPE: PRT
<213> ORGANISM: Artificial sequence
<220> FEATURE:
<223> OTHER INFORMATION: A portion of a natriuretic peptide

<400> SEQUENCE: 50

Ser Asp Ser Lys Ile Gly Asp Gly
1               5

<210> SEQ ID NO 51
<211> LENGTH: 8
<212> TYPE: PRT
<213> ORGANISM: Artificial sequence
<220> FEATURE:
<223> OTHER INFORMATION: A portion of a natriuretic peptide

<400> SEQUENCE: 51

Ser Asp Ser Lys Ile Gly Asn Gly
1               5

<210> SEQ ID NO 52
<211> LENGTH: 8
<212> TYPE: PRT
<213> ORGANISM: Artificial sequence
<220> FEATURE:
<223> OTHER INFORMATION: A portion of a natriuretic peptide

<400> SEQUENCE: 52

Ser Asp Ser Lys Ile Gly Gln Gly
1               5

<210> SEQ ID NO 53
<211> LENGTH: 8
<212> TYPE: PRT
<213> ORGANISM: Artificial sequence
<220> FEATURE:
<223> OTHER INFORMATION: A portion of a natriuretic peptide

<400> SEQUENCE: 53

Ser Asp Ser Lys Ile Gly Ala Gly
1               5

<210> SEQ ID NO 54
<211> LENGTH: 8
<212> TYPE: PRT
<213> ORGANISM: Artificial sequence
<220> FEATURE:
<223> OTHER INFORMATION: A portion of a natriuretic peptide

<400> SEQUENCE: 54

Ser Asp Ser Lys Ile Gly Lys Gly
1               5

<210> SEQ ID NO 55
<211> LENGTH: 8
<212> TYPE: PRT
<213> ORGANISM: Artificial sequence
<220> FEATURE:
<223> OTHER INFORMATION: A portion of a natriuretic peptide

<400> SEQUENCE: 55

Ser Asp Ser Lys Ile Ser Lys Gly
1               5

<210> SEQ ID NO 56
<211> LENGTH: 8
<212> TYPE: PRT
<213> ORGANISM: Artificial sequence
<220> FEATURE:
<223> OTHER INFORMATION: A portion of a natriuretic peptide

<400> SEQUENCE: 56

Ser Asp Ser Lys Ile Gly Asn Gly
1               5

<210> SEQ ID NO 57
<211> LENGTH: 9
<212> TYPE: PRT
<213> ORGANISM: Artificial sequence
<220> FEATURE:
<223> OTHER INFORMATION: A portion of a natriuretic peptide

<400> SEQUENCE: 57

Glx Ser Asp Ser Lys Ile Gly Asn Gly
1               5

<210> SEQ ID NO 58
<211> LENGTH: 8
<212> TYPE: PRT
<213> ORGANISM: Artificial sequence
<220> FEATURE:
<223> OTHER INFORMATION: A portion of a natriuretic peptide

<400> SEQUENCE: 58

Ser Asp Ser Lys Ile Gly Ala Gly
1               5

<210> SEQ ID NO 59

```
<211> LENGTH: 9
<212> TYPE: PRT
<213> ORGANISM: Artificial sequence
<220> FEATURE:
<223> OTHER INFORMATION: A portion of a natriuretic peptide

<400> SEQUENCE: 59

Glx Ser Asp Ser Lys Ile Gly Ala Gly
1               5

<210> SEQ ID NO 60
<211> LENGTH: 9
<212> TYPE: PRT
<213> ORGANISM: Artificial sequence
<220> FEATURE:
<223> OTHER INFORMATION: A portion of a natriuretic peptide

<400> SEQUENCE: 60

Ser Pro Lys Met Val Gln Gly Ser Gly
1               5

<210> SEQ ID NO 61
<211> LENGTH: 9
<212> TYPE: PRT
<213> ORGANISM: Artificial sequence
<220> FEATURE:
<223> OTHER INFORMATION: A portion of a natriuretic peptide

<400> SEQUENCE: 61

Ser Pro Lys Met Val Gln Gly Ser Gly
1               5

<210> SEQ ID NO 62
<211> LENGTH: 8
<212> TYPE: PRT
<213> ORGANISM: Artificial sequence
<220> FEATURE:
<223> OTHER INFORMATION: A portion of a natriuretic peptide

<400> SEQUENCE: 62

Ser Asp Ser Lys Ile Gly Asn Gly
1               5

<210> SEQ ID NO 63
<211> LENGTH: 9
<212> TYPE: PRT
<213> ORGANISM: Artificial sequence
<220> FEATURE:
<223> OTHER INFORMATION: A portion of a natriuretic peptide

<400> SEQUENCE: 63

Ser Pro Lys Met Val Gln Gly Ser Gly
1               5

<210> SEQ ID NO 64
<211> LENGTH: 8
<212> TYPE: PRT
<213> ORGANISM: Artificial sequence
<220> FEATURE:
<223> OTHER INFORMATION: A portion of a natriuretic peptide

<400> SEQUENCE: 64

Ser Asp Ser Lys Ile Gly Asn Gly
1               5

<210> SEQ ID NO 65
<211> LENGTH: 8
<212> TYPE: PRT
```

```
<213> ORGANISM: Artificial sequence
<220> FEATURE:
<223> OTHER INFORMATION: A portion of a natriuretic peptide

<400> SEQUENCE: 65

Ser Asp Ser Lys Ile Gly Asn Gly
1               5

<210> SEQ ID NO 66
<211> LENGTH: 6
<212> TYPE: PRT
<213> ORGANISM: Artificial sequence
<220> FEATURE:
<223> OTHER INFORMATION: A portion of a natriuretic peptide

<400> SEQUENCE: 66

Ser Leu Arg Arg Ser Ser
1               5

<210> SEQ ID NO 67
<211> LENGTH: 8
<212> TYPE: PRT
<213> ORGANISM: Artificial sequence
<220> FEATURE:
<223> OTHER INFORMATION: A portion of a natriuretic peptide

<400> SEQUENCE: 67

Ser Asp Ser Lys Ile Gly Asn Gly
1               5

<210> SEQ ID NO 68
<211> LENGTH: 17
<212> TYPE: PRT
<213> ORGANISM: Artificial sequence
<220> FEATURE:
<223> OTHER INFORMATION: A portion of a natriuretic peptide

<400> SEQUENCE: 68

Cys Phe Gly Phe Pro Leu Asp Arg Ile Gly Ser Val Ser Gly Leu Gly
1               5                   10                  15

Cys

<210> SEQ ID NO 69
<211> LENGTH: 17
<212> TYPE: PRT
<213> ORGANISM: Artificial sequence
<220> FEATURE:
<223> OTHER INFORMATION: A portion of a natriuretic peptide

<400> SEQUENCE: 69

Cys Phe Gly Leu Pro Leu Asp Arg Ile Gly Ser Val Ser Gly Leu Gly
1               5                   10                  15

Cys

<210> SEQ ID NO 70
<211> LENGTH: 17
<212> TYPE: PRT
<213> ORGANISM: Artificial sequence
<220> FEATURE:
<223> OTHER INFORMATION: A portion of a natriuretic peptide

<400> SEQUENCE: 70

Cys Phe Gly Ile Pro Leu Asp Arg Ile Gly Ser Val Ser Gly Leu Gly
1               5                   10                  15

Cys
```

```
<210> SEQ ID NO 71
<211> LENGTH: 17
<212> TYPE: PRT
<213> ORGANISM: Artificial sequence
<220> FEATURE:
<223> OTHER INFORMATION: A portion of a natriuretic peptide

<400> SEQUENCE: 71

Cys Phe Gly His Pro Leu Asp Arg Ile Gly Ser Val Ser Gly Leu Gly
1               5                   10                  15

Cys

<210> SEQ ID NO 72
<211> LENGTH: 17
<212> TYPE: PRT
<213> ORGANISM: Artificial sequence
<220> FEATURE:
<223> OTHER INFORMATION: A portion of a natriuretic peptide

<400> SEQUENCE: 72

Cys Phe Gly Gln Pro Leu Asp Arg Ile Gly Ser Val Ser Gly Leu Gly
1               5                   10                  15

Cys

<210> SEQ ID NO 73
<211> LENGTH: 17
<212> TYPE: PRT
<213> ORGANISM: Artificial sequence
<220> FEATURE:
<223> OTHER INFORMATION: A portion of a natriuretic peptide

<400> SEQUENCE: 73

Cys Phe Gly Arg Pro Leu Asp Arg Ile Gly Ser Val Ser Gly Leu Gly
1               5                   10                  15

Cys

<210> SEQ ID NO 74
<211> LENGTH: 17
<212> TYPE: PRT
<213> ORGANISM: Artificial sequence
<220> FEATURE:
<223> OTHER INFORMATION: A portion of a natriuretic peptide

<400> SEQUENCE: 74

Cys Phe Gly Phe Lys Leu Asp Arg Ile Gly Ser Val Ser Gly Leu Gly
1               5                   10                  15

Cys

<210> SEQ ID NO 75
<211> LENGTH: 17
<212> TYPE: PRT
<213> ORGANISM: Artificial sequence
<220> FEATURE:
<223> OTHER INFORMATION: A portion of a natriuretic peptide

<400> SEQUENCE: 75

Cys Phe Gly Phe Arg Leu Asp Arg Ile Gly Ser Val Ser Gly Leu Gly
1               5                   10                  15

Cys

<210> SEQ ID NO 76
<211> LENGTH: 17
<212> TYPE: PRT
<213> ORGANISM: Artificial sequence
```

```
<220> FEATURE:
<223> OTHER INFORMATION: A portion of a natriuretic peptide

<400> SEQUENCE: 76

Cys Phe Gly Phe Pro Ile Asp Arg Ile Gly Ser Val Ser Gly Leu Gly
1               5                   10                  15

Cys

<210> SEQ ID NO 77
<211> LENGTH: 17
<212> TYPE: PRT
<213> ORGANISM: Artificial sequence
<220> FEATURE:
<223> OTHER INFORMATION: A portion of a natriuretic peptide

<400> SEQUENCE: 77

Cys Phe Gly Phe Pro Leu Asp Arg Ile Gly Ala Val Ser Gly Leu Gly
1               5                   10                  15

Cys

<210> SEQ ID NO 78
<211> LENGTH: 17
<212> TYPE: PRT
<213> ORGANISM: Artificial sequence
<220> FEATURE:
<223> OTHER INFORMATION: A portion of a natriuretic peptide

<400> SEQUENCE: 78

Cys Phe Gly Phe Pro Leu Asp Arg Ile Gly Ser Ser Ser Gly Leu Gly
1               5                   10                  15

Cys

<210> SEQ ID NO 79
<211> LENGTH: 17
<212> TYPE: PRT
<213> ORGANISM: Artificial sequence
<220> FEATURE:
<223> OTHER INFORMATION: A portion of a natriuretic peptide

<400> SEQUENCE: 79

Cys Phe Gly Phe Pro Leu Asp Arg Ile Gly Ser Gln Ser Gly Leu Gly
1               5                   10                  15

Cys

<210> SEQ ID NO 80
<211> LENGTH: 17
<212> TYPE: PRT
<213> ORGANISM: Artificial sequence
<220> FEATURE:
<223> OTHER INFORMATION: A portion of a natriuretic peptide

<400> SEQUENCE: 80

Cys Phe Gly Phe Pro Leu Asp Arg Ile Gly Ser Val Ser Asn Leu Gly
1               5                   10                  15

Cys

<210> SEQ ID NO 81
<211> LENGTH: 17
<212> TYPE: PRT
<213> ORGANISM: Artificial sequence
<220> FEATURE:
<223> OTHER INFORMATION: A portion of a natriuretic peptide

<400> SEQUENCE: 81
```

```
Cys Phe Gly Phe Pro Leu Asp Arg Ile Gly Ser Val Ser Arg Leu Gly
1               5                   10                  15

Cys

<210> SEQ ID NO 82
<211> LENGTH: 28
<212> TYPE: PRT
<213> ORGANISM: Homo sapiens

<400> SEQUENCE: 82

Ser Leu Arg Arg Ser Ser Cys Phe Gly Gly Arg Met Asp Arg Ile Gly
1               5                   10                  15

Ala Gln Ser Gly Leu Gly Cys Asn Ser Phe Arg Tyr
            20                  25

<210> SEQ ID NO 83
<211> LENGTH: 32
<212> TYPE: PRT
<213> ORGANISM: Homo sapiens

<400> SEQUENCE: 83

Ser Pro Lys Met Val Gln Gly Ser Gly Cys Phe Gly Arg Lys Met Asp
1               5                   10                  15

Arg Ile Ser Ser Ser Ser Gly Leu Gly Cys Lys Val Leu Arg Arg His
            20                  25                  30

<210> SEQ ID NO 84
<211> LENGTH: 29
<212> TYPE: PRT
<213> ORGANISM: Homo sapiens

<400> SEQUENCE: 84

Tyr Lys Gly Ala Asn Lys Lys Gly Leu Ser Lys Gly Cys Phe Gly Leu
1               5                   10                  15

Lys Leu Asp Arg Ile Gly Ser Met Ser Gly Leu Gly Cys
            20                  25

<210> SEQ ID NO 85
<211> LENGTH: 38
<212> TYPE: PRT
<213> ORGANISM: Dendroaspis angusticeps

<400> SEQUENCE: 85

Glu Val Lys Tyr Asp Pro Cys Phe Gly His Lys Ile Asp Arg Ile Asn
1               5                   10                  15

His Val Ser Asn Leu Gly Cys Pro Ser Leu Arg Asp Pro Arg Pro Asn
            20                  25                  30

Ala Pro Ser Thr Ser Ala
        35

<210> SEQ ID NO 86
<211> LENGTH: 38
<212> TYPE: PRT
<213> ORGANISM: Dendroaspis angusticeps

<400> SEQUENCE: 86

Gly Asp Asn Lys Pro Pro Lys Lys Gly Pro Pro Asn Gly Cys Phe Gly
1               5                   10                  15

His Lys Ile Asp Arg Ile Gly Ser His Ser Gly Leu Gly Cys Asn Lys
            20                  25                  30

Val Asp Asp Asn Lys Gly
        35
```

```
<210> SEQ ID NO 87
<211> LENGTH: 37
<212> TYPE: PRT
<213> ORGANISM: Dendroaspis angusticeps

<400> SEQUENCE: 87

Gly Glu Asn Glu Pro Lys Lys Ala Pro Asp Gly Cys Phe Gly
1               5                   10                  15

His Lys Ile Asp Arg Ile Gly Ser His Ser Gly Leu Gly Cys Asn Lys
                20                  25                  30

Phe Lys Pro Gly His
            35

<210> SEQ ID NO 88
<211> LENGTH: 17
<212> TYPE: PRT
<213> ORGANISM: Artificial sequence
<220> FEATURE:
<223> OTHER INFORMATION: Natriuretic peptide consensus sequence
<220> FEATURE:
<221> NAME/KEY: misc_feature
<222> LOCATION: (4)..(6)
<223> OTHER INFORMATION: Xaa can be any naturally occurring amino acid
<220> FEATURE:
<221> NAME/KEY: misc_feature
<222> LOCATION: (10)..(12)
<223> OTHER INFORMATION: Xaa can be any naturally occurring amino acid
<220> FEATURE:
<221> NAME/KEY: misc_feature
<222> LOCATION: (14)..(14)
<223> OTHER INFORMATION: Xaa can be any naturally occurring amino acid

<400> SEQUENCE: 88

Cys Phe Gly Xaa Xaa Xaa Asp Arg Ile Xaa Xaa Xaa Ser Xaa Leu Gly
1               5                   10                  15

Cys

<210> SEQ ID NO 89
<211> LENGTH: 35
<212> TYPE: PRT
<213> ORGANISM: Artificial sequence
<220> FEATURE:
<223> OTHER INFORMATION: A portion of a natriuretic peptide

<400> SEQUENCE: 89

Ser Asp Ser Lys Ile Gly Asp Gly Cys Phe Gly Leu Pro Leu Asp His
1               5                   10                  15

Ile Gly Ser Val Ser Gly Leu Gly Cys Asn Arg Pro Val Gln Asn Arg
                20                  25                  30

Pro Lys Lys
        35

<210> SEQ ID NO 90
<211> LENGTH: 35
<212> TYPE: PRT
<213> ORGANISM: Artificial sequence
<220> FEATURE:
<223> OTHER INFORMATION: A portion of a natriuretic peptide

<400> SEQUENCE: 90

Ser Asp Pro Lys Ile Gly Asp Gly Cys Phe Gly Leu Pro Leu Asp His
1               5                   10                  15

Ile Gly Ser Val Ser Gly Leu Gly Cys Asn Arg Pro Val Gln Asn Arg
                20                  25                  30
```

Pro Lys Lys
        35

<210> SEQ ID NO 91
<211> LENGTH: 39
<212> TYPE: PRT
<213> ORGANISM: Artificial sequence
<220> FEATURE:
<223> OTHER INFORMATION: A portion of a natriuretic peptide

<400> SEQUENCE: 91

Ser Asp Ser Lys Ile Gly Asn Gly Cys Phe Gly Phe Pro Leu Asp Arg
1               5                   10                  15

Ile Gly Ser Val Ser Gly Leu Gly Cys Asn Arg Ile Met Gln Asn Pro
            20                  25                  30

Pro Lys Lys Phe Ser Gly Glu
        35

<210> SEQ ID NO 92
<211> LENGTH: 39
<212> TYPE: PRT
<213> ORGANISM: Artificial sequence
<220> FEATURE:
<223> OTHER INFORMATION: A portion of a natriuretic peptide

<400> SEQUENCE: 92

Ser Asp Ser Lys Ile Gly Asn Gly Cys Phe Gly Phe Pro Leu Asp Arg
1               5                   10                  15

Ile Gly Ser Val Ser Gly Leu Gly Cys Asn Arg Ile Met Gln Asn Arg
            20                  25                  30

Pro Lys Lys Phe Ser Gly Glu
        35

<210> SEQ ID NO 93
<211> LENGTH: 39
<212> TYPE: PRT
<213> ORGANISM: Artificial sequence
<220> FEATURE:
<223> OTHER INFORMATION: A portion of a natriuretic peptide

<400> SEQUENCE: 93

Ser Asp Ser Lys Ile Gly Asn Gly Cys Phe Gly Phe Pro Leu Asp His
1               5                   10                  15

Ile Gly Ser Val Ser Gly Leu Gly Cys Asn Arg Ile Met Gln Asn Pro
            20                  25                  30

Pro Lys Lys Phe Ser Gly Glu
        35

<210> SEQ ID NO 94
<211> LENGTH: 39
<212> TYPE: PRT
<213> ORGANISM: Artificial sequence
<220> FEATURE:
<223> OTHER INFORMATION: A portion of a natriuretic peptide

<400> SEQUENCE: 94

Ser Asp Ser Lys Ile Gly Asn Gly Cys Phe Gly Phe Pro Leu Asp Arg
1               5                   10                  15

Ile Gly Ser Val Ser Gly Leu Gly Cys Asn Arg Pro Met Gln Asn Pro
            20                  25                  30

Pro Lys Lys Phe Ser Gly Glu
        35

```
<210> SEQ ID NO 95
<211> LENGTH: 39
<212> TYPE: PRT
<213> ORGANISM: Artificial sequence
<220> FEATURE:
<223> OTHER INFORMATION: A portion of a natriuretic peptide

<400> SEQUENCE: 95

Ser Asp Ser Lys Ile Gly Asn Gly Cys Phe Gly Phe Pro Leu Asp Arg
1               5                   10                  15

Ile Gly Ser Val Ser Gly Leu Gly Cys Asn Arg Ile Val Gln Asn Pro
            20                  25                  30

Pro Lys Lys Phe Ser Gly Glu
        35

<210> SEQ ID NO 96
<211> LENGTH: 39
<212> TYPE: PRT
<213> ORGANISM: Artificial sequence
<220> FEATURE:
<223> OTHER INFORMATION: A portion of a natriuretic peptide

<400> SEQUENCE: 96

Ser Asp Ser Lys Ile Gly Asn Gly Cys Phe Gly Phe Pro Leu Asp Arg
1               5                   10                  15

Ile Gly Ser Val Ser Gly Leu Gly Cys Asn Arg Ile Arg Gln Asn Pro
            20                  25                  30

Pro Lys Lys Phe Ser Gly Glu
        35

<210> SEQ ID NO 97
<211> LENGTH: 39
<212> TYPE: PRT
<213> ORGANISM: Artificial sequence
<220> FEATURE:
<223> OTHER INFORMATION: A portion of a natriuretic peptide

<400> SEQUENCE: 97

Ser Asp Ser Lys Ile Gly Asn Gly Cys Phe Gly Phe Pro Leu Asp Arg
1               5                   10                  15

Ile Gly Ser Val Ser Gly Leu Gly Cys Lys Arg Ile Met Gln Asn Arg
            20                  25                  30

Pro Lys Lys Phe Ser Gly Glu
        35

<210> SEQ ID NO 98
<211> LENGTH: 39
<212> TYPE: PRT
<213> ORGANISM: Artificial sequence
<220> FEATURE:
<223> OTHER INFORMATION: A portion of a natriuretic peptide
<220> FEATURE:
<221> NAME/KEY: MISC_FEATURE
<222> LOCATION: (9)..(9)
<223> OTHER INFORMATION: Xaa=Selenocysteine
<220> FEATURE:
<221> NAME/KEY: MISC_FEATURE
<222> LOCATION: (25)..(25)
<223> OTHER INFORMATION: Xaa=Selenocysteine

<400> SEQUENCE: 98

Ser Asp Ser Lys Ile Gly Asn Gly Xaa Phe Gly Phe Pro Leu Asp Arg
1               5                   10                  15

Ile Gly Ser Val Ser Gly Leu Gly Xaa Asn Arg Ile Met Gln Asn Pro
            20                  25                  30
```

Pro Lys Lys Phe Ser Gly Glu
        35

<210> SEQ ID NO 99
<211> LENGTH: 39
<212> TYPE: PRT
<213> ORGANISM: Artificial sequence
<220> FEATURE:
<223> OTHER INFORMATION: A portion of a natriuretic peptide
<220> FEATURE:
<221> NAME/KEY: MISC_FEATURE
<222> LOCATION: (25)..(25)
<223> OTHER INFORMATION: Xaa=Selenocysteine

<400> SEQUENCE: 99

Ser Asp Ser Lys Ile Gly Asn Gly Cys Phe Gly Phe Pro Leu Asp Arg
1               5                   10                  15

Ile Gly Ser Val Ser Gly Leu Gly Xaa Asn Arg Ile Met Gln Asn Pro
            20                  25                  30

Pro Lys Lys Phe Ser Gly Glu
        35

<210> SEQ ID NO 100
<211> LENGTH: 39
<212> TYPE: PRT
<213> ORGANISM: Artificial sequence
<220> FEATURE:
<223> OTHER INFORMATION: A portion of a natriuretic peptide
<220> FEATURE:
<221> NAME/KEY: MISC_FEATURE
<222> LOCATION: (9)..(9)
<223> OTHER INFORMATION: Xaa=Selenocysteine

<400> SEQUENCE: 100

Ser Asp Ser Lys Ile Gly Asn Gly Xaa Phe Gly Phe Pro Leu Asp Arg
1               5                   10                  15

Ile Gly Ser Val Ser Gly Leu Gly Cys Asn Arg Ile Met Gln Asn Pro
            20                  25                  30

Pro Lys Lys Phe Ser Gly Glu
        35

<210> SEQ ID NO 101
<211> LENGTH: 39
<212> TYPE: PRT
<213> ORGANISM: Artificial sequence
<220> FEATURE:
<223> OTHER INFORMATION: A portion of a natriuretic peptide

<400> SEQUENCE: 101

Ser Asp Ser Lys Ile Gly Gln Gly Cys Phe Gly Phe Pro Leu Asp Arg
1               5                   10                  15

Ile Gly Ser Val Ser Gly Leu Gly Cys Asn Arg Ile Met Gln Asn Pro
            20                  25                  30

Pro Lys Lys Phe Ser Gly Glu
        35

<210> SEQ ID NO 102
<211> LENGTH: 39
<212> TYPE: PRT
<213> ORGANISM: Artificial sequence
<220> FEATURE:
<223> OTHER INFORMATION: A portion of a natriuretic peptide

<400> SEQUENCE: 102

Ser Asp Ser Lys Ile Gly Ala Gly Cys Phe Gly Phe Pro Leu Asp Arg
1               5                   10                  15

Ile Gly Ser Val Ser Gly Leu Gly Cys Asn Arg Ile Met Gln Asn Pro
            20                  25                  30

Pro Lys Lys Phe Ser Gly Glu
        35

<210> SEQ ID NO 103
<211> LENGTH: 39
<212> TYPE: PRT
<213> ORGANISM: Artificial sequence
<220> FEATURE:
<223> OTHER INFORMATION: A portion of a natriuretic peptide

<400> SEQUENCE: 103

Ser Asp Ser Lys Ile Gly Lys Gly Cys Phe Gly Phe Pro Leu Asp Arg
1               5                   10                  15

Ile Gly Ser Val Ser Gly Leu Gly Cys Asn Arg Ile Met Gln Asn Pro
            20                  25                  30

Pro Lys Lys Phe Ser Gly Glu
        35

<210> SEQ ID NO 104
<211> LENGTH: 39
<212> TYPE: PRT
<213> ORGANISM: Artificial sequence
<220> FEATURE:
<223> OTHER INFORMATION: A portion of a natriuretic peptide

<400> SEQUENCE: 104

Ser Asp Ser Lys Ile Ser Lys Gly Cys Phe Gly Phe Pro Leu Asp Arg
1               5                   10                  15

Ile Gly Ser Val Ser Gly Leu Gly Cys Asn Arg Ile Met Gln Asn Pro
            20                  25                  30

Pro Lys Lys Phe Ser Gly Glu
        35

<210> SEQ ID NO 105
<211> LENGTH: 39
<212> TYPE: PRT
<213> ORGANISM: Artificial sequence
<220> FEATURE:
<223> OTHER INFORMATION: A portion of a natriuretic peptide

<400> SEQUENCE: 105

Ser Asp Ser Lys Ile Gly Ser Gly Cys Phe Gly Phe Pro Leu Asp Arg
1               5                   10                  15

Ile Gly Ser Val Ser Gly Leu Gly Cys Asn Arg Ile Met Gln Asn Pro
            20                  25                  30

Pro Lys Lys Phe Ser Gly Glu
        35

<210> SEQ ID NO 106
<211> LENGTH: 39
<212> TYPE: PRT
<213> ORGANISM: Artificial sequence
<220> FEATURE:
<223> OTHER INFORMATION: A portion of a natriuretic peptide

<400> SEQUENCE: 106

Ser Asp Ser Lys Ile Arg Ser Gly Cys Phe Gly Phe Pro Leu Asp Arg
1               5                   10                  15

Ile Gly Ser Val Ser Gly Leu Gly Cys Asn Arg Ile Met Gln Asn Pro
            20                  25                  30

```
Pro Lys Lys Phe Ser Gly Glu
        35

<210> SEQ ID NO 107
<211> LENGTH: 39
<212> TYPE: PRT
<213> ORGANISM: Artificial sequence
<220> FEATURE:
<223> OTHER INFORMATION: A portion of a natriuretic peptide

<400> SEQUENCE: 107

Ser Asp Ser Lys Ile Gly Asn Gly Cys Phe Gly Phe Pro Leu Asp Arg
1               5                   10                  15

Ile Gly Ser Val Ser Gly Leu Gly Cys Asn Arg Ile Asn Gln Asn Pro
            20                  25                  30

Pro Lys Lys Phe Ser Gly Glu
        35

<210> SEQ ID NO 108
<211> LENGTH: 39
<212> TYPE: PRT
<213> ORGANISM: Artificial sequence
<220> FEATURE:
<223> OTHER INFORMATION: A portion of a natriuretic peptide

<400> SEQUENCE: 108

Ser Asp Ser Lys Ile Gly Asn Gly Cys Phe Gly Phe Pro Leu Asp Arg
1               5                   10                  15

Ile Gly Ser Val Ser Gly Leu Gly Cys Asn Arg Ile Met Gln Ala Pro
            20                  25                  30

Pro Lys Lys Phe Ser Gly Glu
        35

<210> SEQ ID NO 109
<211> LENGTH: 39
<212> TYPE: PRT
<213> ORGANISM: Artificial sequence
<220> FEATURE:
<223> OTHER INFORMATION: A portion of a natriuretic peptide

<400> SEQUENCE: 109

Ser Asp Ser Lys Ile Gly Asn Gly Cys Phe Gly Phe Pro Leu Asp Arg
1               5                   10                  15

Ile Gly Ser Val Ser Gly Leu Gly Cys Asn Arg Ile Met Gln Gln Pro
            20                  25                  30

Pro Lys Lys Phe Ser Gly Glu
        35

<210> SEQ ID NO 110
<211> LENGTH: 39
<212> TYPE: PRT
<213> ORGANISM: Artificial sequence
<220> FEATURE:
<223> OTHER INFORMATION: A portion of a natriuretic peptide
<220> FEATURE:
<221> NAME/KEY: MISC_FEATURE
<222> LOCATION: (32)..(32)
<223> OTHER INFORMATION: Xaa=hydroxyproline

<400> SEQUENCE: 110

Ser Asp Ser Lys Ile Gly Asn Gly Cys Phe Gly Phe Pro Leu Asp Arg
1               5                   10                  15

Ile Gly Ser Val Ser Gly Leu Gly Cys Asn Arg Ile Met Gln Ala Xaa
            20                  25                  30
```

```
Pro Lys Lys Phe Ser Gly Glu
            35

<210> SEQ ID NO 111
<211> LENGTH: 39
<212> TYPE: PRT
<213> ORGANISM: Artificial sequence
<220> FEATURE:
<223> OTHER INFORMATION: A portion of a natriuretic peptide
<220> FEATURE:
<221> NAME/KEY: MISC_FEATURE
<222> LOCATION: (32)..(32)
<223> OTHER INFORMATION: Xaa=hydroxyproline

<400> SEQUENCE: 111

Ser Asp Ser Lys Ile Gly Asn Gly Cys Phe Gly Phe Pro Leu Asp Arg
1               5                   10                  15

Ile Gly Ser Val Ser Gly Leu Gly Cys Asn Arg Ile Met Gln Gln Xaa
            20                  25                  30

Pro Lys Lys Phe Ser Gly Glu
            35

<210> SEQ ID NO 112
<211> LENGTH: 40
<212> TYPE: PRT
<213> ORGANISM: Artificial sequence
<220> FEATURE:
<223> OTHER INFORMATION: A portion of a natriuretic peptide
<220> FEATURE:
<221> NAME/KEY: MISC_FEATURE
<222> LOCATION: (1)..(1)
<223> OTHER INFORMATION: Xaa=pyroglutamate

<400> SEQUENCE: 112

Xaa Ser Asp Ser Lys Ile Gly Asn Gly Cys Phe Gly Phe Pro Leu Asp
1               5                   10                  15

Arg Ile Gly Ser Val Ser Gly Leu Gly Cys Asn Arg Ile Met Gln Asn
            20                  25                  30

Pro Pro Lys Lys Phe Ser Gly Glu
            35                  40

<210> SEQ ID NO 113
<211> LENGTH: 39
<212> TYPE: PRT
<213> ORGANISM: Artificial sequence
<220> FEATURE:
<223> OTHER INFORMATION: A portion of a natriuretic peptide
<220> FEATURE:
<221> NAME/KEY: MISC_FEATURE
<222> LOCATION: (9)..(9)
<223> OTHER INFORMATION: Xaa=Selenocysteine
<220> FEATURE:
<221> NAME/KEY: MISC_FEATURE
<222> LOCATION: (25)..(25)
<223> OTHER INFORMATION: Xaa=Selenocysteine

<400> SEQUENCE: 113

Ser Asp Ser Lys Ile Gly Ala Gly Xaa Phe Gly Phe Pro Leu Asp Arg
1               5                   10                  15

Ile Gly Ser Val Ser Gly Leu Gly Xaa Asn Arg Ile Asn Gln Ala Pro
            20                  25                  30

Pro Lys Lys Phe Ser Gly Glu
            35

<210> SEQ ID NO 114
<211> LENGTH: 40
<212> TYPE: PRT
```

```
<213> ORGANISM: Artificial sequence
<220> FEATURE:
<223> OTHER INFORMATION: A portion of a natriuretic peptide
<220> FEATURE:
<221> NAME/KEY: MISC_FEATURE
<222> LOCATION: (1)..(1)
<223> OTHER INFORMATION: Xaa=pyroglutamate
<220> FEATURE:
<221> NAME/KEY: MISC_FEATURE
<222> LOCATION: (10)..(10)
<223> OTHER INFORMATION: Xaa=Selenocysteine
<220> FEATURE:
<221> NAME/KEY: MISC_FEATURE
<222> LOCATION: (26)..(26)
<223> OTHER INFORMATION: Xaa=Selenocysteine

<400> SEQUENCE: 114

Xaa Ser Asp Ser Lys Ile Gly Ala Gly Xaa Phe Gly Phe Pro Leu Asp
1               5                   10                  15

Arg Ile Gly Ser Val Ser Gly Leu Gly Xaa Asn Arg Ile Asn Gln Ala
            20                  25                  30

Pro Pro Lys Lys Phe Ser Gly Glu
        35                  40

<210> SEQ ID NO 115
<211> LENGTH: 40
<212> TYPE: PRT
<213> ORGANISM: Artificial sequence
<220> FEATURE:
<223> OTHER INFORMATION: A portion of a natriuretic peptide

<400> SEQUENCE: 115

Ser Pro Lys Met Val Gln Gly Ser Gly Cys Phe Gly Arg Lys Met Asp
1               5                   10                  15

Arg Ile Ser Ser Ser Ser Gly Leu Gly Cys Asn Arg Ile Met Gln Asn
            20                  25                  30

Pro Pro Lys Lys Phe Ser Gly Glu
        35                  40

<210> SEQ ID NO 116
<211> LENGTH: 32
<212> TYPE: PRT
<213> ORGANISM: Artificial sequence
<220> FEATURE:
<223> OTHER INFORMATION: A portion of a natriuretic peptide

<400> SEQUENCE: 116

Ser Pro Lys Met Val Gln Gly Ser Gly Cys Phe Gly Pro Leu Asp
1               5                   10              15

Arg Ile Gly Ser Val Ser Gly Leu Gly Cys Lys Val Leu Arg Arg His
            20                  25                  30

<210> SEQ ID NO 117
<211> LENGTH: 31
<212> TYPE: PRT
<213> ORGANISM: Artificial sequence
<220> FEATURE:
<223> OTHER INFORMATION: A portion of a natriuretic peptide

<400> SEQUENCE: 117

Ser Asp Ser Lys Ile Gly Asn Gly Cys Phe Gly Arg Lys Met Asp Arg
1               5                   10                  15

Ile Ser Ser Ser Ser Gly Leu Gly Cys Lys Val Leu Arg Arg His
            20                  25                  30

<210> SEQ ID NO 118
```

```
<211> LENGTH: 40
<212> TYPE: PRT
<213> ORGANISM: Artificial sequence
<220> FEATURE:
<223> OTHER INFORMATION: A portion of a natriuretic peptide

<400> SEQUENCE: 118

Ser Pro Lys Met Val Gln Gly Ser Gly Cys Phe Gly Phe Pro Leu Asp
1               5                   10                  15

Arg Ile Gly Ser Val Ser Gly Leu Gly Cys Asn Arg Ile Met Gln Asn
            20                  25                  30

Pro Pro Lys Lys Phe Ser Gly Glu
        35                  40

<210> SEQ ID NO 119
<211> LENGTH: 39
<212> TYPE: PRT
<213> ORGANISM: Artificial sequence
<220> FEATURE:
<223> OTHER INFORMATION: A portion of a natriuretic peptide

<400> SEQUENCE: 119

Ser Asp Ser Lys Ile Gly Asn Gly Cys Phe Gly Arg Lys Met Asp Arg
1               5                   10                  15

Ile Ser Ser Ser Ser Gly Leu Gly Cys Asn Arg Ile Met Gln Asn Pro
            20                  25                  30

Pro Lys Lys Phe Ser Gly Glu
        35

<210> SEQ ID NO 120
<211> LENGTH: 31
<212> TYPE: PRT
<213> ORGANISM: Artificial sequence
<220> FEATURE:
<223> OTHER INFORMATION: A portion of a natriuretic peptide

<400> SEQUENCE: 120

Ser Asp Ser Lys Ile Gly Asn Gly Cys Phe Gly Phe Pro Leu Asp Arg
1               5                   10                  15

Ile Gly Ser Val Ser Gly Leu Gly Cys Lys Val Leu Arg Arg His
            20                  25                  30

<210> SEQ ID NO 121
<211> LENGTH: 37
<212> TYPE: PRT
<213> ORGANISM: Artificial sequence
<220> FEATURE:
<223> OTHER INFORMATION: A portion of a natriuretic peptide

<400> SEQUENCE: 121

Ser Leu Arg Arg Ser Ser Cys Phe Gly Gly Arg Met Asp Arg Ile Gly
1               5                   10                  15

Ala Gln Ser Gly Leu Gly Cys Asn Arg Ile Met Gln Asn Pro Pro Lys
            20                  25                  30

Lys Phe Ser Gly Glu
        35

<210> SEQ ID NO 122
<211> LENGTH: 28
<212> TYPE: PRT
<213> ORGANISM: Artificial sequence
<220> FEATURE:
<223> OTHER INFORMATION: A portion of a natriuretic peptide

<400> SEQUENCE: 122
```

Ser Leu Arg Arg Ser Ser Cys Phe Gly Phe Pro Leu Asp Arg Ile Gly
1               5                   10                  15

Ser Val Ser Gly Leu Gly Cys Asn Ser Phe Arg Tyr
            20                  25

<210> SEQ ID NO 123
<211> LENGTH: 30
<212> TYPE: PRT
<213> ORGANISM: Artificial sequence
<220> FEATURE:
<223> OTHER INFORMATION: A portion of a natriuretic peptide

<400> SEQUENCE: 123

Ser Asp Ser Lys Ile Gly Asn Gly Cys Phe Gly Gly Arg Met Asp Arg
1               5                   10                  15

Ile Gly Ala Gln Ser Gly Leu Gly Cys Asn Ser Phe Arg Tyr
            20                  25                  30

<210> SEQ ID NO 124
<211> LENGTH: 37
<212> TYPE: PRT
<213> ORGANISM: Artificial sequence
<220> FEATURE:
<223> OTHER INFORMATION: A portion of a natriuretic peptide

<400> SEQUENCE: 124

Ser Leu Arg Arg Ser Ser Cys Phe Gly Phe Pro Leu Asp Arg Ile Gly
1               5                   10                  15

Ser Val Ser Gly Leu Gly Cys Asn Arg Ile Met Gln Asn Pro Pro Lys
            20                  25                  30

Lys Phe Ser Gly Glu
        35

<210> SEQ ID NO 125
<211> LENGTH: 39
<212> TYPE: PRT
<213> ORGANISM: Artificial sequence
<220> FEATURE:
<223> OTHER INFORMATION: A portion of a natriuretic peptide

<400> SEQUENCE: 125

Ser Asp Ser Lys Ile Gly Asn Gly Cys Phe Gly Gly Arg Met Asp Arg
1               5                   10                  15

Ile Gly Ala Gln Ser Gly Leu Gly Cys Asn Arg Ile Met Gln Asn Pro
            20                  25                  30

Pro Lys Lys Phe Ser Gly Glu
        35

<210> SEQ ID NO 126
<211> LENGTH: 30
<212> TYPE: PRT
<213> ORGANISM: Artificial sequence
<220> FEATURE:
<223> OTHER INFORMATION: A portion of a natriuretic peptide

<400> SEQUENCE: 126

Ser Asp Ser Lys Ile Gly Asn Gly Cys Phe Gly Phe Pro Leu Asp Arg
1               5                   10                  15

Ile Gly Ser Val Ser Gly Leu Gly Cys Asn Ser Phe Arg Tyr
            20                  25                  30

<210> SEQ ID NO 127
<211> LENGTH: 37

```
<212> TYPE: PRT
<213> ORGANISM: Artificial sequence
<220> FEATURE:
<223> OTHER INFORMATION: A portion of a natriuretic peptide

<400> SEQUENCE: 127

Glu Val Lys Tyr Asp Pro Cys Phe Gly His Lys Ile Asp Arg Ile Asn
1               5                   10                  15

His Val Ser Asn Leu Gly Cys Asn Arg Ile Met Gln Asn Pro Pro Lys
            20                  25                  30

Lys Phe Ser Gly Glu
        35

<210> SEQ ID NO 128
<211> LENGTH: 38
<212> TYPE: PRT
<213> ORGANISM: Artificial sequence
<220> FEATURE:
<223> OTHER INFORMATION: A portion of a natriuretic peptide

<400> SEQUENCE: 128

Glu Val Lys Tyr Asp Pro Cys Phe Gly Phe Pro Leu Asp Arg Ile Gly
1               5                   10                  15

Ser Val Ser Gly Leu Gly Cys Pro Ser Leu Arg Asp Pro Arg Pro Asn
            20                  25                  30

Ala Pro Ser Thr Ser Ala
        35

<210> SEQ ID NO 129
<211> LENGTH: 40
<212> TYPE: PRT
<213> ORGANISM: Artificial sequence
<220> FEATURE:
<223> OTHER INFORMATION: A portion of a natriuretic peptide

<400> SEQUENCE: 129

Ser Asp Ser Lys Ile Gly Asn Gly Cys Phe Gly His Lys Ile Asp Arg
1               5                   10                  15

Ile Asn His Val Ser Asn Leu Gly Cys Pro Ser Leu Arg Asp Pro Arg
            20                  25                  30

Pro Asn Ala Pro Ser Thr Ser Ala
        35                  40

<210> SEQ ID NO 130
<211> LENGTH: 37
<212> TYPE: PRT
<213> ORGANISM: Artificial sequence
<220> FEATURE:
<223> OTHER INFORMATION: A portion of a natriuretic peptide

<400> SEQUENCE: 130

Glu Val Lys Tyr Asp Pro Cys Phe Gly Phe Pro Leu Asp Arg Ile Gly
1               5                   10                  15

Ser Val Ser Gly Leu Gly Cys Asn Arg Ile Met Gln Asn Pro Pro Lys
            20                  25                  30

Lys Phe Ser Gly Glu
        35

<210> SEQ ID NO 131
<211> LENGTH: 39
<212> TYPE: PRT
<213> ORGANISM: Artificial sequence
<220> FEATURE:
<223> OTHER INFORMATION: A portion of a natriuretic peptide
```

-continued

```
<400> SEQUENCE: 131

Ser Asp Ser Lys Ile Gly Asn Gly Cys Phe Gly His Lys Ile Asp Arg
1               5                   10                  15

Ile Asn His Val Ser Asn Leu Gly Cys Asn Arg Ile Met Gln Asn Pro
            20                  25                  30

Pro Lys Lys Phe Ser Gly Glu
        35

<210> SEQ ID NO 132
<211> LENGTH: 38
<212> TYPE: PRT
<213> ORGANISM: Artificial sequence
<220> FEATURE:
<223> OTHER INFORMATION: A portion of a natriuretic peptide

<400> SEQUENCE: 132

Glu Val Lys Tyr Asp Pro Cys Phe Gly Phe Pro Leu Asp Arg Ile Gly
1               5                   10                  15

Ser Val Ser Gly Leu Gly Cys Pro Ser Leu Arg Asp Pro Arg Pro Asn
            20                  25                  30

Ala Pro Ser Thr Ser Ala
        35

<210> SEQ ID NO 133
<211> LENGTH: 39
<212> TYPE: PRT
<213> ORGANISM: Artificial sequence
<220> FEATURE:
<223> OTHER INFORMATION: A portion of a natriuretic peptide

<400> SEQUENCE: 133

Ser Asp Ser Lys Ile Gly Asn Gly Cys Phe Gly His Lys Ile Asp Arg
1               5                   10                  15

Ile Gly Ser His Ser Gly Leu Gly Cys Asn Arg Ile Met Gln Asn Pro
            20                  25                  30

Pro Lys Lys Phe Ser Gly Glu
        35

<210> SEQ ID NO 134
<211> LENGTH: 37
<212> TYPE: PRT
<213> ORGANISM: Artificial sequence
<220> FEATURE:
<223> OTHER INFORMATION: A portion of a natriuretic peptide

<400> SEQUENCE: 134

Glu Val Lys Tyr Asp Pro Cys Phe Gly His Lys Ile Asp Arg Ile Gly
1               5                   10                  15

Ser His Ser Gly Leu Gly Cys Asn Arg Ile Met Gln Asn Pro Pro Lys
            20                  25                  30

Lys Phe Ser Gly Glu
        35

<210> SEQ ID NO 135
<211> LENGTH: 39
<212> TYPE: PRT
<213> ORGANISM: Artificial sequence
<220> FEATURE:
<223> OTHER INFORMATION: A portion of a natriuretic peptide
<220> FEATURE:
<221> NAME/KEY: MISC_FEATURE
<222> LOCATION: (1)..(1)
<223> OTHER INFORMATION: Xaa=pyroglutamate
```

```
<400> SEQUENCE: 135

Xaa Asp Ser Lys Ile Gly Asn Gly Cys Phe Gly Phe Pro Leu Asp Arg
1               5                   10                  15

Ile Gly Ser Val Ser Gly Leu Gly Cys Asn Arg Ile Met Gln Asn Pro
            20                  25                  30

Pro Lys Lys Phe Ser Gly Glu
        35

<210> SEQ ID NO 136
<211> LENGTH: 39
<212> TYPE: PRT
<213> ORGANISM: Artificial sequence
<220> FEATURE:
<223> OTHER INFORMATION: A portion of a natriuretic peptide

<400> SEQUENCE: 136

Ser Asp Ser Ala Ile Gly Asn Gly Cys Phe Gly Phe Pro Leu Asp Arg
1               5                   10                  15

Ile Gly Ser Val Ser Gly Leu Gly Cys Asn Arg Ile Met Gln Asn Pro
            20                  25                  30

Pro Lys Lys Phe Ser Gly Glu
        35

<210> SEQ ID NO 137
<211> LENGTH: 39
<212> TYPE: PRT
<213> ORGANISM: Artificial sequence
<220> FEATURE:
<223> OTHER INFORMATION: A portion of a natriuretic peptide

<400> SEQUENCE: 137

Ser Asp Ser Lys Ala Gly Asn Gly Cys Phe Gly Phe Pro Leu Asp Arg
1               5                   10                  15

Ile Gly Ser Val Ser Gly Leu Gly Cys Asn Arg Ile Met Gln Asn Pro
            20                  25                  30

Pro Lys Lys Phe Ser Gly Glu
        35

<210> SEQ ID NO 138
<211> LENGTH: 39
<212> TYPE: PRT
<213> ORGANISM: Artificial sequence
<220> FEATURE:
<223> OTHER INFORMATION: A portion of a natriuretic peptide

<400> SEQUENCE: 138

Ser Asp Ser Lys Ile Gly Asn Gly Cys Ala Gly Phe Pro Leu Asp Arg
1               5                   10                  15

Ile Gly Ser Val Ser Gly Leu Gly Cys Asn Arg Ile Met Gln Asn Pro
            20                  25                  30

Pro Lys Lys Phe Ser Gly Glu
        35

<210> SEQ ID NO 139
<211> LENGTH: 39
<212> TYPE: PRT
<213> ORGANISM: Artificial sequence
<220> FEATURE:
<223> OTHER INFORMATION: A portion of a natriuretic peptide

<400> SEQUENCE: 139

Ser Asp Ser Lys Ile Gly Asn Gly Cys Phe Gly Ala Pro Leu Asp Arg
```

```
                1               5                   10                  15
Ile Gly Ser Val Ser Gly Leu Gly Cys Asn Arg Ile Met Gln Asn Pro
            20                  25                  30

Pro Lys Lys Phe Ser Gly Glu
            35
```

<210> SEQ ID NO 140
<211> LENGTH: 39
<212> TYPE: PRT
<213> ORGANISM: Artificial sequence
<220> FEATURE:
<223> OTHER INFORMATION: A portion of a natriuretic peptide

<400> SEQUENCE: 140

```
Ser Asp Ser Lys Ile Gly Asn Gly Cys Phe Gly Phe Pro Ala Asp Arg
1               5                   10                  15

Ile Gly Ser Val Ser Gly Leu Gly Cys Asn Arg Ile Met Gln Asn Pro
            20                  25                  30

Pro Lys Lys Phe Ser Gly Glu
            35
```

<210> SEQ ID NO 141
<211> LENGTH: 39
<212> TYPE: PRT
<213> ORGANISM: Artificial sequence
<220> FEATURE:
<223> OTHER INFORMATION: A portion of a natriuretic peptide

<400> SEQUENCE: 141

```
Ser Asp Ser Lys Ile Gly Asn Gly Cys Phe Gly Phe Pro Leu Ala Arg
1               5                   10                  15

Ile Gly Ser Val Ser Gly Leu Gly Cys Asn Arg Ile Met Gln Asn Pro
            20                  25                  30

Pro Lys Lys Phe Ser Gly Glu
            35
```

<210> SEQ ID NO 142
<211> LENGTH: 39
<212> TYPE: PRT
<213> ORGANISM: Artificial sequence
<220> FEATURE:
<223> OTHER INFORMATION: A portion of a natriuretic peptide

<400> SEQUENCE: 142

```
Ser Asp Ser Lys Ile Gly Asn Gly Cys Phe Gly Phe Pro Leu Asp Ala
1               5                   10                  15

Ile Gly Ser Val Ser Gly Leu Gly Cys Asn Arg Ile Met Gln Asn Pro
            20                  25                  30

Pro Lys Lys Phe Ser Gly Glu
            35
```

<210> SEQ ID NO 143
<211> LENGTH: 39
<212> TYPE: PRT
<213> ORGANISM: Artificial sequence
<220> FEATURE:
<223> OTHER INFORMATION: A portion of a natriuretic peptide

<400> SEQUENCE: 143

```
Ser Asp Ser Lys Ile Gly Asn Gly Cys Phe Gly Phe Pro Leu Asp Arg
1               5                   10                  15

Ala Gly Ser Val Ser Gly Leu Gly Cys Asn Arg Ile Met Gln Asn Pro
            20                  25                  30
```

```
Pro Lys Lys Phe Ser Gly Glu
        35

<210> SEQ ID NO 144
<211> LENGTH: 39
<212> TYPE: PRT
<213> ORGANISM: Artificial sequence
<220> FEATURE:
<223> OTHER INFORMATION: A portion of a natriuretic peptide

<400> SEQUENCE: 144

Ser Asp Ser Lys Ile Gly Asn Gly Cys Phe Gly Phe Pro Leu Asp Arg
1               5                   10                  15

Ile Gly Ser Ala Ser Gly Leu Gly Cys Asn Arg Ile Met Gln Asn Pro
            20                  25                  30

Pro Lys Lys Phe Ser Gly Glu
        35

<210> SEQ ID NO 145
<211> LENGTH: 39
<212> TYPE: PRT
<213> ORGANISM: Artificial sequence
<220> FEATURE:
<223> OTHER INFORMATION: A portion of a natriuretic peptide

<400> SEQUENCE: 145

Ser Asp Ser Lys Ile Gly Asn Gly Cys Phe Gly Phe Pro Leu Asp Arg
1               5                   10                  15

Ile Gly Ser Val Ser Gly Ala Gly Cys Asn Arg Ile Met Gln Asn Pro
            20                  25                  30

Pro Lys Lys Phe Ser Gly Glu
        35

<210> SEQ ID NO 146
<211> LENGTH: 39
<212> TYPE: PRT
<213> ORGANISM: Artificial sequence
<220> FEATURE:
<223> OTHER INFORMATION: A portion of a natriuretic peptide

<400> SEQUENCE: 146

Ser Asp Ser Lys Ile Gly Asn Gly Cys Phe Gly Phe Pro Leu Asp Arg
1               5                   10                  15

Ile Gly Ser Val Ser Gly Leu Gly Cys Ala Arg Ile Met Gln Asn Pro
            20                  25                  30

Pro Lys Lys Phe Ser Gly Glu
        35

<210> SEQ ID NO 147
<211> LENGTH: 39
<212> TYPE: PRT
<213> ORGANISM: Artificial sequence
<220> FEATURE:
<223> OTHER INFORMATION: A portion of a natriuretic peptide

<400> SEQUENCE: 147

Ser Asp Ser Lys Ile Gly Asn Gly Cys Phe Gly Phe Pro Leu Asp Arg
1               5                   10                  15

Ile Gly Ser Val Ser Gly Leu Gly Cys Asn Ala Ile Met Gln Asn Pro
            20                  25                  30

Pro Lys Lys Phe Ser Gly Glu
        35
```

```
<210> SEQ ID NO 148
<211> LENGTH: 39
<212> TYPE: PRT
<213> ORGANISM: Artificial sequence
<220> FEATURE:
<223> OTHER INFORMATION: A portion of a natriuretic peptide

<400> SEQUENCE: 148

Ser Asp Ser Lys Ile Gly Asn Gly Cys Phe Gly Phe Pro Leu Asp Arg
1               5                   10                  15

Ile Gly Ser Val Ser Gly Leu Gly Cys Asn Arg Ala Met Gln Asn Pro
            20                  25                  30

Pro Lys Lys Phe Ser Gly Glu
        35

<210> SEQ ID NO 149
<211> LENGTH: 39
<212> TYPE: PRT
<213> ORGANISM: Artificial sequence
<220> FEATURE:
<223> OTHER INFORMATION: A portion of a natriuretic peptide

<400> SEQUENCE: 149

Ser Asp Ser Lys Ile Gly Asn Gly Cys Phe Gly Phe Pro Leu Asp Arg
1               5                   10                  15

Ile Gly Ser Val Ser Gly Leu Gly Cys Asn Arg Ile Ala Gln Asn Pro
            20                  25                  30

Pro Lys Lys Phe Ser Gly Glu
        35

<210> SEQ ID NO 150
<211> LENGTH: 39
<212> TYPE: PRT
<213> ORGANISM: Artificial sequence
<220> FEATURE:
<223> OTHER INFORMATION: A portion of a natriuretic peptide

<400> SEQUENCE: 150

Ser Asp Ser Lys Ile Gly Asn Gly Cys Phe Gly Phe Pro Leu Asp Arg
1               5                   10                  15

Ile Gly Ser Val Ser Gly Leu Gly Cys Asn Arg Ile Met Ala Asn Pro
            20                  25                  30

Pro Lys Lys Phe Ser Gly Glu
        35

<210> SEQ ID NO 151
<211> LENGTH: 39
<212> TYPE: PRT
<213> ORGANISM: Artificial sequence
<220> FEATURE:
<223> OTHER INFORMATION: A portion of a natriuretic peptide

<400> SEQUENCE: 151

Ser Asp Ser Lys Ile Gly Asn Gly Cys Phe Gly Phe Pro Leu Asp Arg
1               5                   10                  15

Ile Gly Ser Val Ser Gly Leu Gly Cys Asn Arg Ile Met Gln Ala Pro
            20                  25                  30

Pro Lys Lys Phe Ser Gly Glu
        35

<210> SEQ ID NO 152
<211> LENGTH: 39
<212> TYPE: PRT
```

```
<213> ORGANISM: Artificial sequence
<220> FEATURE:
<223> OTHER INFORMATION: A portion of a natriuretic peptide

<400> SEQUENCE: 152

Ser Asp Ser Lys Ile Gly Asn Gly Cys Phe Gly Phe Pro Leu Asp Arg
1               5                   10                  15

Ile Gly Ser Val Ser Gly Leu Gly Cys Asn Arg Ile Met Gln Asn Pro
            20                  25                  30

Pro Ala Lys Phe Ser Gly Glu
        35

<210> SEQ ID NO 153
<211> LENGTH: 39
<212> TYPE: PRT
<213> ORGANISM: Artificial sequence
<220> FEATURE:
<223> OTHER INFORMATION: A portion of a natriuretic peptide

<400> SEQUENCE: 153

Ser Asp Ser Lys Ile Gly Asn Gly Cys Phe Gly Phe Pro Leu Asp Arg
1               5                   10                  15

Ile Gly Ser Val Ser Gly Leu Gly Cys Asn Arg Ile Met Gln Asn Pro
            20                  25                  30

Pro Lys Ala Phe Ser Gly Glu
        35

<210> SEQ ID NO 154
<211> LENGTH: 39
<212> TYPE: PRT
<213> ORGANISM: Artificial sequence
<220> FEATURE:
<223> OTHER INFORMATION: A portion of a natriuretic peptide

<400> SEQUENCE: 154

Ser Asp Ser Lys Ile Gly Asn Gly Cys Phe Gly Phe Pro Leu Asp Arg
1               5                   10                  15

Ile Gly Ser Val Ser Gly Leu Gly Cys Asn Arg Ile Met Gln Asn Pro
            20                  25                  30

Pro Lys Lys Ala Ser Gly Glu
        35

<210> SEQ ID NO 155
<211> LENGTH: 39
<212> TYPE: PRT
<213> ORGANISM: Artificial sequence
<220> FEATURE:
<223> OTHER INFORMATION: A portion of a natriuretic peptide

<400> SEQUENCE: 155

Ser Asp Ser Lys Ile Gly Asn Gly Cys Phe Gly Phe Pro Leu Asp Arg
1               5                   10                  15

Ile Gly Ser Val Ser Gly Leu Gly Cys Asn Arg Ile Met Gln Asn Pro
            20                  25                  30

Pro Lys Lys Phe Ser Gly Ala
        35

<210> SEQ ID NO 156
<211> LENGTH: 39
<212> TYPE: PRT
<213> ORGANISM: Artificial sequence
<220> FEATURE:
<223> OTHER INFORMATION: A portion of a natriuretic peptide
```

<400> SEQUENCE: 156

Ser Asp Ser Gln Ile Gly Asn Gly Cys Phe Gly Phe Pro Leu Asp Arg
1               5                   10                  15

Ile Gly Ser Val Ser Gly Leu Gly Cys Asn Arg Ile Met Gln Asn Pro
            20                  25                  30

Pro Lys Lys Phe Ser Gly Glu
        35

<210> SEQ ID NO 157
<211> LENGTH: 39
<212> TYPE: PRT
<213> ORGANISM: Artificial sequence
<220> FEATURE:
<223> OTHER INFORMATION: A portion of a natriuretic peptide

<400> SEQUENCE: 157

Ser Asp Ser Lys Ile Gly Asn Gly Cys Phe Gly Phe Pro Leu Asp Gln
1               5                   10                  15

Ile Gly Ser Val Ser Gly Leu Gly Cys Asn Arg Ile Met Gln Asn Pro
            20                  25                  30

Pro Lys Lys Phe Ser Gly Glu
        35

<210> SEQ ID NO 158
<211> LENGTH: 39
<212> TYPE: PRT
<213> ORGANISM: Artificial sequence
<220> FEATURE:
<223> OTHER INFORMATION: A portion of a natriuretic peptide

<400> SEQUENCE: 158

Ser Asp Ser Lys Ile Gly Asn Gly Cys Phe Gly Phe Pro Leu Asp Arg
1               5                   10                  15

Ile Gly Ser Val Ser Gly Leu Gly Cys Asn Gln Ile Met Gln Asn Pro
            20                  25                  30

Pro Lys Lys Phe Ser Gly Glu
        35

<210> SEQ ID NO 159
<211> LENGTH: 39
<212> TYPE: PRT
<213> ORGANISM: Artificial sequence
<220> FEATURE:
<223> OTHER INFORMATION: A portion of a natriuretic peptide

<400> SEQUENCE: 159

Ser Asp Ser Lys Ile Gly Asn Gly Cys Phe Gly Phe Pro Leu Asp Arg
1               5                   10                  15

Ile Gly Ser Val Ser Gly Leu Gly Cys Asn Arg Ile Met Gln Asn Pro
            20                  25                  30

Pro Gln Lys Phe Ser Gly Glu
        35

<210> SEQ ID NO 160
<211> LENGTH: 39
<212> TYPE: PRT
<213> ORGANISM: Artificial sequence
<220> FEATURE:
<223> OTHER INFORMATION: A portion of a natriuretic peptide

<400> SEQUENCE: 160

Ser Asp Ser Lys Ile Gly Asn Gly Cys Phe Gly Phe Pro Leu Asp Arg
1               5                   10                  15

Ile Gly Ser Val Ser Gly Leu Gly Cys Asn Arg Ile Met Gln Asn Pro
            20                  25                  30

Pro Lys Gln Phe Ser Gly Glu
        35

<210> SEQ ID NO 161
<211> LENGTH: 39
<212> TYPE: PRT
<213> ORGANISM: Artificial sequence
<220> FEATURE:
<223> OTHER INFORMATION: A portion of a natriuretic peptide

<400> SEQUENCE: 161

Ser Asp Ser Lys Ile Gly Asn Gly Cys Phe Gly Phe Pro Leu Asp Arg
1               5                   10                  15

Ile Gly Ser Val Ser Gly Leu Gly Cys Asn Arg Ile Met Gln Pro Arg
            20                  25                  30

Pro Lys Lys Phe Ser Gly Glu
        35

<210> SEQ ID NO 162
<211> LENGTH: 39
<212> TYPE: PRT
<213> ORGANISM: Artificial sequence
<220> FEATURE:
<223> OTHER INFORMATION: A portion of a natriuretic peptide

<400> SEQUENCE: 162

Ser Asp Ser Glu Ile Gly Asn Gly Cys Phe Gly Phe Pro Leu Asp Arg
1               5                   10                  15

Ile Gly Ser Val Ser Gly Leu Gly Cys Asn Arg Ile Met Gln Asn Pro
            20                  25                  30

Pro Lys Lys Phe Ser Gly Glu
        35

<210> SEQ ID NO 163
<211> LENGTH: 39
<212> TYPE: PRT
<213> ORGANISM: Artificial sequence
<220> FEATURE:
<223> OTHER INFORMATION: A portion of a natriuretic peptide

<400> SEQUENCE: 163

Ser Asp Ser Lys Ile Gly Asn Gly Cys Phe Gly Phe Pro Leu Asp Glu
1               5                   10                  15

Ile Gly Ser Val Ser Gly Leu Gly Cys Asn Arg Ile Met Gln Asn Pro
            20                  25                  30

Pro Lys Lys Phe Ser Gly Glu
        35

<210> SEQ ID NO 164
<211> LENGTH: 39
<212> TYPE: PRT
<213> ORGANISM: Artificial sequence
<220> FEATURE:
<223> OTHER INFORMATION: A portion of a natriuretic peptide

<400> SEQUENCE: 164

Ser Asp Ser Lys Ile Gly Asn Gly Cys Phe Gly Phe Pro Leu Asp Arg
1               5                   10                  15

Ile Gly Ser Val Ser Gly Leu Gly Cys Asn Glu Ile Met Gln Asn Pro
            20                  25                  30

```
Pro Lys Lys Phe Ser Gly Glu
        35

<210> SEQ ID NO 165
<211> LENGTH: 39
<212> TYPE: PRT
<213> ORGANISM: Artificial sequence
<220> FEATURE:
<223> OTHER INFORMATION: A portion of a natriuretic peptide

<400> SEQUENCE: 165

Ser Asp Ser Lys Ile Gly Asn Gly Cys Phe Gly Phe Pro Leu Asp Arg
1               5                   10                  15

Ile Gly Ser Val Ser Gly Leu Gly Cys Asn Arg Ile Met Gln Asn Pro
            20                  25                  30

Pro Glu Lys Phe Ser Gly Glu
        35

<210> SEQ ID NO 166
<211> LENGTH: 39
<212> TYPE: PRT
<213> ORGANISM: Artificial sequence
<220> FEATURE:
<223> OTHER INFORMATION: A portion of a natriuretic peptide

<400> SEQUENCE: 166

Ser Asp Ser Lys Ile Gly Asn Gly Cys Phe Gly Phe Pro Leu Asp Arg
1               5                   10                  15

Ile Gly Ser Val Ser Gly Leu Gly Cys Asn Arg Ile Met Gln Asn Pro
            20                  25                  30

Pro Lys Glu Phe Ser Gly Glu
        35

<210> SEQ ID NO 167
<211> LENGTH: 39
<212> TYPE: PRT
<213> ORGANISM: Artificial sequence
<220> FEATURE:
<223> OTHER INFORMATION: A portion of a natriuretic peptide

<400> SEQUENCE: 167

Ser Asp Ser Lys Ile Gly Asn Gly Cys Phe Gly Phe Pro Leu Asp Arg
1               5                   10                  15

Ile Gly Ser Val Ser Gly Leu Gly Cys Lys Val Leu Arg Arg His Pro
            20                  25                  30

Pro Lys Lys Phe Ser Gly Glu
        35

<210> SEQ ID NO 168
<211> LENGTH: 39
<212> TYPE: PRT
<213> ORGANISM: Artificial sequence
<220> FEATURE:
<223> OTHER INFORMATION: A portion of a natriuretic peptide

<400> SEQUENCE: 168

Ser Asp Ser Lys Ile Gly Asn Gly Cys Phe Gly Tyr Pro Leu Asp Arg
1               5                   10                  15

Ile Gly Ser Val Ser Gly Leu Gly Cys Asn Arg Ile Met Gln Asn Pro
            20                  25                  30

Pro Lys Lys Phe Ser Gly Glu
        35
```

```
<210> SEQ ID NO 169
<211> LENGTH: 41
<212> TYPE: PRT
<213> ORGANISM: Artificial sequence
<220> FEATURE:
<223> OTHER INFORMATION: A portion of a natriuretic peptide

<400> SEQUENCE: 169

Ser Asp Ser Lys Ile Gly Asn Gly Cys Phe Gly Phe Pro Leu Asp Arg
1               5                   10                  15

Ile Gly Ser Val Ser Gly Leu Gly Cys Asn Arg Ile Met Gln Asn Pro
            20                  25                  30

Pro Lys Lys Phe Ser Gly Glu Asn His
        35                  40

<210> SEQ ID NO 170
<211> LENGTH: 41
<212> TYPE: PRT
<213> ORGANISM: Artificial sequence
<220> FEATURE:
<223> OTHER INFORMATION: A portion of a natriuretic peptide
<220> FEATURE:
<221> NAME/KEY: MISC_FEATURE
<222> LOCATION: (1)..(1)
<223> OTHER INFORMATION: Z=pyroglutamate

<400> SEQUENCE: 170

Glx Asp Ser Lys Ile Gly Asn Gly Cys Phe Gly Phe Pro Leu Asp Arg
1               5                   10                  15

Ile Gly Ser Val Ser Gly Leu Gly Cys Asn Arg Ile Met Gln Asn Pro
            20                  25                  30

Pro Lys Lys Phe Ser Gly Glu Asn His
        35                  40

<210> SEQ ID NO 171
<211> LENGTH: 39
<212> TYPE: PRT
<213> ORGANISM: Artificial sequence
<220> FEATURE:
<223> OTHER INFORMATION: A portion of a natriuretic peptide

<400> SEQUENCE: 171

Ser Asp Ser Lys Leu Gly Asn Gly Cys Phe Gly Phe Pro Leu Asp Arg
1               5                   10                  15

Ile Gly Ser Val Ser Gly Leu Gly Cys Asn Arg Ile Met Gln Asn Pro
            20                  25                  30

Pro Lys Lys Phe Ser Gly Glu
        35

<210> SEQ ID NO 172
<211> LENGTH: 39
<212> TYPE: PRT
<213> ORGANISM: Artificial sequence
<220> FEATURE:
<223> OTHER INFORMATION: A portion of a natriuretic peptide

<400> SEQUENCE: 172

Ser Asp Ser Lys Ile Gly Asn Gly Cys Leu Gly Phe Pro Leu Asp Arg
1               5                   10                  15

Ile Gly Ser Val Ser Gly Leu Gly Cys Asn Arg Ile Met Gln Asn Pro
            20                  25                  30

Pro Lys Lys Phe Ser Gly Glu
        35
```

```
<210> SEQ ID NO 173
<211> LENGTH: 39
<212> TYPE: PRT
<213> ORGANISM: Artificial sequence
<220> FEATURE:
<223> OTHER INFORMATION: A portion of a natriuretic peptide

<400> SEQUENCE: 173

Ser Asp Ser Lys Ile Gly Asn Gly Cys Phe Gly Leu Pro Leu Asp Arg
1               5                   10                  15

Ile Gly Ser Val Ser Gly Leu Gly Cys Asn Arg Ile Met Gln Asn Pro
            20                  25                  30

Pro Lys Lys Phe Ser Gly Glu
        35

<210> SEQ ID NO 174
<211> LENGTH: 39
<212> TYPE: PRT
<213> ORGANISM: Artificial sequence
<220> FEATURE:
<223> OTHER INFORMATION: A portion of a natriuretic peptide

<400> SEQUENCE: 174

Ser Asp Ser Lys Ile Gly Asn Gly Cys Phe Gly Phe Pro Leu Asp Arg
1               5                   10                  15

Ile Gly Ser Leu Ser Gly Leu Gly Cys Asn Arg Ile Met Gln Asn Pro
            20                  25                  30

Pro Lys Lys Phe Ser Gly Glu
        35

<210> SEQ ID NO 175
<211> LENGTH: 39
<212> TYPE: PRT
<213> ORGANISM: Artificial sequence
<220> FEATURE:
<223> OTHER INFORMATION: A portion of a natriuretic peptide

<400> SEQUENCE: 175

Ser Asp Ser Lys Ile Gly Asn Gly Cys Phe Gly Phe Pro Leu Asp Arg
1               5                   10                  15

Ile Gly Ser Val Ser Gly Leu Gly Cys Asn Leu Ile Met Gln Asn Pro
            20                  25                  30

Pro Lys Lys Phe Ser Gly Glu
        35

<210> SEQ ID NO 176
<211> LENGTH: 39
<212> TYPE: PRT
<213> ORGANISM: Artificial sequence
<220> FEATURE:
<223> OTHER INFORMATION: A portion of a natriuretic peptide

<400> SEQUENCE: 176

Ser Asp Ser Lys Ile Gly Asn Gly Cys Phe Gly Phe Pro Leu Asp Arg
1               5                   10                  15

Ile Gly Ser Val Ser Gly Leu Gly Cys Asn Arg Leu Met Gln Asn Pro
            20                  25                  30

Pro Lys Lys Phe Ser Gly Glu
        35

<210> SEQ ID NO 177
<211> LENGTH: 39
<212> TYPE: PRT
<213> ORGANISM: Artificial sequence
```

```
<220> FEATURE:
<223> OTHER INFORMATION: A portion of a natriuretic peptide

<400> SEQUENCE: 177

Ser Asp Ser Lys Ile Gly Asn Gly Cys Phe Gly Phe Pro Leu Asp Arg
1               5                   10                  15

Ile Gly Ser Val Ser Gly Leu Gly Cys Asn Arg Ile Leu Gln Asn Pro
            20                  25                  30

Pro Lys Lys Phe Ser Gly Glu
        35

<210> SEQ ID NO 178
<211> LENGTH: 39
<212> TYPE: PRT
<213> ORGANISM: Artificial sequence
<220> FEATURE:
<223> OTHER INFORMATION: A portion of a natriuretic peptide

<400> SEQUENCE: 178

Ser Asp Ser Lys Ile Gly Asn Gly Cys Phe Gly Phe Pro Leu Asp Arg
1               5                   10                  15

Ile Gly Ser Val Ser Gly Leu Gly Cys Asn Arg Ile Met Leu Asn Pro
            20                  25                  30

Pro Lys Lys Phe Ser Gly Glu
        35

<210> SEQ ID NO 179
<211> LENGTH: 39
<212> TYPE: PRT
<213> ORGANISM: Artificial sequence
<220> FEATURE:
<223> OTHER INFORMATION: A portion of a natriuretic peptide

<400> SEQUENCE: 179

Ser Asp Ser Lys Ile Gly Asn Gly Cys Phe Gly Phe Pro Leu Asp Arg
1               5                   10                  15

Ile Gly Ser Val Ser Gly Leu Gly Cys Asn Arg Ile Met Gln Asn Pro
            20                  25                  30

Pro Lys Lys Leu Ser Gly Glu
        35

<210> SEQ ID NO 180
<211> LENGTH: 39
<212> TYPE: PRT
<213> ORGANISM: Artificial sequence
<220> FEATURE:
<223> OTHER INFORMATION: A portion of a natriuretic peptide

<400> SEQUENCE: 180

Ser Asp Ser Lys Ile Gly Asn Gly Cys Phe Gly Phe Pro Leu Asp Arg
1               5                   10                  15

Leu Gly Ser Val Ser Gly Leu Gly Cys Asn Arg Ile Met Gln Asn Pro
            20                  25                  30

Pro Lys Lys Phe Ser Gly Glu
        35

<210> SEQ ID NO 181
<211> LENGTH: 39
<212> TYPE: PRT
<213> ORGANISM: Artificial sequence
<220> FEATURE:
<223> OTHER INFORMATION: A portion of a natriuretic peptide

<400> SEQUENCE: 181
```

Ser Asp Ser Lys Ile Gly Asn Gly Cys Phe Gly Arg Pro Leu Asp Arg
1               5                   10                  15

Ile Gly Ser Val Ser Gly Leu Gly Cys Asn Arg Ile Met Gln Asn Pro
            20                  25                  30

Pro Lys Lys Phe Ser Gly Glu
        35

<210> SEQ ID NO 182
<211> LENGTH: 39
<212> TYPE: PRT
<213> ORGANISM: Artificial sequence
<220> FEATURE:
<223> OTHER INFORMATION: A portion of a natriuretic peptide

<400> SEQUENCE: 182

Ser Asp Ser Lys Ile Gly Asn Gly Cys Phe Gly Phe Lys Leu Asp Arg
1               5                   10                  15

Ile Gly Ser Val Ser Gly Leu Gly Cys Asn Arg Ile Met Gln Asn Pro
            20                  25                  30

Pro Lys Lys Phe Ser Gly Glu
        35

<210> SEQ ID NO 183
<211> LENGTH: 39
<212> TYPE: PRT
<213> ORGANISM: Artificial sequence
<220> FEATURE:
<223> OTHER INFORMATION: A portion of a natriuretic peptide

<400> SEQUENCE: 183

Ser Asp Ser Lys Ile Gly Asn Gly Cys Phe Gly Phe Arg Leu Asp Arg
1               5                   10                  15

Ile Gly Ser Val Ser Gly Leu Gly Cys Asn Arg Ile Met Gln Asn Pro
            20                  25                  30

Pro Lys Lys Phe Ser Gly Glu
        35

<210> SEQ ID NO 184
<211> LENGTH: 39
<212> TYPE: PRT
<213> ORGANISM: Artificial sequence
<220> FEATURE:
<223> OTHER INFORMATION: A portion of a natriuretic peptide

<400> SEQUENCE: 184

Ser Asp Ser Lys Ile Gly Asn Gly Cys Phe Gly Phe Pro Leu Asp Arg
1               5                   10                  15

Ile Arg Ser Val Ser Gly Leu Gly Cys Asn Arg Ile Met Gln Asn Pro
            20                  25                  30

Pro Lys Lys Phe Ser Gly Glu
        35

<210> SEQ ID NO 185
<211> LENGTH: 39
<212> TYPE: PRT
<213> ORGANISM: Artificial sequence
<220> FEATURE:
<223> OTHER INFORMATION: A portion of a natriuretic peptide
<220> FEATURE:
<221> NAME/KEY: MISC_FEATURE
<222> LOCATION: (9)..(9)
<223> OTHER INFORMATION: Xaa=Selenocysteine
<220> FEATURE:
<221> NAME/KEY: MISC_FEATURE

```
<222> LOCATION: (25)..(25)
<223> OTHER INFORMATION: Xaa=Selenocysteine

<400> SEQUENCE: 185

Ser Asp Ser Lys Ile Gly Ala Gly Xaa Phe Gly Phe Pro Leu Asp Arg
1               5                   10                  15

Ile Arg Ser Val Ser Gly Leu Gly Xaa Asn Arg Ile Asn Gln Asn Pro
            20                  25                  30

Pro Lys Lys Phe Ser Gly Glu
        35

<210> SEQ ID NO 186
<211> LENGTH: 39
<212> TYPE: PRT
<213> ORGANISM: Artificial sequence
<220> FEATURE:
<223> OTHER INFORMATION: A portion of a natriuretic peptide
<220> FEATURE:
<221> NAME/KEY: MISC_FEATURE
<222> LOCATION: (9)..(9)
<223> OTHER INFORMATION: Xaa=Selenocystein
<220> FEATURE:
<221> NAME/KEY: MISC_FEATURE
<222> LOCATION: (25)..(25)
<223> OTHER INFORMATION: Xaa=Selenocystein

<400> SEQUENCE: 186

Ser Asp Ser Lys Ile Gly Ala Gly Xaa Phe Gly Phe Pro Leu Asp Arg
1               5                   10                  15

Ile Arg Ser Val Ser Gly Leu Gly Xaa Asn Arg Ile Asn Gln Ala Pro
            20                  25                  30

Pro Lys Lys Phe Ser Gly Glu
        35

<210> SEQ ID NO 187
<211> LENGTH: 41
<212> TYPE: PRT
<213> ORGANISM: Artificial sequence
<220> FEATURE:
<223> OTHER INFORMATION: A portion of a natriuretic peptide

<400> SEQUENCE: 187

Ser Asp Ser Lys Ile Gly Asn Gly Cys Cys His Ala Gly Phe Pro Leu
1               5                   10                  15

Asp Arg Ile Gly Ser Val Ser Gly Leu Gly Cys Asn Arg Ile Met Gln
            20                  25                  30

Asn Pro Pro Lys Lys Phe Ser Gly Glu
        35                  40

<210> SEQ ID NO 188
<211> LENGTH: 39
<212> TYPE: PRT
<213> ORGANISM: Artificial sequence
<220> FEATURE:
<223> OTHER INFORMATION: A portion of a natriuretic peptide

<400> SEQUENCE: 188

Ser Asp Ser Lys Ile Ser Ala Gly Cys Phe Gly Phe Pro Leu Asp Arg
1               5                   10                  15

Ile Gly Ser Val Ser Gly Leu Gly Cys Asn Arg Ile Met Gln Asn Pro
            20                  25                  30

Pro Lys Lys Phe Ser Gly Glu
        35
```

```
<210> SEQ ID NO 189
<211> LENGTH: 26
<212> TYPE: PRT
<213> ORGANISM: Artificial sequence
<220> FEATURE:
<223> OTHER INFORMATION: A portion of a natriuretic peptide

<400> SEQUENCE: 189

Ser Pro Lys Met Val Gln Gly Ser Gly Cys Phe Gly Arg Lys Met Asp
1               5                   10                  15

Arg Ile Ser Ser Ser Ser Gly Leu Gly Cys
            20                  25

<210> SEQ ID NO 190
<211> LENGTH: 32
<212> TYPE: PRT
<213> ORGANISM: Artificial sequence
<220> FEATURE:
<223> OTHER INFORMATION: A portion of a natriuretic peptide

<400> SEQUENCE: 190

Ile Gln Glu Arg Leu Arg Asn Ser Lys Met Ala His Ser Ser Ser Cys
1               5                   10                  15

Phe Gly Gln Lys Ile Asp Arg Ile Gly Ala Val Ser Arg Leu Gly Cys
            20                  25                  30

<210> SEQ ID NO 191
<211> LENGTH: 23
<212> TYPE: PRT
<213> ORGANISM: Artificial sequence
<220> FEATURE:
<223> OTHER INFORMATION: A portion of a natriuretic peptide

<400> SEQUENCE: 191

Glu Val Lys Tyr Asp Pro Cys Phe Gly His Lys Ile Asp Arg Ile Asn
1               5                   10                  15

His Val Ser Asn Leu Gly Cys
            20

<210> SEQ ID NO 192
<211> LENGTH: 30
<212> TYPE: PRT
<213> ORGANISM: Artificial sequence
<220> FEATURE:
<223> OTHER INFORMATION: A portion of a natriuretic peptide

<400> SEQUENCE: 192

Gly Asp Asn Lys Pro Pro Lys Lys Gly Pro Asn Gly Cys Phe Gly
1               5                   10                  15

His Lys Ile Asp Arg Ile Gly Ser His Ser Gly Leu Gly Cys
            20                  25                  30

<210> SEQ ID NO 193
<211> LENGTH: 39
<212> TYPE: PRT
<213> ORGANISM: Artificial sequence
<220> FEATURE:
<223> OTHER INFORMATION: A portion of a natriuretic peptide

<400> SEQUENCE: 193

Ser Asp Ser Lys Ile Gly Asn Gly Cys Phe Gly Ala Lys Ile Asp Arg
1               5                   10                  15

Ile Asn His Val Ser Asn Leu Gly Cys Asn Arg Ile Met Gln Asn Pro
            20                  25                  30

Pro Lys Lys Phe Ser Gly Glu
```

<210> SEQ ID NO 194
<211> LENGTH: 39
<212> TYPE: PRT
<213> ORGANISM: Artificial sequence
<220> FEATURE:
<223> OTHER INFORMATION: A portion of a natriuretic peptide

<400> SEQUENCE: 194

Ser Asp Ser Lys Ile Gly Asn Gly Cys Phe Gly His Lys Ile Asp Arg
1               5                   10                  15

Ile Asn His Ala Ser Asn Leu Gly Cys Asn Arg Ile Met Gln Asn Pro
            20                  25                  30

Pro Lys Lys Phe Ser Gly Glu
        35

<210> SEQ ID NO 195
<211> LENGTH: 39
<212> TYPE: PRT
<213> ORGANISM: Artificial sequence
<220> FEATURE:
<223> OTHER INFORMATION: A portion of a natriuretic peptide

<400> SEQUENCE: 195

Ser Asp Ser Lys Ile Gly Asn Gly Cys Phe Gly His Lys Ile Asp Arg
1               5                   10                  15

Ile Asn His Val Ser Gly Leu Gly Cys Asn Arg Ile Met Gln Asn Pro
            20                  25                  30

Pro Lys Lys Phe Ser Gly Glu
        35

<210> SEQ ID NO 196
<211> LENGTH: 39
<212> TYPE: PRT
<213> ORGANISM: Artificial sequence
<220> FEATURE:
<223> OTHER INFORMATION: A portion of a natriuretic peptide

<400> SEQUENCE: 196

Ser Asp Ser Lys Ile Gly Asn Gly Cys Phe Gly Arg Lys Ile Asp Arg
1               5                   10                  15

Ile Asn His Val Ser Asn Leu Gly Cys Asn Arg Ile Met Gln Asn Pro
            20                  25                  30

Pro Lys Lys Phe Ser Gly Glu
        35

<210> SEQ ID NO 197
<211> LENGTH: 23
<212> TYPE: PRT
<213> ORGANISM: Artificial sequence
<220> FEATURE:
<223> OTHER INFORMATION: A portion of a natriuretic peptide

<400> SEQUENCE: 197

Ser Leu Arg Arg Ser Ser Cys Phe Gly Gly Arg Met Asp Arg Ile Gly
1               5                   10                  15

Ala Gln Ser Gly Leu Gly Cys
            20

<210> SEQ ID NO 198
<211> LENGTH: 23
<212> TYPE: PRT
<213> ORGANISM: Artificial sequence

```
<220> FEATURE:
<223> OTHER INFORMATION: A portion of a natriuretic peptide

<400> SEQUENCE: 198

Ser Leu Arg Arg Ser Ser Cys Phe Gly Gly Arg Ile Asp Arg Ile Gly
1               5                   10                  15

Ala Gln Ser Gly Leu Gly Cys
            20

<210> SEQ ID NO 199
<211> LENGTH: 17
<212> TYPE: PRT
<213> ORGANISM: Artificial Sequence
<220> FEATURE:
<223> OTHER INFORMATION: A portion of a natriuretic peptide

<400> SEQUENCE: 199

Cys Phe Gly Phe Pro Met Asp Arg Ile Gly Ser Val Ser Gly Leu Gly
1               5                   10                  15

Cys

<210> SEQ ID NO 200
<211> LENGTH: 17
<212> TYPE: PRT
<213> ORGANISM: Artificial Sequence
<220> FEATURE:
<223> OTHER INFORMATION: A portion of a natriuretic peptide

<400> SEQUENCE: 200

Cys Phe Gly Phe Pro Leu Asp Arg Ile Asn Ser Val Ser Gly Leu Gly
1               5                   10                  15

Cys

<210> SEQ ID NO 201
<211> LENGTH: 17
<212> TYPE: PRT
<213> ORGANISM: Artificial Sequence
<220> FEATURE:
<223> OTHER INFORMATION: A portion of a natriuretic peptide

<400> SEQUENCE: 201

Cys Phe Gly Phe Pro Leu Asp Arg Ile Gly His Val Ser Gly Leu Gly
1               5                   10                  15

Cys

<210> SEQ ID NO 202
<211> LENGTH: 8
<212> TYPE: PRT
<213> ORGANISM: Artificial Sequence
<220> FEATURE:
<223> OTHER INFORMATION: A portion of a natriuretic peptide
<220> FEATURE:
<221> NAME/KEY: misc_feature
<222> LOCATION: (3)
<223> OTHER INFORMATION: Xaa is Ser, Ala, Thr, Gly or Pro
<220> FEATURE:
<221> NAME/KEY: misc_feature
<222> LOCATION: (7)
<223> OTHER INFORMATION: Xaa is Asp, Asn, Gln or Ser

<400> SEQUENCE: 202

Ser Asp Xaa Lys Ile Gly Xaa Gly
1               5

<210> SEQ ID NO 203
<211> LENGTH: 17
```

```
<212> TYPE: PRT
<213> ORGANISM: Artificial Sequence
<220> FEATURE:
<223> OTHER INFORMATION: A portion of a natriuretic peptide
<220> FEATURE:
<221> NAME/KEY: misc_feature
<222> LOCATION: (4)
<223> OTHER INFORMATION: Xaa is Gly, Ser, Ala, Thr, Pro, Tyr, Val, Ile,
      Leu, Met, Phe, Trp, Arg, Lys, His or modified forms thereof
<220> FEATURE:
<221> NAME/KEY: misc_feature
<222> LOCATION: (5)
<223> OTHER INFORMATION: Xaa is Arg, Lys, His or modified forms thereof
<220> FEATURE:
<221> NAME/KEY: misc_feature
<222> LOCATION: (6)
<223> OTHER INFORMATION: Xaa is Tyr, Val, Ile, Leu, Met, Phe, Trp or
      modified forms thereof
<220> FEATURE:
<221> NAME/KEY: misc_feature
<222> LOCATION: (10)
<223> OTHER INFORMATION: Xaa is Gly, Ser, Ala, Thr, Pro, Asn, His, Gln,
      Cys, Ser, Thr or modified forms thereof
<220> FEATURE:
<221> NAME/KEY: misc_feature
<222> LOCATION: (11)
<223> OTHER INFORMATION: Xaa is Gly, Ser, Ala, Thr, Pro, Asg, Lys, His
      or modified forms thereof
<220> FEATURE:
<221> NAME/KEY: misc_feature
<222> LOCATION: (12)
<223> OTHER INFORMATION: Xaa is Gly, Ser, Ala, Thr, Pro, Tyr, Val, Ile,
      Leu, Met, Phe, Trp, Asn, His, Gln, Cys or modified forms thereof
<220> FEATURE:
<221> NAME/KEY: misc_feature
<222> LOCATION: (14)
<223> OTHER INFORMATION: Xaa is Gly, Ser, Ala, Thr, Pro, Asn, His, Gln,
      Cys or modified forms thereof

<400> SEQUENCE: 203

Cys Phe Gly Xaa Xaa Xaa Asp Arg Ile Xaa Xaa Xaa Ser Xaa Leu Gly Cys
1               5                   10                  15

<210> SEQ ID NO 204
<211> LENGTH: 10
<212> TYPE: PRT
<213> ORGANISM: Artificial Sequence
<220> FEATURE:
<223> OTHER INFORMATION: A portion of a natriuretic peptide
<220> FEATURE:
<221> NAME/KEY: misc_feature
<222> LOCATION: (3)
<223> OTHER INFORMATION: Xaa is Ser, Pro, Ile, Leu or Phe
<220> FEATURE:
<221> NAME/KEY: misc_feature
<222> LOCATION: (4)
<223> OTHER INFORMATION: Xaa is Tyr, Val, Leu, Met or modified forms
      thereof
<220> FEATURE:
<221> NAME/KEY: misc_feature
<222> LOCATION: (7)
<223> OTHER INFORMATION: Xaa is Arg, His, Ser, Pro or modified forms
      thereof

<400> SEQUENCE: 204

Asn Arg Xaa Xaa Gln Asn Xaa Pro Lys Lys
1               5                   10
```

CHIMERIC PROTEINS WITH NATRIURETIC ACTIVITY

RELATED APPLICATIONS

This application is a continuation-in-part of International Application No. PCT/AU2005/001047, filed Jul. 15, 2005 and published in English, the U.S. designation of which is a non-provisional application of U.S. Provisional Application No. 60/588,243, filed Jul. 15, 2004, the entire contents of each and all these applications being hereby incorporated by reference herein in their entirety as if fully disclosed herein.

REFERENCE TO SEQUENCE LISTING

The present application incorporates by reference the sequence listing submitted as an ASCII text filed via EFS-Web on Apr. 12, 2011. The Sequence Listing is provided as a file entitled 11025066_1.txt, created on Apr. 12, 2011, which is 74.7 Kb in size.

FIELD OF THE INVENTION

This invention relates generally to proteinaceous compounds and more particularly to proteinaceous compounds that comprise at least a biologically active portion of a taipan natriuretic peptide (TNP) or a variant or derivative thereof. The invention also relates to the use of these compounds in methods for stimulating vasodilation, natriuresis, diuresis, renin-suppression, bactericidal activity, weight-loss or bone growth in a mammalian host. In specific embodiments, the compounds of the present invention are useful in the treatment of congestive heart failure.

BACKGROUND OF THE INVENTION

Natriuretic peptides (NPs) are known for their role in cardiovascular homeostasis, diuresis, natriuresis and vasodilation. They act in the body to oppose the activity of the renin-angiotensin system and enhance excretion of sodium and water. There are four known types of natriuretic peptides in humans: atrial natriuretic peptide (ANP), brain natriuretic peptide (BNP), S-type natriuretic peptide (CNP) and dendroaspis natriuretic peptide (DNP). Isoforms of these occur in nature across species.

ANP is secreted by atrial myocytes in response to increased intravascular volume. Once it is in the circulation, its effects are primarily on the kidney, vascular tissue and adrenal gland, in which its actions lead to the excretion of sodium and water by the kidneys and a decrease in intravascular volume and blood pressure (Atlas et al., 1987, *In Atrial Hormones and Other Natriuretic Factors*, P. J. Mulrow et al., Eds, *Am. Physiol. Soc.*, Bethesda, Md., pp. 53-76).

BNP is of myocardial cell origin and, like ANP, circulates in human plasma (de Bold et al., 1981, *Life Science*, 28(1): 89-94; Burnett et al., 1986, *Science*, 231(4742): 1145-1147). BNP is natriuretic, renin-inhibiting, vasodilating and lusitropic (Mukoyama et al., 1991, *J. Clin. Invest.*, 87(4): 1402-1412; Yamamoto et al., 1996, *Am. J. Physiol.*, 271(6 Pt 2):R1529-1534; Grantham et al., 1997, *Natriuretic Peptides in Health and Disease*, Samson W. K. 11e.r., eds, Humana Press, pp. 309-326).

CNP is of endothelial cell origin and functions as a vasodilating and growth-inhibiting peptide (Suga et al., 1992, *J. Clin. Invest.*, 90(3): 1145-1149; Stingo et al., 1992, *Am. J. Physiol.*, 262(1 Pt 2):H308-312; Koller et al., 1991, *Science*, 252(5002): 120-123).

DNP possesses structural similarity to ANP, BNP and CNP. It was originally found in the venom of *Dendroaspis angusticeps* and has been shown to vasorelax rodent aorta and isolated canine coronary arteries with potency comparable to that of ANP (Schweitz et al., 1992, *J. Biol. Chem.*, 267: 13928-13932; Wenberg et al., 1997, *Am. Coll. Cardiol.*, 29: 305a). Recently DNP immunoreactivity has been demonstrated in human circulation, and its plasma levels are elevated in congestive heart failure (CHF) (Schirger et al., 1999, *Mayo Clin. Proc.*, 74: 126-130). A NP-like peptide, Lebetin 2 isoform alpha, was found in the venom of *Vipera lepitera* (Barbouche et al., 1996, *FEBS Lett.* 392:6-10). This peptide contains the consensus natriuretic peptide signature which indicates that it belongs to the same general family. Illustrative examples of known natriuretic peptides are given in Table 1.

Natriuretic peptides effect their biological role through three receptors: NPR-A, NPR-B and NPR-C. NPR-A and NPR-B have cytoplasmic guanylyl cyclase domains, which are activated upon ligand binding and lead to accumulation of intracellular cGMP. The tissue distribution of each receptor is different. While NPR-A is expressed in vasculature, kidney and adrenal glands, NPR-B is mainly expressed in the brain. NPR-C, is devoid of the kinase and cytoplasmic GC domains and is generally considered to be a clearance receptor for removing natriuretic peptides from the circulation, although other biological functions for it have been postulated (Murthy et al., 1999, *J. Biol. Chem.*, 274(25): 17587-17592). U.S. Pat. Nos. 5,846,932 and 6,028,055 disclose potent ANP and BNP variants having decreased affinity for the human clearance or C-receptor (NPR-C). DNP has been shown to produce relaxation through both the NPR-A and NPR-C receptors.

ANP and BNP each bind to both NPR-A and NPR-C with high affinity, but only bind to NPR-B with low affinity, whereas CNP binds to NPR-B and NPR-C, but not appreciably to NPR-A (Potter L R and Hunter T, 2001, *J. Biol. Chem.* 276: 6057-6060). It is generally considered that the beneficial effects (natriuresis/diuresis or effects on renin/angiotensin system) of natriuretic peptides occur via the synthesis of the intracellular messenger cyclic-GMP (cGMP). NPRA is thought to be the primary ANP/BNP signaling molecule and has been suggested as the principal mediator of natriuretic peptide activities. Conclusive studies have determined that NPR-A is the only NP binding receptor that regulates natriuresis/diuresis and regulates the renin/angiotensin system (Kishimoto I, et al., 1996, *Proc Natl Acad Sci USA* 93: 6215-6219). In this study it was demonstrated that ANP does not bind to tissues from animals that are homozygous null mutants for NPR-A. These animals do not undergo natriuresis or diuresis in response to ANP and their aortic rings do not relax in response to that peptide. Shi et al. (2003, AJP—Renal 285:694-702) established that NPRA is critical in mediating the natriuresis, diuresis, and renal hemodynamic responses to acute blood volume expansion. From these studies it is apparent that, for a NP peptide to be of use in the treatment of CHF, it must act at the NPR-A receptor.

The ability for a NP to bind human NPR-A cannot be predicted from an analysis of primary sequence alone, nor can analysis of primary sequence predict the affinity with which a NP can bind to NPR-A. The sequences of both the hormones and their receptors vary across species. A consensus NP sequence has been identified for NPs but this is loosely defined and provides no information on whether the peptide acts as an NP, and no guidance as to whether the peptide is active at NPR-A in particular (and hence potentially useful for treating CHF), NPR-B and/or NPR-C. Schweitz et al. (1992 *J. Biol. Chem.* 267: 13928-13932) identified DNP as a ligand for NPR-A on the basis that the peptide relaxes aortic rings. In an early attempt to define features important for NPR-A binding, they proposed a conservative tripeptide sequence in the C-terminal part of the as then known natriuretic peptides consisting of (i) a small non-hydrophilic residue; (ii) a large hydrophobic residue and (iii) an arginine residue, as highlighted in FIG. 2. However, as is evident in later studies and in the present specification, this generalization does not hold and provides little guidance as to whether a natriuretic peptide has NPR-A activity, or otherwise.

ANP, BNP, CNP and DNP are synthesized from large precursors and the mature, active peptides have a 17-amino acid ring structure formed by an intramolecular disulfide linkage. In the human peptides, ten of these amino acids are identical, whereas the N-terminal head and C-terminal tail vary in both length and composition (see Kambayashi et al., 1990, *FEBS Lett*, 259: 341-345; Tawaragi et al., 1991, *Biochem. Biophys. Res. Commun.* 175: 645-651).

Due to their diverse actions on both the cardiovascular system and the kidney, ANP, BNP, CNP and DNP and their analogues have been the subject of great interest for developing novel therapeutics. For example, reference may be made to Lewicki et al. (U.S. Pat. Nos. 5,114,923, 4,804,650 and 4,757,048), Johnson et al. (U.S. Pat. No. 5,047,397), Johnson et al. (U.S. Pat. No. 4,935,492), and Wei et al. (U.S. Pat. No. 5,583,108). U.S. Pat. No. 5,583,108 discloses a chimera of ANP and CNP, termed vasonatrin peptide (VNP). VNP, which includes 22 amino acids of CNP and the 5 amino acids at the carboxy-terminus of ANP, has arterial and venous vasodilating and natriuretic effects. U.S. Pat. No. 6,407,211 discloses chimeric compounds comprising the C-terminal tail of DNP with the core ring structure of BNP or CNP.

The above natriuretic peptides and their analogues are known to be useful for treating a variety of different conditions including: edematous states such as congestive heart failure (CHF), nephrotic syndrome and hepatic cirrhosis; hypertension; pulmonary hypertension; and renal disorders as well as diseases such as renal failure due to ineffective renal perfusion or reduced glomerular filtrate rate; bacterial infections; weight loss; asthma; inflammatory-related diseases; erectile dysfunction; hypercholesterolemia; skeletal dysplasias and as a protectant for toxicity of anti-cancer drugs, as described for example in WO 2004/011498.

Typically, heart failure patients receive several chronic oral therapies, primarily including diuretics, angiotensin-converting enzyme (ACE) inhibitors, and beta-blockers. Often, these patients have an acute episode of CHF, requiring hospitalization. Following an acute episode, survivors are required to continue management of the chronic condition. The gold standard for the treatment of more advanced CHF is quadruple therapy with an ACE inhibitor (or an ARB), a beta-blocker, a diuretic and digoxin. However, each of these is associated with a number of deleterious side-effects such as neurohumoral activation, ototoxicity, hypokalemia, renal impairment and an increased risk of arrhythmic death. It has been observed that enhancement of the NP system may provide a better strategy to treat the sodium and water retention that increases cardiac preload leading to progressive cardiac dysfunction in CHF patients (Costello-Boerrigter et al., 2003, *Medical Clinics of North America* 87(2)). The therapeutic potential of the NPs is underscored by the role played by ANP and BNP in overcoming sodium retention in the early phase of CHF. As CHF evolves, the balance between the antinatri-uretic-vasoconstrictive systems (i.e., RAAS, sympathetic nervous system, vasopressin and endothelin) and natriuretic-vasodilatory systems (i.e., NPs, nitrous oxide, prostaglandins and adrenomedulin), which has a profound effect on sodium and water homeostasis, moves towards the former system. The current hypothesis is that there is a state of relative deficiency of NP in CHF. Consequently, enhancement of NPs is considered a beneficial strategy either via administration of exogenous NPs, through agonists of NP-A, or by inhibition of the enzyme responsible for NP degradation, NEP 24.11. In tribute to the growing recognition of NP therapy, nesiritide citrate or Natrecor®, a BNP citrate salt, has been launched commercially for the intravenous treatment of acute CHF patients in the United States. A recombinant form of hANP, termed carperitide, has been launched in Japan for the same indication and is currently in clinical trials in the USA (Pharmaprojects, 2005).

An advantage of NPs over currently used diuretics is that they do not activate the RAAS system (which is associated with the progression of CHF). Furthermore, they inhibit the sympathetic nervous system (which is associated with heart failure progression, myocyte necrosis and apoptosis, and arrhythmias). It has been demonstrated that NPs exhibit fewer arrhythmic events, such as tachycardia. In trials, BNP was reported to be associated with less arrhythmic events than dobutamine (Burger et al., 2001, *Am J Cardiol* 88, 35-39). NPs and their derivatives can be administered alone or in combination with one or more of the following compounds: beta blockers, diuretics, ACE inhibitors, digoxin, spironolactone, anticoagulation and antiplatelet agents and angiotensin receptor blockers, as disclosed for example in WO03081246.

A disadvantage of NPs is that they are notoriously fragile in vivo, being degraded rapidly by neutral endopeptidases (NEPs) and through the clearance receptor (NPR-C), thus limiting their bioavailability. A corollary of this is that NPs, in particular Nesritide, is only useful in the treatment of acute CHF requiring intravenous infusion. To access the chronic CHF market, new stabilized NPs are sought. Such NPs have the requirements of significantly improved half lives so that more convenient routes of administration such as subcutaneous injection or oral administration can be adopted and with less frequent dosing than would be needed for current NP therapies such as ANP or BNP, both which have short half lives.

Attempts to increase resistance to proteolytic degradation of NPs through use of PEGylation and other conjugates (see, for example, WO2004/047871), resulted in improved resistance to trypsin, oral availability and in increased plasma levels as compared to native BNP in some examples. Interestingly, analysis of animal plasma assays for its lead compound reveal that their oral delivery technology is successful, in that the hBNP survives the GI tract and reaches the blood stream. However, once in the blood stream, it is degraded and cleared quite quickly (within 30 minutes the plasma levels of the compound are almost zero), demonstrating no superiority over Natrecor's 18 minute half-life. In short, hBNP is too unstable, and therefore not amenable to oral administration. An alternative approach is bioconjugation of the NP with blood components for example human serum albumin. This technology has been demonstrated to increase NP half life (see, for example, WO 2004011498). However, the corresponding large size of the resulting complex makes it unsuitable for most forms of administration. Additionally, it is not clear that the activated NP does not conjugate to other biological species in vivo with the consequence that regulatory and safety issues may arise. Other studies have targeted the stability of NPs by selecting for analogues that favor the NPR-A receptor over the NPR-C receptor (see, for example U.S. Pat. Nos. 6,028,055 and 5,846,932), thus reducing clearance mechanisms or by stabilizing the sequence against NEP protease digestion, for example by replacing the susceptible Phe with Cha. All these studies demonstrate the general amenability of NPs, without significant loss of activity, to substitution and derivatisation provided that the primary binding moieties are not disturbed.

DNP has been found to possess higher resistance to NEPs than previously known NPs, putatively due to its extended tail region. The tail region is roughly correlated to stability, with CNP, the least stable having the shortest tail. Indeed, the significantly higher potency of BNP over ANP in elevating cGMP levels in mice kidney is attributed to the greater stability of the former peptide. Correspondingly, there still exists a need for compounds with NP-like activity that are better able to withstand proteolytic enzyme attack, particularly that of NEP 24.11.

It is not possible to determine the stability of NP peptides from an examination of their primary sequences alone. The program "Peptide Cutter" available on the suite of protein analysis programs, Swissprot (http://us.expasy.org/sprot/) predicts that all known peptides have multiple regions of susceptibility to proteolytic attack. For instance, ANP is predicted to contain 59 cleavage sites for 12 enzymes, whereas BNP is predicted to contain 55 cleavage sites for a total of 13 enzymes. The peptides of the present invention are predicted to contain 59 cleavage sites for a total of 16 enzymes. Yet, as is demonstrated herein, these latter peptides are significantly more stable than their human counterparts.

SUMMARY OF THE INVENTION

In work leading up to the present invention, the inventors isolated three novel peptides of between 35 and 39 amino acid residues in length from the venom of *Oxyranus microlepidotus* (Inland taipan). The amino acid sequences of these taipan natriuretic peptides (TNPs) (see Table 2) display significant similarity to ANP and BNP within the core structure (i.e., between the cysteine residues) but no similarity at either the N-terminal head or C-terminal tail (see FIG. 2). Of interest, one of these peptides, designated TNPc, contains the consensus natriuretic signature (Table 1), whilst the other two peptides, designated, TNPa and TNPb, differ from the consensus signature by only a single residue, (i.e., both have a His at position 16, whereas the consensus signature has a conservative Arg at the same position), although this is a conservative substitution.

Based upon their structural similarity to mammalian natriuretic peptides, the isolated TNPs were predicted to have at least some of the properties associated with their mammalian homologues (e.g., vasodilatory, natriuretic, diuretic, renin-suppressing, bactericidal, weight-reducing and/or bone growth plate size-increasing activities). However, despite their suspected activities, the TNPs were not considered to be particularly useful in therapeutic or prophylactic applications in mammals because they differed substantially with the known mammalian natriuretic peptides in the N-terminal head and C-terminal tail, and were suspected, therefore, to elicit significant immune responses when administered to mammals. It was proposed that these immune responses would render the snake venom peptides ineffective, especially in the context of chronic administration.

Surprisingly, the inventors have discovered that these TNPs do not produce significant anti-peptide immune responses when administered to mammals and that only TNPc is useful in therapeutic or prophylactic applications. In particular, it was found that TNPc has high affinity for the NPR-A receptor as well as vasodilatory, natriuretic and diuretic properties characteristic of the NP family, with improved in vitro and in vivo stability. By contrast, both TNPa and TNPb were found to have poor activity at the NPR-A receptor as well as insignificant vasodilatory activity, despite their structural similarity to TNPc.

In studies exploring the structure/function relationship of the TNPs, it was found that substitution of Arg 16 or Ile28 in TNPc with His and Pro, respectively, which are found at the same positions in TNPa/b, reduces the activity markedly. These results suggested that the reduced activity of TNPa and TNPb arises, at least in part, by the departure (despite its apparent conservative nature) from the consensus natriuretic signature and the presence of a Pro in the C-terminal tail where a hydrophobic residue is found consistently in other natriuretic peptides.

Since the C-termini of natriuretic peptides are believed to be important for binding to NP receptors, and for stability, the inventors propose that the C-terminus of TNPc as well as its variants and derivatives can be linked to the core structures of other natriuretic peptides to form chimeric compounds with useful profiles of bioactivity. These chimeric compounds may optionally further comprise a N-terminal portion of TNPc or of another natriuretic peptide. The inventors also propose that the N-terminal portion and core ring structure of TNPc and their variants and derivatives can be linked in a similar fashion to the core ring structure and C-terminal portion, respectively, of other natriuretic peptides to form useful chimeric compounds.

Thus, in one aspect, the present invention provides isolated proteinaceous compounds comprising at least one activity selected from vasodilatory, natriuretic, diuretic, renin-suppressing, bactericidal, weight-reducing or bone growth plate size-increasing activities, in vertebrate animals including mammals. The compounds generally comprise the formula:

$$\Delta\text{-}\Theta\text{-}\Omega \tag{I}$$

wherein:
$\Delta$ is absent or is a N-terminal portion of a natriuretic peptide or a variant or derivative of that portion;
$\Theta$ is the core ring structure of a natriuretic peptide or a variant or derivative of the structure;
$\Omega$ is a C-terminal portion of a natriuretic peptide or a variant or derivative of that portion; and
at least one of $\Delta$, $\Theta$ and $\Omega$ comprises a biologically active portion of TNPc or a variant or derivative thereof.

In some embodiments, the biologically active portion comprises a C-terminal portion of TNPc, e.g., NRIMQNPPKK [SEQ ID NO:1], NRIMQNPPKKF [SEQ ID NO:2], NRIMQNPPKKFS [SEQ ID NO:3], NRIMQNPPKKFSG [SEQ ID NO:4] or NRIMQNPPKKFSGE, [SEQ ID NO:5], or a variant or derivative thereof. In other embodiments, the biologically active portion comprises the TNPc core ring structure sequence CFGFPLDRIGSVSGLGC [SEQ ID NO:6], or a variant or derivative thereof. In still other embodiments, the biologically active portion comprises a N-terminal portion of TNPc, e.g., SDSKIGNG [SEQ ID NO:7], or a variant or derivative thereof.

In certain embodiments, the variant or derivative of the biologically active portion of TNPc comprises a sequence having at least 80, 85, 90, 96, 97, 98 or 99% sequence similarity with, or differs at no more than 1, 2, 3, 4, 5 or 10 amino acid residues from, the corresponding portion represented by any one of SEQ ID NO:1-7, with the proviso that: (a) when the variant or derivative corresponds to a C-terminal portion of TNPc, it comprises a hydrophobic amino acid residue, e.g., I, L or F, at position 28 relative to the amino acid sequence of TNPc; and (b) when the variant or derivative corresponds to the core ring structure of TNPc, it comprises a basic amino acid residue, e.g., R or K at position 16 relative to the amino acid sequence of TNPc.

In specific embodiments, the variant or derivative of the biologically active portion of TNPc shares at least 90% sequence identity with any one of SEQ ID NO:1-7.

When $\Delta$, $\Theta$ or $\Omega$ comprise a biologically active portion of a natriuretic peptide other than TNPc or its variants or derivatives, the natriuretic peptide is suitably selected from ANP, BNP, CNP, DNP, VNP, PNP or an *Oxyuranus* natriuretic peptide such as a natriuretic peptide from *Oxyuranus microlepidotus*, other than TNPc, or its variants or derivatives.

In some embodiments, the compounds generally comprise the formula:

$$\Delta_1\text{-}\Theta_1\text{-}\Omega_1 \tag{II}$$

wherein:
$\Delta_1$ is absent or is a N-terminal portion of a natriuretic peptide or a variant or derivative of the portion;

Θ₁ is the core ring structure of a natriuretic peptide or a variant or derivative of the structure; and Ω₁ is a C-terminal portion comprising an amino acid sequence having the formula:

$$X_1X_2\Phi_1X_3X_4X_5X_6\Sigma_1X_7X_8\Lambda \qquad (III)$$

wherein:

$X_{1-8}$ are independently selected from any amino acid residue, or modified form thereof;

$\Phi_1$ is selected from any hydrophobic amino acid residue, or modified form thereof; and $\Sigma_1$ is a small amino acid residue, or modified form thereof; and Λ is absent or is a peptide comprising an amino acid sequence having the formula:

$$X_9\Sigma_2\Sigma_3X_{10}X_{11} \qquad (IV)$$

wherein:

$X_9$ is selected from any amino acid residue, or modified form thereof;

$\Sigma_2$ is absent or is selected from any small amino acid residue, or modified form thereof;

$\Sigma_3$ is absent or is selected from any small amino acid residue, or modified form thereof, when $\Sigma_2$ is present;

$X_{10}$ is selected from any amino acid residue, or modified form thereof, when $\Sigma_3$ is present; and $X_{11}$ is selected from any amino acid residue, or modified form thereof, when $X_{10}$ is present, with the proviso that formula III excludes:

```
NSFRY [SEQ ID NO: 8] when Δ₁-Θ₁ consists of
                                    [SEQ ID NO: 197]
SLRRSSCFGGRMDRIGAQSGLGC;

NSFRYRR [SEQ ID NO: 9] when Δ₁-Θ₁ consists of
                                    [SEQ ID NO: 198]
SLRRSSCFGGRIDRIGAQSGLGC;

KVLRRH [SEQ ID NO: 10] when Δ₁-Θ₁ consists of
                                    [SEQ ID NO: 189]
SPKMVQGSGCFGRKMDRISSSSGLGC;

DGLRLF [SEQ ID NO: 11] when Δ₁-Θ₁ consists of
                                    [SEQ ID NO: 190]
IQERLRNSKMAHSSSCFGQKIDRIGAVSRLGC;

PSLRDPRPNAPSTSA [SEQ ID NO: 12] when Δ₁-Θ₁
consists of
                                    [SEQ ID NO: 191]
EVKYDPCFGHKIDRINHVSNLGC;
and NKVDDNKG [SEQ ID NO: 13] when Δ₁-Θ₁ consists of
                                    [SEQ ID NO: 192]
GDNKPPKKGPPNGCFGHKIDRIGSHSGLGC.
```

In some embodiments, $X_1$ is selected from a basic amino acid residue, e.g., K, a neutral/polar amino acid residue, especially a polar/large amino acid residue, e.g., N, or a small amino acid residue, e.g., N, or modified form thereof. In some embodiments, $X_2$ is selected from a hydrophobic amino acid residue, e.g., V, a basic amino acid residue, e.g., R, or a small amino acid residue, e.g., S, or modified form thereof. In some embodiments, $\Phi_1$ is an amino acid residue that comprises an aliphatic side chain, e.g., I or L, or an aromatic side chain, e.g., F, or modified form thereof. In some embodiments, $X_3$ is selected from a basic amino acid residue, e.g., R, or a hydrophobic amino acid residue, e.g., M or V, or modified form thereof. In some embodiments, $X_4$ is selected from a neutral/polar, especially a polar/large amino acid residue, e.g., Q, a basic amino acid residue, e.g., R, a hydrophobic amino acid residue, especially one with an aromatic side chain, e.g., Y or an acidic amino acid residue, e.g., D, or modified form thereof. In some embodiments, $X_5$ is selected from a neutral/polar, especially a polar/large, amino acid residue, e.g., Q or N, a basic amino acid residue, e.g., H, or a small amino acid residue, e.g., A or P, or modified form thereof. In some embodiments, $X_6$ is selected from a basic amino acid residue, e.g., R, or a small amino acid residue, e.g., P, or modified form thereof. In some embodiments, $\Sigma_1$ is P, or modified form thereof. In some embodiments, $X_7$ is selected from a basic amino acid residue, e.g., K, or a neutral/polar, especially a polar/large, amino acid residue, e.g., N, or modified form thereof. In some embodiments, $X_8$ is selected from a basic amino acid residue, e.g., K, or a small amino acid residue, e.g., A, or modified form thereof.

In some embodiments, $X_9$ is selected from a hydrophobic amino acid residue, especially one with an aromatic side chain, e.g., F, or a small amino acid residue, e.g., P, or modified form thereof. In some embodiments, $\Sigma_2$ is S, or modified form thereof. In some embodiments, $\Sigma_3$ is selected from G or T, or modified form thereof. In some embodiments, $X_{10}$ is selected from an acidic amino acid residue, e.g., E, or a small amino acid residue, e.g., S, or modified form thereof. In some embodiments, XII is A, or modified form thereof.

In certain embodiments, formula (III) is represented by:

$$\Pi_1\Psi_1\Phi_2\Phi_3\Pi_2\Pi_3X_{12}\Sigma_4\Psi_2\Psi_3\Gamma \qquad (V)$$

wherein:

$\Pi_1, \Pi_2$ and $\Pi_3$ are independently selected from any neutral/polar amino acid residue, or modified form thereof;

$\Psi_1, \Psi_2$ and $\Psi_3$ are independently selected from any basic amino acid residue, or modified form thereof;

$\Phi_2$ and $\Phi_3$ are independently selected from any hydrophobic amino acid residue, or modified form thereof;

$X_{12}$ is selected from any amino acid residue, or modified form thereof;

$\Sigma_4$ is a small amino acid residue, or modified form thereof; and

Γ is absent or is a peptide of 1-10 amino acid residues.

In some embodiments, $\Pi_1$ is a polar/large amino acid residue, e.g., N, or modified form thereof. In some embodiments, $\Psi_1$ is R, or modified form thereof. In some embodiments, $\Phi_2$ is an amino acid residue that comprises an aliphatic side chain, e.g., I or L, or an aromatic side chain, e.g., F, or modified form thereof. In some embodiments, $\Phi_3$ is selected from M, Nle or V, or modified form thereof. In some embodiments, $\Pi_2$ is a polar/large amino acid residue, e.g., Q, or modified form thereof. In some embodiments, $\Pi_3$ is a polar/large amino acid residue, e.g., N, or modified form thereof. In some embodiments, $X_{12}$ is a small or basic amino acid residue, e.g., P or R, or modified form thereof. In some embodiments, $\Sigma_4$ is P, or modified form thereof. In some embodiments, $\Psi_2$ is K, or modified form thereof. In some embodiments, $\Psi_3$ is K, or modified form thereof.

In certain embodiments, $\Pi_1$ is N, or modified form thereof, $\Psi_1$ is R, or modified form thereof, $\Phi_2$ is I, L or F, or modified form thereof, $\Phi_3$ is M or V, or modified form thereof $\Pi_2$ is Q, or modified form thereof, $\Pi_3$ is N, or modified form thereof, $X_{12}$ is selected from R or P, or modified form thereof, $\Sigma_4$ is P, or modified form thereof, and each of $\Psi_2$ and $\Psi_3$ are K or modified form thereof.

In certain embodiments, F is present and comprises the formula:

$$\Phi_4\Sigma_5\Sigma_6\Xi \qquad (VI)$$

wherein:

$\Phi_4$ is a hydrophobic amino acid residue, e.g., comprising an aromatic side chain such as but not limited to F;

$\Sigma_5$ is small amino acid residue, e.g., S, or modified form thereof;

$\Sigma_6$ is small amino acid residue, e.g., G, or modified form thereof; and

Ξ is an acidic amino acid residue, e.g., E, or modified form thereof.

Suitably, formula (VI) is represented by the sequence FSGE [SEQ ID NO:14] or a variant or derivative thereof.

Illustrative examples of C-terminal portions (i.e., $\Omega_1$) include: NRIVQNRPKK [SEQ ID NO:15]; NRLVQNRPKK [SEQ ID NO:16]; NRIMQNPPKKFSGE [SEQ ID NO:17]; NRFMQNRPKKFSGE [SEQ ID NO:18]; NRILQNPPKKFSGE [SEQ ID NO:19]; NRPMNNPPKKFSGE [SEQ ID NO:20]; NRIVQNPPKKFSGE [SEQ ID NO:21]; NRIMQNRPKKFSGE [SEQ ID NO:22]; KRIMQNPPKKFSGE [SEQ ID NO:23]; NSIMQNPPKKFSGE [SEQ ID NO:24]; NRLMQNPPKKFSGE [SEQ ID NO:25]; NRFMQNPPKKFSGE [SEQ ID NO:26]; KRIVQNPPKKFSGE [SEQ ID NO:27]; NRIMQQPPKKFSGE [SEQ ID NO:28]; NRInQNPPKKFSGE [SEQ ID NO:29]; NRIMQAPPKKFSGE [SEQ ID NO:30]; NRLMQQPPKKFSGE [SEQ ID NO:31]; NRIMQAOPKKFSGE [SEQ ID NO:32]; NRIMQQOPKKFSGE [SEQ ID NO:33]; NRIMQNPPKKFSGE [SEQ ID NO:34]; NRInQAPPKKFSGE [SEQ ID NO:35]; NRVnQAPPKKFSGE [SEQ ID NO:36]; NRIMQNRPKKFSGE [SEQ ID NO:37]; NRVMQNPPKKFSGE [SEQ ID NO:38]; NRIMQQRPKKFSGE [SEQ ID NO:39]; KRIMQNPPKKFSGE [SEQ ID NO:40]; NRIMRQPPKKFSGE [SEQ ID NO:41]; NRVMRQPPKKFSGE [SEQ ID NO:42]; NRIMQNPPKKFSTE [SEQ ID NO:43]; PSLRDPRPNAPSTSA [SEQ ID NO:44]; PVLRDPRPNAPSTSA [SEQ ID NO:45]; NRLVQNPPKKFSGE [SEQ ID NO:46]; NRIMQNRPKKFSGE [SEQ ID NO:47]; and PRLRDPRPNAPSTSA [SEQ ID NO:48].

Suitably, $\Delta_1$ and $\Theta_1$ are independently selected from N-terminal portions and core structures, respectively, of natriuretic peptides selected from ANP, BNP, CNP, DNP, VNP, PNP or an *Oxyuranus* natriuretic peptide such as a natriuretic peptide from *Oxyuranus microlepidotus*, or their variants or derivatives.

In certain embodiments, $\Delta_1$ is present and is represented by the formula:

$$O\Sigma_1 \Theta X_1 X_2 X_3 X_4 X_5 \Sigma_2 \quad (VII)$$

wherein:
O is absent or is a peptide of 1-10 amino acid residues;
$\Sigma_{1-2}$ are independently selected from any small amino acid residue, or modified form thereof;
Θ is selected from any charged amino acid residue, or modified form thereof; and
$X_{1-5}$ are independently selected from any amino acid residue, or modified form thereof.

In some embodiments, O is selected from a small amino acid residue, e.g., S, or modified form thereof, or a protecting moiety. In some embodiments, $\Sigma_1$ is selected from P or S, or modified form thereof. In some embodiments, Θ is selected from an acidic amino acid residue, e.g., D, or a basic amino acid residue, e.g., K, or modified form thereof. In some embodiments, $X_1$ is selected from a hydrophobic amino acid residue, e.g., M, a small amino acid residue, e.g., P or S, or an acidic amino acid residue, e.g., E, or modified form thereof. In some embodiments, $X_2$ is selected from a basic amino acid residue, e.g., K, or a hydrophobic amino acid residue, e.g., V or L, or modified form thereof. In some embodiments, $X_3$ is selected from a hydrophobic amino acid residue, e.g., I, a neutral/polar, especially a polar/large, amino acid residue, e.g., Q, or a basic amino acid residue, e.g., R or K, or modified form thereof. In some embodiments, $X_4$ is selected from a small amino acid residue, e.g., G, a basic amino acid residue, e.g., R, or a hydrophobic amino acid residue, especially one with an aromatic side chain, e.g., Y, or modified form thereof. In some embodiments, $X_5$ is selected from a neutral/polar, especially a polar/large, amino acid residue, e.g., N or Q, a small amino acid residue, e.g., A or S, a basic amino acid residue, e.g., K, or an acidic amino acid residue, e.g., D, or modified form thereof. In some embodiments, $\Sigma_2$ is selected from P, S or G, or modified form thereof.

In certain embodiments, $\Sigma_1$ is S, or modified form thereof, Θ is D, or modified form thereof, $X_1$ is selected a small amino acid residue, e.g., P or S, or modified form thereof, $X_2$ is K, or modified form thereof, $X_3$ is I, or modified form thereof, $X_4$ is G, or modified form thereof $X_5$ is selected from D or N, or modified form thereof, and $\Sigma_2$ is G, or modified form thereof.

Illustrative examples of peptide sequences falling within the scope of formula (VII) include SDPKIGDG [SEQ ID NO:49], SDSKIGDG [SEQ ID NO:50], SDSKIGNG [SEQ ID NO:51], SDSKIGQG [SEQ ID NO:52], SDSKIGAG [SEQ ID NO:53], SDSKIGKG [SEQ ID NO:54], SDSKISKG [SEQ ID NO:55], SDSKIGNG [SEQ ID NO:56], ZSDSKIGNG [SEQ ID NO:57], SDSKIGAG [SEQ ID NO:58], ZSDSKIGAG [SEQ ID NO:59], SPKMVQGSG [SEQ ID NO:60], SPKMVQGSG [SEQ ID NO:61], SDSKIGNG [SEQ ID NO:62], SPKMVQGSG [SEQ ID NO:63], SDSKIGNG [SEQ ID NO:64], SDSKIGNG [SEQ ID NO:65], SLRRSS [SEQ ID NO:66] and SDSKIGNG [SEQ ID NO:67].

In some embodiments, $\Theta_1$ is represented by the formula:

$$CFGX_1X_2\Phi_1DRIX_3X_4X_5SX_6LGC \quad \text{(VIII)}$$

wherein:

$X_{1-6}$ are each independently selected from any amino acid residue, or modified form thereof;

$\Phi_1$ is selected from a hydrophobic amino acid residue, or modified form thereof; and the two C residues are connected by a bridging bond.

In some embodiments, $X_1$ is selected from a basic amino acid residue, e.g., H or R, a hydrophobic amino acid residue, e.g., F or L, a neutral/polar, especially a polar/large, amino acid residue, e.g., Q, or a small amino acid residue, e.g., G, or modified form thereof. In some embodiments, $X_2$ is selected from a small amino acid residue, e.g., P or a basic amino acid residue, e.g., R or K, or modified form thereof. In some embodiments, $\Phi_1$ is selected from M, L or I, or modified form thereof. In some embodiments $X_3$ is selected from a small amino acid residue, e.g., G or S, a neutral/polar, especially a polar/large, amino acid residue, e.g., N, or a basic amino acid residue, e.g., R, H or K, or modified form thereof. In some embodiments $X_4$ is selected from a small amino acid residue, e.g., A or S, or a basic amino acid residue, e.g., H, or modified form thereof. In some embodiments $X_5$ is selected from a small amino acid residue, e.g., S, a basic amino acid residue, e.g., H, a neutral/polar, especially a polar/large, amino acid residue, e.g., Q, or a hydrophobic amino acid residue, e.g., M or V, or modified form thereof. In some embodiments $X_6$ is selected from a small amino acid residue, e.g., G, a basic amino acid residue, e.g., R, or a neutral/polar, especially a polar/large, amino acid residue, e.g., N, or modified form thereof.

Illustrative examples of peptide sequences falling within the scope of formula (VIII) include: CFGFPLDRIGSVSGLGC [SEQ ID NO:68], CFGLPLDRIGSVSGLGC [SEQ ID NO:69], CFGIPLDRIGSVSGLGC [SEQ ID NO:70], CFGHPLDRIGSVSGLGC, [SEQ ID NO:71], CFGQPLDRIGSVSGLGC [SEQ ID NO:72], CFGRPLDRIGSVSGLGC [SEQ ID NO:73], CFGFKLDRIGSVSGLGC [SEQ ID NO:74], CFGFRLDRIGSVSGLGC [SEQ ID NO:75], CFGFPIDRIGSVSGLGC [SEQ ID NO:76], CFGFPMDRIGSVSGLGC [SEQ ID NO:199], CFGFPLDRINSVSGLGC [SEQ ID NO:200], CFGFPLDRIGHVSGLGC [SEQ ID NO:201], CFGFPLDRIGAVSGLGC [SEQ ID NO:77], CFGFPLDRIGSSSGLGC[SEQ ID NO:78], CFGFPLDRIGSQSGLGC [SEQ ID NO:79], CFGFPLDRIGSVSNLGC [SEQ ID NO:80] and CFGFPLDRIGSVSRLGC [SEQ ID NO:81].

In other embodiments, the compounds generally comprise the formula:

$$\Delta_2\text{-}\Theta_2\text{-}\Omega_2 \tag{IX}$$

wherein:

$\Delta_2$ is absent or is a N-terminal portion of a natriuretic peptide or a variant or derivative of that portion;

$\Omega_2$ is a C-terminal portion of a natriuretic peptide or a variant or derivative of that portion; and $\Theta_2$ comprises an amino acid sequence having the formula:

$$CFG\Phi_1 PLDRIX_1 SVSGLGC \tag{X}$$

wherein:

$\Phi_1$ is selected from any hydrophobic amino acid residue, or modified form thereof; and $X_1$ is selected from any small or a basic amino acid residue, or modified form thereof.

In some embodiments, $\Phi_1$ is selected from an amino acid residue having an aromatic side chain, e.g., F, or one having an aliphatic side chain, e.g., L, or modified form thereof.

In some embodiments, $X_1$ is selected from G, S, or a basic residue such as R or K, or modified form thereof.

Suitably, $\Delta_2$ and $\Omega_2$ are independently selected from N- and C-terminal portions, respectively, of natriuretic peptides selected from ANP, BNP, CNP, DNP or an *Oxyuranus* natriuretic peptide such as a natriuretic peptide from *Oxyuranus microlepidotus*, or their variants or derivatives.

In still other embodiments, the compounds generally comprise the formula:

$$\Delta_3\text{-}\Theta_3\text{-}\Omega_3 \tag{XI}$$

wherein:

$\Phi_3$ is a core ring structure of a natriuretic peptide or a variant or derivative of the structure;

$\Omega_3$ is a C-terminal portion of a natriuretic peptide or a variant or derivative of the portion; and $\Delta_3$ comprises an amino acid sequence having the formula:

$$SD\Sigma_1 KGX_1 G \tag{XII}$$

wherein:

$\Sigma 1$ is selected from any small amino acid residue, or modified form thereof; and $X_1$ is selected from any amino acid residue, or modified form thereof.

In some embodiments, $\Sigma_1$ is S or P, or modified form thereof. In some embodiments, $X_1$ is an acidic amino acid residue, e.g., D, or a neutral polar, especially polar/large, amino acid residue, e.g., N, or modified form thereof.

Suitably, $\Theta_3$ and $\Omega_3$ are independently selected from core structures and C-terminal portions, respectively, of natriuretic peptides selected from ANP, BNP, CNP, DNP or an *Oxyuranus* natriuretic peptide such as a natriuretic peptide from *Oxyuranus microlepidotus*, or their variants or derivatives.

If desired, the proteinaceous compounds broadly described above are provided in the form of pharmaceutically acceptable salts.

Yet another aspect of the present invention provides isolated proteinaceous compounds having at least one activity selected from vasodilatory, natriuretic, diuretic, renin-suppressing, bactericidal, weight-reducing or bone growth plate size-increasing activities, in vertebrate animals including mammals, wherein the compounds have the formula:

$$Z_1 SD\Sigma_1 KIGX_1 GCFG\Phi_1 PLDB_1 IX_2 SVSGLGCNRX_3 \Phi_2 QNX_4 PKKZ_2 \tag{XIII}$$

wherein:

$Z_1$ is absent or is a peptide from about 1 to about 50 amino acids or is a protecting moiety, (e.g., an N-terminal blocking residue such as pyroglutamate);

$\Sigma_1$ is a small amino acid residue, or modified form thereof;

$X_1$ is an acidic or neutral/polar amino acid residue, or modified form thereof;

$\Phi_1$ is a hydrophobic amino acid residue, or modified form thereof;

$B_1$ is a basic amino acid residue, or modified form thereof;

$X_2$ is a basic or small amino acid residue, or modified form thereof;

$X_3$ is a small or hydrophobic amino acid residue, or modified form thereof;

$\Phi_2$ is a hydrophobic amino acid residue, or modified form thereof;

$X_4$ is a basic or small amino acid residue, or modified form thereof; and $Z_2$ is absent or is a peptide of from about 1 to about 10 amino acids, the two C residues are connected by a bridging bond, or a pharmaceutically acceptable salt thereof.

In some embodiments, $\Sigma_1$ is selected from P or S, or modified form thereof. In some embodiments, $X_1$ is selected from Q, K, A, S, D or N, or modified form thereof. In some embodiments, $\Phi_1$ is selected from L or F, or modified form thereof. In some embodiments, $B_1$ is selected from H, K or R, or modified form thereof. In some embodiments, $X_2$ is selected from G, S, R or K or modified form thereof. In some embodiments, $X_3$ is selected from P or I, or modified form thereof. In some embodiments, $\Phi_2$ is selected from V or M, or modified form thereof. In some embodiments, $X_4$ is selected from R or P, or modified form thereof.

When the peptide $Z_2$ is present, it suitably comprises the sequence FSGE [SEQ ID NO:14] or a variant or derivative thereof.

Generally, the bridging bond that connects the two C residues is selected from the group consisting of a disulfide bond, a lanthionine bond, a diselenide or mixed sulfide-selenide bond, a methylene bond, a dimethylene bridge, a sulfide/methylene bond, an amide bond and an ester bond. In specific embodiments, the bridging bond is a disulfide bond.

In some embodiments, the compounds comprise any one of the sequences set forth in SEQ ID NO: 90, 91, 94-114, 117, 118, 120, 123, 124, 126-130, 132-134, 150, 154, 160, 166-169, 173, 176 and 178-192 (see Table 2)

In still other embodiments, the compounds generally comprise the formula:

$$\Delta_4\text{-}\Theta_4\Omega_4 \tag{XIV}$$

wherein:

$\Delta_4$ comprises an amino acid sequence having the formula:

$$SD\Sigma_1 KGX_1 G \tag{XV}$$

wherein:

$\Sigma_1$ is selected from any small amino acid residue, or modified form thereof; and $X_1$ is selected from any amino acid residue, or modified form thereof;

$\Theta_4$ is a core ring structure of a natriuretic peptide or a variant or derivative of the structure; and $\Omega 4$ comprises an amino acid sequence having the formula:

$$NRX_7\Phi_2 QNX_8 PKK \tag{XVI}$$

wherein:

$X_7$ is a small or hydrophobic amino acid residue, or modified form thereof;

$\Phi_2$ is a hydrophobic amino acid residue, or modified form thereof;

$X_8$ is a basic or small amino acid residue, or modified form thereof; and

In some embodiments, $\Sigma_1$ is S or P, or modified form thereof. In some embodiments, $X_1$ is an acidic amino acid residue, e.g., D, or a neutral polar, especially polar/large, amino acid residue, e.g., N, or modified form thereof.

In some embodiments, $X_7$ is selected from P or I, or modified form thereof. In some embodiments, $\Phi_2$ is selected from V or M, or modified form thereof. In some embodiments, $X_8$ is selected from R or P, or modified form thereof.

Suitably, $\Phi_4$ is selected from core structures of natriuretic peptides selected from ANP, BNP, CNP or DNP, or their variants or derivatives. In specific embodiments, $\Phi_4$ comprises an amino acid sequence having the formula:

   (XVII)

wherein:

$X_2$, $X_3$, $X_4$, $X_5$ and $X_6$ are independently selected from any amino acid residue, or modified form thereof;

$B_1$ is a basic amino acid residue, or modified form thereof; and $\Phi_1$ is a hydrophobic amino acid residue, or modified form thereof.

In some embodiments, $X_2$ is selected from a small amino acid residue, e.g., G, or a hydrophobic amino acid residue, e.g., F or L, or a basic amino acid residue such as H or R, or a modified form thereof. In some embodiments, $\Phi_1$ is selected from an amino acid residue having an aliphatic side chain, e.g., L, I or M, or modified form thereof. In some embodiments, $X_3$ is selected from a small amino acid residue, e.g., G or S, or a neutral/polar amino acid residue, e.g., N, or a modified form thereof. In some embodiments, $X_4$ is selected from a small amino acid residue, e.g., A or S, or a basic amino acid residue, e.g., H, or a modified form thereof. In some embodiments, $X_5$ is selected from a small amino acid residue, e.g., S, or a hydrophobic amino acid residue, e.g., V or M, or a neutral/polar amino acid residue such as Q, or a modified form thereof. In some embodiments, $X_6$ is selected from a small amino acid residue, e.g., G, or a neutral/polar amino acid residue, e.g., N, or a modified form thereof.

Yet another aspect of the present invention provides isolated proteinaceous compounds having at least one activity selected from vasodilatory, natriuretic, diuretic, renin-suppressing, bactericidal, weight-reducing or bone growth plate size-increasing activities, in vertebrate animals including mammals, wherein the compounds have the formula:

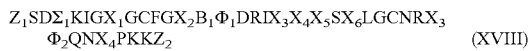   (XVIII)

wherein:

$Z_1$ is absent or is a peptide from about 1 to about 50 amino acids or is a protecting moiety, (e.g., an N-terminal blocking residue such as pyroglutamate);

$\Sigma_1$ is a small amino acid residue, or modified form thereof;

$X_1$ is an acidic or neutral/polar amino acid residue, or modified form thereof;

$B_1$ is a basic amino acid residue, or modified form thereof;

$\Phi_1$ is a hydrophobic amino acid residue, or modified form thereof;

$X_2$ is a small, hydrophobic or basic amino acid residue, or modified form thereof;

$X_3$ is a small or neutral/polar amino acid residue, or modified form thereof;

$X_4$ is a small or basic amino acid residue, or modified form thereof;

$X_5$ is a small, hydrophobic or neutral/polar amino acid residue, or modified form thereof;

$X_6$ is a small or neutral/polar amino acid residue, or modified form thereof;

$X_7$ is a small or hydrophobic amino acid residue, or modified form thereof;

$\Phi_2$ is a hydrophobic amino acid residue, or modified form thereof;

$X_8$ is a basic or small amino acid residue, or modified form thereof; and $Z_2$ is absent or is a peptide of from about 1 to about 10 amino acids, the two C residues are connected by a bridging bond, or a pharmaceutically acceptable salt thereof.

In some embodiments, $\Sigma_1$ is selected from P or S, or modified form thereof. In some embodiments, $X_1$ is selected from Q, K, A, S, D or N, or modified form thereof. In some embodiments, $B_1$ is selected from K or R, or modified form thereof. In some embodiments, $X_2$ is selected from G, F, L, H or R, or modified form thereof. In some embodiments, $\Phi_1$ is selected from L, I or M, or modified form thereof. In some embodiments, $X_3$ is selected from G, S or N, or modified form thereof. In some embodiments, $X_4$ is selected from A, S or H, or modified form thereof. In some embodiments, $X_5$ is selected from S, V, M or Q, or modified form thereof. In some embodiments, $X_6$ is selected from G or N, or a modified form thereof. In some embodiments, $X_7$ is selected from P or I, or modified form thereof. In some embodiments, $\Phi_2$ is selected from V or M, or modified form thereof. In some embodiments, $X_8$ is selected from R or P, or modified form thereof.

When the peptide $Z_2$ is present, it suitably comprises the sequence FSGE [SEQ ID NO:14] or a variant or derivative thereof.

Generally, the bridging bond that connects the two C residues is selected from the group consisting of a disulfide bond, a lanthionine bond, a diselenide or mixed sulfide-selenide bond, a methylene bond, a dimethylene bridge, a sulfide/methylene bond, an amide bond and an ester bond. In specific embodiments, the bridging bond is a disulfide bond.

In some embodiments, when the sequence Asn-Pro is present, it is replaced by a sequence selected from Ala-Pro, Gln-Pro, Ala-Hyp or Gln-Hyp. In some embodiments, the sequence Asn-Gly is replaced by a sequence selected from Gln-Gly or Ala-Gly. In some embodiments the Met residue is replaced by Nor or Val. In some embodiments, one or both of the C residues are replaced by selenocysteine. In some embodiments the N-terminus is blocked by pGlu, Pro, Hyp or any N-acetylated residue. Alternatively, or in addition, the C-terminus is blocked by amidation or by other means, or the compounds are cyclized (e.g., end to end).

If desired, the proteinaceous compounds broadly described above are provided in the form of pharmaceutically acceptable salts.

Yet another aspect of the present invention provides isolated proteinaceous compounds having at least one activity selected from vasodilatory, natriuretic, diuretic, renin-suppressing, bactericidal, weight-reducing or bone growth plate size-increasing activities, in vertebrate animals including mammals, wherein the compounds have the formula:

Still other aspects of the present invention provide isolated polynucleotides that comprise a nucleotide sequence encoding a compound as broadly described above, and vectors that comprise such polynucleotides optionally operably connected to a regulatory sequence, as well as host cells containing such vectors. In a related aspect, the invention provides processes for producing a compound as broadly described above, including a process that comprises culturing a host cell containing a vector under conditions sufficient to produce a compound of the invention from a polynucleotide as broadly described above and isolating the compound.

In a further aspect, the invention provides antigen-binding molecules that are immuno-interactive with a compound as broadly described above. The molecules are useful in screening expression libraries for compounds of the invention as well as isolating or detecting such compounds.

In still another aspect, the present invention provides a pharmaceutical composition comprising a compound as broadly described above, and a pharmaceutically acceptable carrier, excipient and/or diluent. These compositions and the aforementioned compounds are useful, either singly or in combination, for inducing, stimulating or otherwise promoting at least one activity selected from vasodilatory, natriuretic, diuretic, renin-suppressing, bactericidal, weight-reducing or bone growth plate size-increasing activities, in vertebrate animals including mammals. Accordingly, in a further aspect, the invention provides methods for inducing, stimulating or otherwise promoting at least one of these activities in a subject, wherein the methods generally comprise administering to the subject an effective amount of a compound or composition as broadly described above.

Advantageously, these activities are useful for treating or preventing a variety of conditions including heart failure, nephrotic syndrome, cirrhosis of the liver, hypertension, kidney failure and other edematous states, bacterial infections, weight loss, asthma, inflammatory-related diseases, erectile dysfunction, hypercholesterolemia, skeletal dysplasias and as a protectant for toxicity of anti-cancer drugs. Accordingly, in still a further aspect, the invention provides methods for treating or preventing at least one of these conditions in a subject, wherein the methods generally comprise administering to the subject an effective amount of a compound or composition as broadly described above.

BRIEF DESCRIPTION OF THE DRAWINGS

FIG. 2 is a diagrammatic representation showing a comparison of the isolated *Oxyuranus microlepidotus* natriuretic peptides with the invariant residues of the natriuretic peptide family and previously isolated venom natriuretic peptides. Many other sequences predicted from the full gene sequences are available on Swissprot.

FIG. 6 is a graphical representation showing the comparative stability of (a) TNPc and Wt-hANP in human and rat plasma; (b) TNPc, BNP, ANP and DNP against NEP enzyme; and (c) TNPc, DNP, ANP and BNP against plasmin enzyme.

DETAILED DESCRIPTION OF THE INVENTION

1. Definitions

Figure 1:
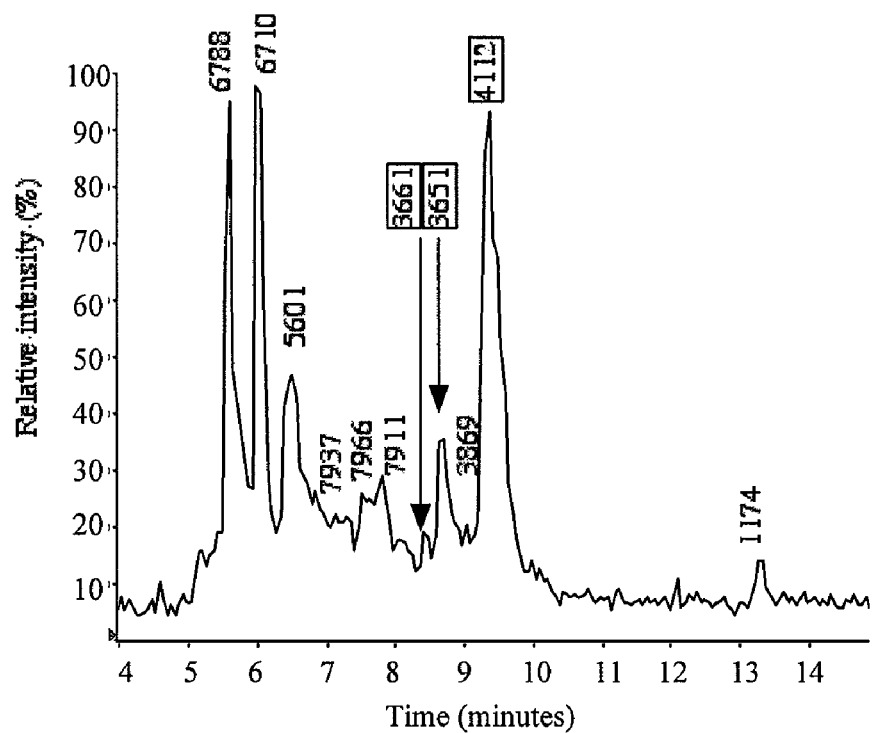
FIG. 1 is a graphical representation showing an LC-MS profile of <10 kDa centrifuge fraction of *Oxyuranus microlepidotus* (Inland taipan) venom. Mass in Daltons is given above each major peak. On-line LC-MS of venoms was performed on a Vydac C18 analytical column (2.1×35 mm, 5μ particle size, 300 Å) with Solvent A (0.05% TFA, $H_2O$) and Solvent B (90% acetonitrile in 0.045% TFA) at a turbospray flow rate of 130 μL/min. The solvent delivery and gradient formation was achieved using an Applied Biosystems 140 B solvent delivery system. The variable gradient was 0-20% in the first two minutes and then 20-45% over the next 12 minutes followed by 45-80% over the next minute. Electrospray mass spectra were acquired on a PE-SCIEX triple quadrupole mass spectrometer that was equipped with an Ionspray atmospheric pressure ionisation source. Samples (10 μL) were injected manually into the LC-MS system and analysed in positive ion mode. Full scan data was acquired at an orifice potential of 80V over the mass range 400-2100 Da with a step size of 0.2 amu.

Unless defined otherwise, all technical and scientific terms used herein have the same meaning as commonly understood by those of ordinary skill in the art to which the invention belongs. Although any methods and materials similar or equivalent to those described herein can be used in the practice or testing of the present invention, preferred methods and materials are described. For the purposes of the present invention, the following terms are defined below.

The articles "a" and "an" are used herein to refer to one or to more than one (i.e. to at least one) of the grammatical object of the article. By way of example, "an element" means one element or more than one element.

By "antigen-binding molecule" is meant a molecule that has binding affinity for a target antigen. It will be understood that this term extends to immunoglobulins, immunoglobulin fragments and non-immunoglobulin derived protein frameworks that exhibit antigen-binding activity.

By "biologically active portion" is meant a portion of a full-length parent peptide or polypeptide which portion retains an activity of the parent compound. For example, a biologically active portion of a natriuretic peptide of the invention will retain at least one activity selected from vasodilatory, natriuretic, diuretic, renin-suppressing, bactericidal, weight-reducing or bone growth plate size-increasing activities, in mammal. As used herein, the term "biologically active portion" includes deletion mutants and small peptides, for example of at least 8, 9, 10, 11, 12, 13, 14, 15, 16, 17, 18, 19, 20, 21, 22, 23, 24, 25 contiguous amino acids, which comprise an activity of a parent compound. Portions of this type may be obtained through the application of standard recombinant nucleic acid techniques or synthesized using conventional liquid or solid phase synthesis techniques. For example, reference may be made to solution synthesis or solid phase synthesis as described, for example, in Chapter 9 entitled "*Peptide Synthesis*" by Atherton and Shephard which is included in a publication entitled "*Synthetic Vaccines*" edited by Nicholson and published by Blackwell Scientific Publications. Alternatively, peptides can be produced by digestion of a peptide or polypeptide of the invention with proteinases such as endoLys-C, endoArg-C, endoGlu-C and *staphylococcus* V8-protease. The digested fragments can be purified by, for example, high performance liquid chromatographic (HPLC) techniques. Recombinant nucleic acid techniques can also be used to produce such portions.

The term "biological sample" as used herein refers to a sample that may be extracted, untreated, treated, diluted or concentrated from an animal. The biological sample may include a biological fluid such as whole blood, serum, plasma, saliva, urine, sweat, ascitic fluid, peritoneal fluid, synovial fluid, amniotic fluid, cerebrospinal fluid, tissue biopsy, and the like. In certain embodiments, the biological sample is blood, especially peripheral blood.

Throughout this specification, unless the context requires otherwise, the words "comprise", "comprises" and "comprising" will be understood to imply the inclusion of a stated step or element or group of steps or elements but not the exclusion of any other step or element or group of steps or elements.

By "corresponds to" or "corresponding to" is meant a polynucleotide (a) having a nucleotide sequence that is substantially identical or complementary to all or a portion of a reference polynucleotide sequence or (b) encoding an amino acid sequence identical to an amino acid sequence in a peptide or protein. This phrase also includes within its scope a peptide or polypeptide having an amino acid sequence that is substantially identical to a sequence of amino acids in a reference peptide or protein.

As used herein, the terms "culturing," "culture" and the like refer to the set of procedures used in vitro where a population of cells (or a single cell) is incubated under conditions that have been shown to support the growth or maintenance of the cells in vitro. The art recognizes a wide number of formats, media, temperature ranges, gas concentrations etc., which need to be defined in a culture system. The parameters will vary based on the format selected and the specific needs of the individual who practices the methods herein disclosed. However, it is recognized that the determination of culture parameters is routine in nature.

By "derivative" is meant a peptide or polypeptide that has been derived from the basic sequence by modification, for example by conjugation or complexing with other chemical moieties or by post-translational modification techniques as would be understood in the art.

By "effective amount", in the context of modulating an activity or of treating or preventing a condition is meant the administration of that amount of active to an individual in need of such modulation, treatment or prophylaxis, either in a single dose or as part of a series, that is effective for modulation of that effect or for treatment or prophylaxis of that condition. The effective amount will vary depending upon the health and physical condition of the individual to be treated, the taxonomic group of individual to be treated, the formulation of the composition, the assessment of the medical situation, and other relevant factors. It is expected that the amount will fall in a relatively broad range that can be determined through routine trials.

By "expression vector" is meant any autonomous genetic element capable of directing the transcription of a polynucleotide contained within the vector and suitably the synthesis of a peptide or polypeptide encoded by the polynucleotide. Such expression vectors are known to practitioners in the art.

The term "gene" as used herein refers to any and all discrete coding regions of the cell's genome, as well as associated non-coding and regulatory regions. The gene is also intended to mean the open reading frame encoding specific polypeptides, introns, and adjacent 5' and 3' non-coding nucleotide sequences involved in the regulation of expression. In this regard, the gene may further comprise control signals such as promoters, enhancers, termination and/or polyadenylation signals that are naturally associated with a given gene, or heterologous control signals. The DNA sequences may be cDNA or genomic DNA or a fragment thereof. The gene may be introduced into an appropriate vector for extrachromosomal maintenance or for integration into the host.

"Hybridization" is used herein to denote the pairing of complementary nucleotide sequences to produce a DNA-DNA hybrid or a DNA-RNA hybrid. Complementary base sequences are those sequences that are related by the base-pairing rules. In DNA, A pairs with T and C pairs with G. In RNA U pairs with A and C pairs with G. In this regard, the terms "match" and "mismatch" as used herein refer to the hybridization potential of paired nucleotides in complementary nucleic acid strands. Matched nucleotides hybridize efficiently, such as the classical A-T and G-C base pair mentioned above. Mismatches are other combinations of nucleotides that do not hybridize efficiently.

Reference herein to "immuno-interactive" includes reference to any interaction, reaction, or other form of association between molecules and in particular where one of the molecules is, or mimics, a component of the immune system.

By "isolated" is meant material that is substantially or essentially free from components that normally accompany it in its native state. For example, an "isolated polynucleotide", as used herein, refers to a polynucleotide, which has been purified from the sequences which flank it in a naturally-occurring state, e.g., a DNA fragment which has been removed from the sequences that are normally adjacent to the fragment. Alternatively, an "isolated peptide" or an "isolated polypeptide" and the like, as used herein, refer to in vitro isolation and/or purification of a peptide or polypeptide molecule from its natural cellular environment, and from association with other components of the cell, i.e., it is not associated with in vivo substances.

By "marker gene" is meant a gene that imparts a distinct phenotype to cells expressing the marker gene and thus allows such transformed cells to be distinguished from cells that do not have the marker. A selectable marker gene confers a trait for which one can 'select' based on resistance to a selective agent (e.g., a herbicide, antibiotic, radiation, heat, or other treatment damaging to untransformed cells). A screenable marker gene (or reporter gene) confers a trait that one can identify through observation or testing, i.e., by 'screening' (e.g. β-glucuronidase, luciferase, or other enzyme activity not present in untransformed cells).

As used herein, a "naturally-occurring" nucleic acid molecule refers to an RNA or DNA molecule having a nucleotide sequence that occurs in nature. For example a naturally-occurring nucleic acid molecule can encode a natural protein.

The term "oligonucleotide" as used herein refers to a polymer composed of a multiplicity of nucleotide residues (deoxyribonucleotides or ribonucleotides, or related structural variants or synthetic analogues thereof, including nucleotides with modified or substituted sugar groups and the like) linked via phosphodiester bonds (or related structural variants or synthetic analogues thereof). Thus, while the term "oligonucleotide" typically refers to a nucleotide polymer in which the nucleotide residues and linkages between them are naturally-occurring, it will be understood that the term also includes within its scope various analogues including, but not restricted to, peptide nucleic acids (PNAs), phosphorothioate, phosphorodithioate, phosphoroselenoate, phosphorodiselenoate, phosphoroanilothioate, phosphoraniladate, phosphoroamidate, methyl phosphonates, 2-O-methyl ribonucleic acids, and the like. The exact size of the molecule can vary depending on the particular application. Oligonucleotides are a polynucleotide subset with 200 bases or fewer in length.

Preferably, oligonucleotides are 10 to 60 bases in length and most preferably 12, 13, 14, 15, 16, 17, 18, 19, or 20 to 40 bases in length. Oligonucleotides are usually single stranded, e.g., for probes; although oligonucleotides may be double stranded, e.g., for use in the construction of a variant nucleic acid sequence. Oligonucleotides of the invention can be either sense or antisense oligonucleotides.

The term "operably connected" or "operably linked" as used herein means placing a structural gene under the regulatory control of a promoter, which then controls the transcription and optionally translation of the gene. In the construction of heterologous promoter/structural gene combinations, it is generally preferred to position the genetic sequence or promoter at a distance from the gene transcription start site that is approximately the same as the distance between that genetic sequence or promoter and the gene it controls in its natural setting; i.e. the gene from which the genetic sequence or promoter is derived. As is known in the art, some variation in this distance can be accommodated without loss of function. Similarly, the preferred positioning of a regulatory sequence element with respect to a heterologous gene to be placed under its control is defined by the positioning of the element in its natural setting; i.e. the genes from which it is derived.

By "pharmaceutically acceptable carrier" is meant a solid or liquid filler, diluent or encapsulating substance that can be safely used in topical or systemic administration to a mammal.

The term "polynucleotide" or "nucleic acid" as used herein designates mRNA, RNA, cRNA, cDNA or DNA. The term typically refers polymeric form of nucleotides of at least 10 bases in length, either ribonucleotides or deoxynucleotides or a modified form of either type of nucleotide. The term includes single and double stranded forms of DNA.

"Polypeptide," "peptide" and "protein" are used interchangeably herein to refer to a polymer of amino acid residues and to variants and synthetic analogues of the same. Thus, these terms apply to amino acid polymers in which one or more amino acid residues is a synthetic non-naturally-occurring amino acid, such as a chemical analogue of a corresponding naturally-occurring amino acid, as well as to naturally-occurring amino acid polymers.

By "primer" is meant an oligonucleotide which, when paired with a strand of DNA, is capable of initiating the synthesis of a primer extension product in the presence of a suitable polymerizing agent. The primer is preferably single-stranded for maximum efficiency in amplification but can alternatively be double-stranded. A primer must be sufficiently long to prime the synthesis of extension products in the presence of the polymerization agent. The length of the primer depends on many factors, including application, temperature to be employed, template reaction conditions, other reagents, and source of primers. For example, depending on the complexity of the target sequence, the oligonucleotide primer typically contains 15 to 35 or more nucleotide residues, although it can contain fewer nucleotide residues. Primers can be large polynucleotides, such as from about 35 nucleotides to several kilobases or more. Primers can be selected to be "substantially complementary" to the sequence on the template to which it is designed to hybridize and serve as a site for the initiation of synthesis. By "substantially complementary", it is meant that the primer is sufficiently complementary to hybridize with a target polynucleotide. Preferably, the primer contains no mismatches with the template to which it is designed to hybridize but this is not essential. For example, non-complementary nucleotide residues can be attached to the 5' end of the primer, with the remainder of the primer sequence being complementary to the template. Alternatively, non-complementary nucleotide residues or a stretch of non-complementary nucleotide residues can be interspersed into a primer, provided that the primer sequence has sufficient complementarity with the sequence of the template to hybridize therewith and thereby form a template for synthesis of the extension product of the primer.

"Probe" refers to a molecule that binds to a specific sequence or sub-sequence or other moiety of another molecule. Unless otherwise indicated, the term "probe" typically refers to a polynucleotide probe that binds to another polynucleotide, often called the "target polynucleotide", through complementary base pairing. Probes can bind target polynucleotides lacking complete sequence complementarity with the probe, depending on the stringency of the hybridization conditions. Probes can be labeled directly or indirectly.

The term "recombinant polynucleotide" as used herein refers to a polynucleotide formed in vitro by the manipulation of nucleic acid into a form not normally found in nature. For example, the recombinant polynucleotide may be in the form of an expression vector. Generally, such expression vectors include transcriptional and translational regulatory nucleic acid operably linked to the nucleotide sequence.

By "recombinant polypeptide" is meant a polypeptide made using recombinant techniques, i.e., through the expression of a recombinant or synthetic polynucleotide.

By "regulatory sequence" is meant nucleic acid sequences (e.g., DNA) necessary for expression of an operably linked coding sequence in a particular host cell. The regulatory sequences that are suitable for prokaryotic cells for example, include a promoter, and optionally a cis-acting sequence such as an operator sequence and a ribosome binding site. Control sequences that are suitable for eukaryotic cells include promoters, polyadenylation signals, transcriptional enhancers, translational enhancers, leader or trailing sequences that modulate mRNA stability, as well as targeting sequences that target a product encoded by a transcribed polynucleotide to an intracellular compartment within a cell or to the extracellular environment.

The term "sequence identity" as used herein refers to the extent that sequences are identical on a nucleotide-by-nucleotide basis or an amino acid-by-amino acid basis over a window of comparison. Thus, a "percentage of sequence identity" is calculated by comparing two optimally aligned sequences over the window of comparison, determining the number of positions at which the identical nucleic acid base (e.g., A, T, C, G, I) or the identical amino acid residue (e.g., Ala, Pro, Ser, Thr, Gly, Val, Leu, Ile, Phe, Tyr, Trp, Lys, Arg, His, Asp, Glu, Asn, Gln, Cys and Met) occurs in both sequences to yield the number of matched positions, dividing the number of matched positions by the total number of positions in the window of comparison (i.e., the window size), and multiplying the result by 100 to yield the percentage of sequence identity. For the purposes of the present invention, "sequence identity" will be understood to mean the "match percentage" calculated by the DNASIS computer program (Version 2.5 for windows; available from Hitachi Software engineering Co., Ltd., South San Francisco, Calif., USA) using standard defaults as used in the reference manual accompanying the software.

"Similarity" refers to the percentage number of amino acids that are identical or constitute conservative substitutions as defined in Table 5 infra. Similarity may be determined using sequence comparison programs such as GAP (Deveraux et al. 1984, *Nucleic Acids Research* 12, 387-395). In this way, sequences of a similar or substantially different length to those cited herein might be compared by insertion of gaps into the alignment, such gaps being determined, for example, by the comparison algorithm used by GAP.

Terms used to describe sequence relationships between two or more polynucleotides or polypeptides include "reference sequence", "comparison window", "sequence identity", "percentage of sequence identity" and "substantial identity".

A "reference sequence" is at least 12 but frequently 15 to 18 and often at least 25 monomer units, inclusive of nucleotides and amino acid residues, in length. Because two polynucleotides may each comprise (1) a sequence (i.e., only a portion of the complete polynucleotide sequence) that is similar between the two polynucleotides, and (2) a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window" refers to a conceptual segment of at least 6 contiguous positions, usually about 50 to about 100, more usually about 100 to about 150 in which a sequence is compared to a reference sequence of the same number of contiguous positions after the two sequences are optimally aligned. The comparison window may comprise additions or deletions (i.e., gaps) of about 20% or less as compared to the reference sequence (which does not comprise additions or deletions) for optimal alignment of the two sequences. Optimal alignment of sequences for aligning a comparison window may be conducted by computerized implementations of algorithms (GAP, BESTFIT, FASTA, and TFASTA in the Wisconsin Genetics Software Package Release 7.0, Genetics Computer Group, 575 Science Drive Madison, Wis., USA) or by inspection and the best alignment (i.e., resulting in the highest percentage homology over the comparison window) generated by any of the various methods selected. Reference also may be made to the BLAST family of programs as for example disclosed by Altschul et al., 1997, *Nucl. Acids Res.* 25:3389. A detailed discussion of sequence analysis can be found in Unit 19.3 of Ausubel et al., "Current Protocols in Molecular Biology", John Wiley & Sons Inc, 1994-1998, Chapter 15.

The term "subject" refers to any subject, particularly a vertebrate subject, and even more particularly a mammalian subject, for whom therapy or prophylaxis is desired. Suitable vertebrate animals that fall within the scope of the invention include, but are not restricted to, primates, avians, livestock animals (e.g., sheep, cows, horses, donkeys, pigs), laboratory test animals (e.g., rabbits, mice, rats, guinea pigs, hamsters), companion animals (e.g., cats, dogs) and captive wild animals (e.g., foxes, deer, dingoes). A preferred subject is a human in need of treatment or prophylaxis of a disease or condition, as defined herein. However, it will be understood that the aforementioned terms do not imply that symptoms are present.

As used herein, the term "substantially free" means that a preparation of a natriuretic peptide of the invention is at least 10% pure. In certain embodiments, the preparation of natriuretic peptide has less than about 30%, 20%, 10% and preferably less than about 5% (by dry weight), of non-natriuretic peptide (also referred to herein as a "contaminating protein"), or of chemical precursors or non-natriuretic peptide chemicals. When the natriuretic peptide or biologically active portion thereof is recombinantly produced, it is also preferably substantially free of culture medium, i.e., culture medium represents less than about 20%, more preferably less than about 10%, and more preferably less than about 5% of the volume of the protein preparation. The invention includes isolated or purified preparations of at least 0.01, 0.1, 1.0, and 10 milligrams in dry weight.

By "substantially purified" is meant a compound that has been separated from components that naturally accompany it. Typically, a compound is substantially pure when at least 60%, 65%, 70%, 75%, 80%, 85%, 90%, 91%, 92%, 93%, 94%, 95%, 96%, 97%, 98%, 99% of the total material (by volume, by wet or dry weight, or by mole percent or mole fraction) in a sample is the compound of interest. Purity can be measured by any appropriate method, e.g., by chromatography or HPLC analysis. For those compounds prepared by synthetic procedures or derivatisation of a naturally-occurring compound, "substantially purified" refers to a compound that has been separated from the reagents and solvents used in the synthetic procedure.

The term "transformation" means alteration of the genotype of an organism, for example a bacterium, yeast or plant, by the introduction of a foreign or endogenous nucleic acid.

The term "variant" refers to polypeptides in which one or more amino acids have been replaced by different amino acids. It is well understood in the art that some amino acids may be changed to others with broadly similar properties without changing the nature of the activity of the polypeptide (conservative substitutions) as described hereinafter. These terms also encompass polypeptides in which one or more amino acids have been added or deleted, or replaced with different amino acids.

By "vector" is meant a polynucleotide molecule, preferably a DNA molecule derived, for example, from a plasmid, bacteriophage, yeast or virus, into which a polynucleotide can be inserted or cloned. A vector preferably contains one or more unique restriction sites and can be capable of autonomous replication in a defined host cell including a target cell or tissue or a progenitor cell or tissue thereof, or be integrable with the genome of the defined host such that the cloned sequence is reproducible. Accordingly, the vector can be an autonomously replicating vector, i.e., a vector that exists as an extrachromosomal entity, the replication of which is independent of chromosomal replication, e.g., a linear or closed circular plasmid, an extrachromosomal element, a minichromosome, or an artificial chromosome. The vector can contain any means for assuring self-replication. Alternatively, the vector can be one which, when introduced into the host cell, is integrated into the genome and replicated together with the chromosome(s) into which it has been integrated. A vector system can comprise a single vector or plasmid, two or more vectors or plasmids, which together contain the total DNA to be introduced into the genome of the host cell, or a transposon. The choice of the vector will typically depend on the compatibility of the vector with the host cell into which the vector is to be introduced. In the present case, the vector is preferably a viral or viral-derived vector, which is operably functional in animal and preferably mammalian cells. Such vector may be derived from a poxvirus, an adenovirus or yeast. The vector can also include a selection marker such as an antibiotic resistance gene that can be used for selection of suitable transformants. Examples of such resistance genes are known to those of skill in the art.

2. Proteinaceous Compounds of the Invention

The present invention is based, in part, on the isolation and characterization of novel natriuretic peptides from *Oxyuranus microlepidotus* (Inland taipan), reputedly the world's most venomous snake. These peptides, which are also referred to herein as TNPa, TNPb and TNPc, share similarity within the 17-membered ring structure, which contains a natriuretic signature consensus sequence, with known natriuretic peptides at the amino acid level (see FIG. 2 and compare Tables 1 and 2) and are proposed, therefore to have at least one activity selected from natriuretic, diuretic, renin-suppressing, bactericidal, weight-reducing and/or bone growth plate size-increasing activities, which are known activities of natriuretic peptides. For example, the ability of TNPc to reduce blood pressure without increasing heart rate, as demonstrated in the Examples infra, provides evidence that this peptide and its variants are useful in the treatment of congestive heart failure.

The natriuretic peptide TNPc disclosed herein, whose amino acid sequences is set forth in SEQ ID NO:90, as well as its fragments, variants and derivatives, illustrative examples of which are set forth in SEQ ID NO: 1-7, 15-81 supra and in SEQ ID NO: 91, 94-114, 117, 118, 120, 123, 124, 126-130, 132-134, 150, 154, 160, 166-169, 173, 176 and 178-182 (Table 2) and are collectively referred to as "compounds, peptides or natriuretic peptides of the invention" or as "*Oxyuranus* natriuretic peptides" or as "TNPs." Nucleic acid molecules encoding such molecules are collectively referred to as "nucleic acids of the invention" or as "*Oxyuranus* nucleic acids." Thus, in accordance with the present invention, proteinaceous compounds comprising at least one of these activities are provided, comprising at least a biologically active portion of the *Oxyuranus* natriuretic peptide TNPc, or a variant or derivative thereof.

The sequence of amino acid residues of these compounds, and preferred embodiments thereof, are defined in terms of amino acids of certain characteristics or subclasses. Amino acid residues can be generally sub-classified into major subclasses as follows:

Acidic: The residue has a negative charge due to loss of H ion at physiological pH and the residue is attracted by aqueous solution so as to seek the surface positions in the conformation of a peptide in which it is contained when the peptide is in aqueous medium at physiological pH. Amino acids having an acidic side chain include glutamic acid and aspartic acid.

Basic: The residue has a positive charge due to association with H ion at physiological pH or within one or two pH units thereof (e.g., histidine) and the residue is attracted by aqueous solution so as to seek the surface positions in the conformation of a peptide in which it is contained when the peptide is in aqueous medium at physiological pH. Amino acids having a basic side chain include arginine, lysine and histidine.

Charged: The residues are charged at physiological pH and, therefore, include amino acids having acidic or basic side chains (i.e., glutamic acid, aspartic acid, arginine, lysine and histidine).

Hydrophobic: The residues are not charged at physiological pH and the residue is repelled by aqueous solution so as to seek the inner positions in the conformation of a peptide in which it is contained when the peptide is in aqueous medium. Amino acids having a hydrophobic side chain include tyrosine, valine, isoleucine, leucine, methionine, phenylalanine and tryptophan.

Neutral/polar: The residues are not charged at physiological pH, but the residue is not sufficiently repelled by aqueous solutions so that it would seek inner positions in the conformation of a peptide in which it is contained when the peptide is in aqueous medium. Amino acids having a neutral/polar side chain include asparagine, glutamine, cysteine, histidine, serine and threonine.

This description also characterizes certain amino acids as "small" since their side chains are not sufficiently large, even if polar groups are lacking, to confer hydrophobicity. With the exception of proline, "small" amino acids are those with four carbons or less when at least one polar group is on the side chain and three carbons or less when not. Amino acids having a small side chain include glycine, serine, alanine and threonine. The gene-encoded secondary amino acid proline is a special case due to its known effects on the secondary conformation of peptide chains. The structure of proline differs from all the other naturally-occurring amino acids in that its side chain is bonded to the nitrogen of the α-amino group, as well as the α-carbon. Several amino acid similarity matrices (e.g., PAM120 matrix and PAM250 matrix as disclosed for example by Dayhoff et al. (1978) A model of evolutionary change in proteins. Matrices for determining distance relationships In M. O. Dayhoff, (ed.), Atlas of protein sequence and structure, Vol. 5, pp. 345-358, National Biomedical Research Foundation, Washington D.C.; and by Gonnet et al., 1992*, Science* 256(5062): 144301445), however, include proline in the same group as glycine, serine, alanine and threonine. Accordingly, for the purposes of the present invention, proline is classified as a "small" amino acid.

The degree of attraction or repulsion required for classification as polar or nonpolar is arbitrary and, therefore, amino acids specifically contemplated by the invention have been classified as one or the other. Most amino acids not specifically named can be classified on the basis of known behavior.

Amino acid residues can be further sub-classified as cyclic or noncyclic, and aromatic or nonaromatic, self-explanatory classifications with respect to the side-chain substituent groups of the residues, and as small or large. The residue is considered small if it contains a total of four carbon atoms or less, inclusive of the carboxyl carbon, provided an additional polar substituent is present; three or less if not. Small residues are, of course, always nonaromatic. Dependent on their structural properties, amino acid residues may fall in two or more classes.

For the naturally-occurring protein amino acids, sub-classification according to the foregoing scheme is presented in Table 3.

The amino acids in the proteinaceous compounds of the invention may be those encoded by genes or their analogues or D-isomers thereof. Compounds within the scope of the present invention can be obtained by modifying the disclosed formulae in numerous ways, while preserving the activity of the natriuretic compounds thus obtained. For example, while the amino acids of these compounds are normally in the natural L optical isomer form, one or more, usually two or less and preferably one amino acid may be replaced with the optical isomer D form, or a D,L-racemic mixture can be provided in the molecules comprising the peptide compound. In one embodiment, the compounds of the invention are in a form wherein all of the residues are in the D-configuration thus conferring resistance to protease activity while retaining at least one activity associated with parent compounds. The resulting molecules are themselves enantiomers of the native L-amino acid-containing forms.

The nomenclature used to describe proteinaceous molecules of the present invention follows the conventional practice wherein the amino group is presented to the left and the carboxy group to the right of each amino acid residue. In the formulae representing selected specific embodiments of the present invention, the amino- (N-) and carboxy- (C-) terminal groups, although not specifically shown, will be understood to be in the form they would assume at physiological pH values, unless otherwise specified. In the amino acid structure formulae, each residue is generally represented by a single letter designation, corresponding to the trivial name of the amino acid, in accordance with the Table 4, in which the three-letter designations for each residue is also shown:

"Modified" amino acids that may be included in the compounds of the invention can be gene-encoded amino acids which have been processed after translation of the gene, e.g., by the addition of methyl groups or derivatisation through covalent linkage to other substituents or oxidation or reduction or other covalent modification. The classification into which the resulting modified amino acid falls will be determined by the characteristics of the modified form. For example, if lysine were modified by acylating the ϵ-amino group, the modified form would not be classed as basic but as polar/large.

Certain commonly encountered amino acids, which are not encoded by the genetic code, include, for example, β-alanine (β-Ala), or other omega-amino acids, such as 3-aminopropionic, 2,3-diaminopropionic (2,3-diaP), 4-aminobutyric and so forth, α-aminoisobutyric acid (Aib), sarcosine (Sar), ornithine (Om), citrulline (Cit), t-butylalanine (t-BuA), t-butylglycine (t-BuG), N-methylisoleucine (N-MeIle), phenylglycine (Phg), and cyclohexylalanine (Cha), norleucine (Nle), 2-naphthylalanine (2-NaI); 1,2,3,4-tetrahydroisoquinoline- 3-carboxylic acid (Tic); β-2-thienylalanine (Thi); methionine sulfoxide (MSO); and homoarginirie (Har). These also fall conveniently into particular categories.

Based on the above definitions, Sar, β-Ala and Aib are small; t-BuA, t-BuG, N-MeIle, Nle, Mvl, Cha, Phg, NaI, Thi and Tic are hydrophobic; 2,3-diaP, Orn and Har are basic; Cit, Acetyl Lys and MSO are neutral/polar/large. The various omega-amino acids are classified according to size as small (β-Ala and 3-aminopropionic) or as large and hydrophobic (all others).

Other amino acid substitutions for those encoded in the gene can also be included in proteinaceous molecules within the scope of the invention and can be classified within this general scheme according to their structure.

In the compounds of the invention, one or more amide linkages (—CO—NH—) may optionally be replaced with another linkage which is an isostere such as —CH$_2$NH—, —CH$_2$S—, —CH$_2$CH$_2$—, —CH=CH— (cis and trans), —COCH$_2$—, —CH(OH)CH$_2$— and —CH$_2$SO—. This replacement can be made by methods known in the art. The following references describe preparation of peptide analogues which include these alternative-linking moieties: Spatola, A. F., Vega Data (March 1983), Vol. 1, Issue 3, "Peptide Backbone Modifications" (general review); Spatola, A. F., in "Chemistry and Biochemistry of Amino Acids Peptides and Proteins", B. Weinstein, eds., Marcel Dekker, New York, p. 267 (1983) (general review); Morley, J. S., Trends Pharm Sci (1980) pp. 463-468 (general review); Hudson, D., et al., Int J Pept Prot Res (1979) 14:177-185 (—CH$_2$NH—, —CH$_2$CH$_2$—); Spatola, A. F., et al., Life Sci (1986) 38:1243-1249 (—CH$_2$—S); Hann, M. M., J Chem Soc Perkin Trans I (1982) 307-314 (—CH—CH—, cis and trans); Almiquist, R. G., et al., J Med Chem (1980) 23:1392-1398 (—COCH$_2$—); Jennings-White, C., et al., Tetrahedron Lett (1982) 23:2533 (—COCH$_2$—); Szelke, M., et al., European Application EP 45665 (1982) CA:97:39405 (1982) (—CH(OH)CH$_2$—); Holladay, M. W., et al., Tetrahedron Lett (1983) 24:4401-4404 (—C(OH)CH$_2$—); and Hruby, V. J., Life Sci (1982) 31: 189-199 (—CH$_2$—S—).

Amino acid residues contained within the compounds, and particularly at the carboxy- or amino-terminus, can also be modified by amidation, acetylation or substitution with other chemical groups which can, for example, change the solubility of the compounds without affecting their activity. Also, the protracted profile of the compounds can be improved by attaching a lipophilic substituent to any one or more amino acid residues of a natriuretic peptide of the invention, as for example described by Huusfeldt et al. in International Publication WO 98/45329.

It is well known that amide modified analogues of natriuretic peptides are particularly potent and are thus contemplated by the present invention. For example, the carboxy-terminal residue will have a carbonyl carbon which has been substituted with an amino group to form a carboxy-terminal amido group. In general, the nitrogen atom of the amido group, covalently bound to the carbonyl carbon, will be of the general formula —NR'R", where R' and R" are substituent groups. Each substituent group can independently be hydrogen, or an organic group such as alkyl, straight chain or branched of from one to ten, usually one to six carbon atoms, including groups having substitutions of three or less nitrogen, oxygen or sulfur atoms as amido, thio or oxy, or a benzylic group (substituted or unsubstituted), and any one of which can be a nitrogen containing moiety such as hydrazide and the other can be hydrogen, or either group can be a basic or neutral dipeptide and the other can be hydrogen or an alkyl group. Representative of such amido groups are: —NH$_2$, —NHCH$_3$, —N(CH$_3$)$_2$ and —NHCH$_2$CH$_3$, among others.

Exemplary compounds of the present invention include sequences of any naturally-occurring natriuretic peptide, obtainable from a reptilian species, especially a species of snake and more especially a species of Oxyuranus or related species, provided that they include, or are modified to include, R at position 16, a hydrophobic amino acid residue, e.g., I, L or F at position 28, and/or a small amino acid residue or basic amino acid residue, e.g., P or R, at position 32, relative to the TNPc amino acid sequence. For example, naturally occurring natriuretic peptides may be isolated from Oxyuranus microlepidotus (Inland Taipan), Oxyuranus scutellatus (Mainland or Coastal Taipan), Oxyuranus scutellatus barringeri subsp. Nov (Northwest Taipan) and Oxyuranus scutellatus canni (New Guinea Taipan).

Alternatively, a natriuretic peptide of the invention, or its fragments, can differ from the corresponding TNPc sequence. In one embodiment, it differs by at least one but by less than 15, 10, 8, 6, 5, 4, 3, 2 or 1 amino acid residues. In another, it differs from the corresponding TNPc sequence by at least one residue but less than 20%, 15%, 10% or 5% of the residues in it differ from the corresponding TNPc sequence. (If this comparison requires alignment the sequences should be aligned for maximum similarity. "Looped" out sequences from deletions or insertions, or mismatches, are considered differences.) The differences are, preferably, differences or changes at a non-essential residue or a conservative substitution.

A "non-essential" amino acid residue is a residue that can be altered from the wild-type sequence of an Oxyuranus natriuretic peptide without abolishing or substantially altering an activity of that peptide. Preferably, the alteration does not substantially alter the Oxyuranus natriuretic peptide activity, e.g., the activity is at least 20%, 40%, 60%, 70% or 80% of wild-type. An "essential" amino acid residue is a residue that, when altered from the wild-type sequence of an *Oxyuranus* natriuretic peptide, results in abolishing an *Oxyuranus* natriuretic peptide activity such that less than 20% of the wild-type activity is present. For example, conserved amino acid residues shared between the natriuretic peptides of the invention, e.g., those shown in FIG. 2, are predicted to be particularly unamenable to alteration.

A "conservative amino acid substitution" is one in which the amino acid residue is replaced with an amino acid residue having a similar side chain. Families of amino acid residues having similar side chains have been defined in the art and certain subclasses are described in Table 4. Preferred variant peptides are those having conserved amino acid substitutions. Examples of conservative substitutions include the following: aspartic-glutamic as acidic amino acids; lysine/arginine/histidine as basic amino acids; serine/glycine/alanine/threonine as small amino acids; leucine/isoleucine, methionine/valine, alanine/valine as hydrophobic amino acids. Conservative amino acid substitution also includes groupings based on side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. For example, it is reasonable to expect that replacement of a leucine with an isoleucine or valine, an aspartate with a glutamate, a threonine with a serine, or a similar replacement of an amino acid with a structurally related amino acid will not have a major effect on the properties of the resulting variant polypeptide. Whether an amino acid change results in a functional peptide can readily be determined by assaying the specific activity of the peptide variant. Conservative substitutions are shown in the Table 5 below under the heading of exemplary substitutions. More preferred substitutions are under the heading of preferred substitutions. Amino acid substitutions falling within the scope of the invention, are, in general, accomplished by selecting substitutions that do not differ significantly in their effect on maintaining (a) the structure of the peptide backbone in the area of the substitution, (b) the charge or hydrophobicity of the molecule at the target site, or (c) the bulk of the side chain. After the substitutions are introduced, the variants are screened for biological activity.

Alternatively, similar amino acids for making conservative substitutions can be grouped into three categories based on the identity of the side chains. The first group includes glutamic acid, aspartic acid, arginine, lysine, histidine, which all have charged side chains; the second group includes glycine, serine, threonine, cysteine, tyrosine, glutamine, asparagine; and the third group includes leucine, isoleucine, valine, alanine, proline, phenylalanine, tryptophan, methionine, as described in Zubay, G., *Biochemistry*, third edition, Wm.C. Brown Publishers (1993).

Thus, a predicted non-essential amino acid residue in an *Oxyuranus* natriuretic peptide is preferably replaced with another amino acid residue from the same side chain family. Alternatively, in another embodiment, mutations can be introduced randomly along all or part of an *Oxyuranus* natriuretic peptide coding sequence, such as by saturation mutagenesis, and the resultant mutants can be screened for *Oxyuranus* natriuretic peptide biological activity to identify mutants that retain activity. Following mutagenesis of such coding sequences, the encoded peptide can be expressed recombinantly and the activity of the peptide can be determined. Other methods for finding suitable NP mutants include phage display such as described, for example, in U.S. Pat. No. 6,028,055.

Other embodiments include a peptide that contains one or more changes in amino acid sequence, e.g., a change in an amino acid residue which is not essential for activity. Such natriuretic peptides differ in amino acid sequence from TNPc, yet retain biological activity.

In other embodiments, the *Oxyuranus* natriuretic peptide includes an amino acid sequence having at least about 50%, 55%, 60%, 65%, 70%, 75%, 80%, 85%, 90%, 91%, 92%, 93%, 94% 95%, 96%, 97%, 98% or more similarity to a corresponding sequence of TNPc, and has an *Oxyuranus* natriuretic peptide biological activity.

The natriuretic peptides of the invention contain a significant number of structural characteristics in common with each other as for example depicted in FIG. 2 and Table 1. The term "family" when referring to the protein and nucleic acid molecules of the invention means two or more proteins or nucleic acid molecules having a common structural domain or motif and having sufficient amino acid or nucleotide sequence homology as defined herein. Such family members can be naturally or non-naturally-occurring and can be from either the same or different species. Members of a family can also have common functional characteristics.

Variant *Oxyuranus* natriuretic peptide sequences, which differ from a parent natriuretic peptide sequence, by the substitution, addition or deletion of at least one amino acid residue may be synthesized de novo using solution or solid phase peptide synthesis techniques as known in the art. Alternatively such variants, including variants of naturally-occurring *Oxyuranus* natriuretic peptide sequences may be conveniently obtained by mutagenesis of their coding sequences. Mutations in nucleotide sequences constructed for expression of variants must, of course, preserve the reading frame phase of the coding sequences and preferably will not create complementary regions that could hybridize to produce secondary mRNA structures such as loops or hairpins which would adversely affect translation of the mRNA. Although a mutation site may be predetermined, it is not necessary that the nature of the mutation perse be predetermined. For example, in order to select for optimum characteristics of mutants at a given site, random mutagenesis may be conducted at the target codon and the expressed mutants screened for at least one activity of an *Oxyuranus* natriuretic peptide.

In one embodiment, mutations can be introduced at particular loci by synthesizing oligonucleotides encoding the desired amino acid residues, flanked by restriction sites enabling ligation to fragments of the native sequence. Following ligation, the resulting reconstructed sequence encodes a variant having the desired amino acid insertion, substitution, or deletion. In another embodiment, oligonucleotide-directed site-specific mutagenesis procedures can be employed to provide an altered nucleotide sequence having particular codons altered according to the substitution, deletion, or insertion required. Exemplary methods of making the alterations set forth above are disclosed by Walder et al. (1986, *Gene* 42:133); Bauer et al. (1985, *Gene* 37:73); Craik (1985, *BioTechniques* January 12-19); Smith et al. (Genetic Engineering: Principles and Methods, Plenum Press, 1981); and U.S. Pat. Nos. 4,518,584 and 4,737,462.

Sources of nucleotide sequences from which nucleic acid molecules encoding the natriuretic peptides of the invention, or their nucleic acid complements, can be obtained include total or polyA$^+$ RNA from a reptilian species, e.g., snake, more preferably from a species of *Oxyuranus* from which cDNAs can be derived by methods known in the art. Other sources of the DNA molecules of the invention include genomic libraries derived from an appropriate cellular source.

A nucleic acid molecule encoding a native *Oxyuranus* natriuretic peptide can be identified and isolated using standard methods, as described by Sambrook et al. *Molecular Cloning—A Laboratory Manual*, Second Ed., Cold Spring Harbor Press (1989); and Ausubel et al., *Current Protocols in Molecular Biology*, John Wiley & Sons, Inc. (1998). For example, reverse-transcriptase PCR (RT-PCR) can be employed to isolate and clone natriuretic peptide cDNAs. Oligo-dT can be employed as a primer in a reverse transcriptase reaction to prepare first-strand cDNAs from isolated RNA which contains RNA sequences of interest, e.g., total RNA isolated from human tissue. Resultant first-strand cDNAs can then be amplified by a suitable nucleic acid amplification reaction such as the Polymerase Chain Reaction (or PCR) as known in the art. Primers, which are optionally degenerate, are designed to correspond to highly conserved regions of the natriuretic peptides or nucleotide sequences which were identified and compared to generate the primers. The products of each amplification reaction are typically separated via agarose gel electrophoresis and all consistently amplified products are gel-purified and cloned directly into a suitable vector for subsequent sequence analysis of the cloned amplified products.

Another approach to identify, isolate and clone natriuretic peptide-encoding cDNAs is to screen a cDNA library. Screening for DNA fragments that encode all or a portion of a cDNA that codes for a natriuretic peptide can be accomplished by probing the library with a probe which has sequences that are highly conserved between genes believed to be related to the natriuretic peptide, e.g., the homologue of a particular natriuretic peptide from a different species, or by screening of plaques for binding to antibodies that specifically recognize a natriuretic peptide, such as antibodies that recognize the highly conserved central core of natriuretic peptides. DNA fragments that bind to a probe having sequences which are related to natriuretic peptide, or which encode amino acid sequences that are immuno-interactive with antibodies to natriuretic peptide, can be subcloned into a suitable vector and sequenced and/or used as probes to identify other cDNAs encoding all or a portion of the natriuretic peptide.

Thus, the present invention contemplates isolated nucleic acid molecules comprising a sequence that encodes a natriuretic peptide of the invention. In certain embodiments, an isolated nucleic acid molecule of the invention hybridizes under a stringency condition described herein to a naturally-occurring nucleic acid molecule that encodes a natriuretic peptide of the invention. As used herein, the term "hybridizes under low stringency, medium stringency, high stringency, or very high stringency conditions" describes conditions for hybridization and washing. Guidance for performing hybridization reactions can be found in Ausubel et al., (1998, supra), Sections 6.3.1-6.3.6. Aqueous and nonaqueous methods are described in that reference and either can be used. Specific hybridization conditions referred to herein are as follows: 1) low stringency hybridization conditions in 6x sodium chloride/sodium citrate (SSC) at about 45° C., followed by two washes in 0.2xSSC, 0.1% SDS at least at 50° C. (the temperature of the washes can be increased to 55° C. for low stringency conditions); 2) medium stringency hybridization conditions in 6xSSC at about 45° C., followed by one or more washes in 0.2xSSC, 0.1% SDS at 60° C.; 3) high stringency hybridization conditions in 6xSSC at about 45° C., followed by one or more washes in 0.2xSSC, 0.1% SDS at 65° C.; and preferably 4) very high stringency hybridization conditions are 0.5M sodium phosphate, 7% SDS at 65° C., followed by one or more washes at 0.2xSSC, 1% SDS at 65° C. Very high stringency conditions (4) are the preferred conditions and the ones that should be used unless otherwise specified.

Other stringency conditions are well known in the art and a skilled addressee will recognize that various factors can be manipulated to optimize the specificity of the hybridization. Optimization of the stringency of the final washes can serve to ensure a high degree of hybridization. For detailed examples, see Ausubel et al., supra at pages 2.10.1 to 2.10.16 and Sambrook et al. (1989, supra) at sections 1.101 to 1.104. While stringent washes are typically carried out at temperatures from about 42° C. to 68° C., one skilled in the art will appreciate that other temperatures may be suitable for stringent conditions. Maximum hybridization rate typically occurs at about 20° C. to 25° C. below the $T_m$ for formation of a DNA-DNA hybrid. It is well known in the art that the $T_m$ is the melting temperature, or temperature at which two complementary polynucleotide sequences dissociate. Methods for estimating $T_m$ are well known in the art (see Ausubel et al., supra at page 2.10.8).

In general, the $T_m$ of a perfectly matched duplex of DNA may be predicted as an approximation by the formula:

$$T_m = 81.5 + 16.6(\log_{10} M) + 0.41(\% G+C) - 0.63 (\% \text{formamide}) - (600/\text{length}),$$

wherein: M is the concentration of $Na^+$, preferably in the range of 0.01 molar to 0.4 molar; % G+C is the sum of guanosine and cytosine bases as a percentage of the total number of bases, within the range between 30% and 75% G+C; % formamide is the percent formamide concentration by volume; length is the number of base pairs in the DNA duplex.

The $T_m$ of a duplex DNA decreases by approximately 1° C. with every increase of 1% in the number of randomly mismatched base pairs. Washing is generally carried out at $T_m - 15°$ C. for high stringency, or $T_m - 30°$ C. for moderate stringency.

The invention also contemplates derivatives of the naturally-occurring or variant natriuretic peptides disclosed herein or their biologically active portions, which have been derived from a parent sequence by modification, for example by conjugation or complexing with other chemical moieties. Such derivatives include fusions of such natriuretic peptides of the invention with other peptides or polypeptides. For example, amino acid sequence, which display at least one natriuretic peptide activity may be fused to a further protein, for example, which is not derived from the original host. The further protein may assist in the purification of the fusion protein. For instance, a polyhistidine tag or a maltose binding protein may be used in this respect as described in more detail below. Other possible fusion proteins are those which produce an immunomodulatory response. Particular examples of such proteins include Protein A or glutathione S-transferase (GST).

Other derivatives include, but are not limited to, modification to side chains, incorporation of unnatural amino acids and/or their derivatives during peptide, polypeptide or protein synthesis and the use of crosslinkers and other methods which impose conformational constraints on the peptides, portions and variants of the invention. Examples of side chain modifications include modifications of amino groups such as by acylation with acetic anhydride; acylation of amino groups with succinic anhydride and tetrahydrophthalic anhydride; amidination with methylacetimidate; carbamoylation of amino groups with cyanate; pyridoxylation of lysine with pyridoxal-5-phosphate followed by reduction with $NaBH_4$; reductive alkylation by reaction with an aldehyde followed by reduction with $NaBH_4$; and trinitrobenzylation of amino groups with 2,4,6-trinitrobenzene sulphonic acid (TNBS).

The carboxyl group may be modified by carbodiimide activation via O-acylisourea formation followed by subsequent derivatisation, by way of example, to a corresponding amide.

The guanidine group of arginine residues may be modified by formation of heterocyclic condensation products with reagents such as 2,3-butanedione, phenylglyoxal and glyoxal.

Sulfhydryl groups may be modified by methods such as performic acid oxidation to cysteic acid; formation of mercurial derivatives using 4-chloromercuriphenylsulphonic acid, 4-chloromercuribenzoate; 2-chloromercuri-4-nitrophenol, phenylmercury chloride, and other mercurials; formation of a mixed disulfides with other thiol compounds; reaction with maleimide, maleic anhydride or other substituted maleimide; carboxymethylation with iodoacetic acid or iodoacetamide; and carbamoylation with cyanate at alkaline pH.

Tryptophan residues may be modified, for example, by alkylation of the indole ring with 2-hydroxy-5-nitrobenzyl bromide or sulphonyl halides or by oxidation with N-bromosuccinimide.

Tyrosine residues may be modified by nitration with tetranitromethane to form a 3-nitrotyrosine derivative.

The imidazole ring of a histidine residue may be modified by N-carbethoxylation with diethylpyrocarbonate or by alkylation with iodoacetic acid derivatives.

Examples of incorporating unnatural amino acids and derivatives during peptide synthesis include but are not limited to, use of 4-amino butyric acid, 6-aminohexanoic acid, 4-amino-3-hydroxy-5-phenylpentanoic acid, 4-amino-3-hydroxy-6-methylheptanoic acid, t-butylglycine, norleucine, norvaline, phenylglycine, ornithine, sarcosine, 2-thienyl alanine and/or D-isomers of amino acids. A list of unnatural amino acids contemplated by the present invention is shown in Table 6.

The invention also contemplates chimeric natriuretic peptides that correspond to all or a portion e.g., a portion described herein of a natriuretic peptide amino acid sequence. In specific embodiments, a chimeric natriuretic peptide includes at least one (or two) biologically active portion(s) of a natriuretic peptide of the invention. In certain embodiments, it will include at least one biologically active portion of a natriuretic peptide of the invention and at least one biologically active portion of another natriuretic peptide, e.g., from ANP, BNP, CNP or DNP or their variants. Chimeric natriuretic peptides may be prepared, for example, by using recombinant DNA based methodologies or chemical syntheses. For example, nucleic acid molecules encoding chimeric natriuretic peptides can be synthesized de novo using readily available machinery. Sequential synthesis of DNA is described, for example, in U.S. Pat. No. 4,293,652. Instead of de novo synthesis, recombinant techniques may be employed including use of restriction endonucleases to cleave different natriuretic peptide-encoding polynucleotides and use of ligases to ligate together in frame a plurality of cleaved polynucleotides encoding selected portions of the different natriuretic peptides. Suitable recombinant techniques are described for example in the relevant sections of Ausubel, et al. (supra) and of Sambrook, et al., (supra). Preferably, the synthetic polynucleotide is constructed using splicing by overlapping extension (SOEing) as for example described by Horton et al. (1990, *Biotechniques* 8(5): 528-535; 1995, *Mol. Biotechnol.* 3(2): 93-99; and 1997, *Methods Mol. Biol.* 67: 141-149). However, it should be noted that the present invention is not dependent on, and not directed to, any one particular technique for constructing the synthetic construct.

The invention therefore contemplates a method of producing a synthetic polynucleotide as broadly described above, comprising linking together in the same reading frame at least two nucleic acid sequences, wherein individual nucleic acid sequences encode a portion of a distinct natriuretic peptide to form a synthetic polynucleotide, which encodes a chimeric natriuretic peptide according to the invention.

3. Preparation of Natriuretic Peptides of the Invention

The subject natriuretic peptides can be prepared by a process including fractionating venom from a suitable source as described above, and testing fractions thus produced for an activity selected from natriuretic, diuretic, renin-suppressing, bactericidal, weight-reducing and/or bone growth plate size-increasing activities. Assays for testing such activities are well known to persons of skill in the art and include aortic ring contraction/relaxation assays, cell cycle GMP elevation assays (see, for instance, Examples 3 and 4, respectively) and natriuretic peptide receptor binding assays (as described, for example, in Ballermann B J, 1988 *Am Journal of Physiology* 254: F159-163; Burgisser et al., 1985, *Biochemical and Biophysical Research Communications* 133:1201-1209; Capper et al., 1990, *Clinical Chemistry* 36:656-658; Gutkowska et al., 1988, *Analytical Biochemistry* 168:100-106). Examples of such assays are given in anesthetized or conscious rat and rabbit blood pressure assay, left coronary artery ligation induced heart failure in the rat, pacing induced heart failure of the sheep. An illustrative bioassay for quantification of atrial natriuretic polypeptides in rat is described by Matsui et al., 1987, *Am J Physiol* 252:R1009-14. Optionally, the fractions are purified further to provide natriuretic peptides in substantially purified form. Isolated or chemically synthesized peptides can be tested in vivo for effects on blood pressure and heart rate using methods as described, for instance, in Example 8-10. Appropriate animal models for testing and evaluating cardiorenal properties and the effectiveness of compounds in treating heart failure are known in the art and include canine (Burnett & Lisy, WO 01/44284), rat (Arabia et al., 2002, *Neuroscience* 114:3:591-599) and ovine models (Byrne et al., 2002, *Journal of Cardiac Failure* 8, 2: 108-115). Stability of the NPs can be measured against a range of enzymes including NEP24.11 and trypsin, using well established methods (see for example Lew, R. *Methods in Molecular Biology* 2 51, H P L C of Peptides and Proteins: Methods and Protocols; Aguilar, Mich. (Ed), Humana Press Inc., Totowa, N.J.).

Peptides of the present invention can be synthesized by solution or solid phase synthesis methods as known in the art. For example, the widely used Merrifield solid phase synthesis method, including the experimental procedures, is described in the following references: Stewart et al. (1969, Solid Phase Peptide Synthesis, W. H. Freeman Co., San Francisco); Merrifield (1963, *J Am Chem Soc* 85: 2149); Meinenhofer (1973, *Int J Pept Pro Res* 11: 246); and Barany and Merrifield (1980, in *The Peptides*, E. Gross and F. Meinenhofer, eds., Vol. 2, Academic Press, pp. 3-285). These standard peptide synthetic methods are followed by oxidative disulfide bond formation. For example, the linear peptides may be synthesized by solid phase methodology using BOC chemistry, as described by Schnoltzer et al., (1992, *Int J Pept Prot Res* 40, 180-193). Following deprotection and cleavage from the solid support the reduced peptides are purified using preparative chromatography. The purified reduced peptides are oxidized in buffered systems. The oxidized peptides are purified using preparative chromatography (e.g. Example 2 infra) using well documented procedures.

General references describing the synthesis of natriuretic peptides and derivatives thereof include Craik et al. (1991, *Eur. J. Biochem.* 201: 183-190); WO89/09611 and WO90/00561.

Replacement of the disulfide bridges with diselenide or mixed sulfide-selenide bridges can be done using the methods of Koide et al. (1993, *Chem. Pharm. Bull* 41: 502-505) or Pegoraro et al. (1998, *J. Mol. Biol.*, 284: 779-792).

A disulfide bridge can also be replaced by a lanthionine bridge as described for example by Li et al. (2002, *Current Organic Chemistry*, 6: 411-440) or by a dimethylene bridge using standard protocols known in the art.

Salts of carboxyl groups of the synthesized peptides may be prepared by contacting the peptide with one or more equivalents of a desired base such as, for example, a metallic hydroxide base, e.g., sodium hydroxide; a metal carbonate or bicarbonate base such as, for example, sodium carbonate or sodium bicarbonate; or an amine base such as, for example, triethylamine, triethanolamine, and the like.

Acid addition salts of the synthesized peptides may be prepared by contacting the polypeptide with one or more equivalents of the desired inorganic or organic acid, such as, for example, hydrochloric acid.

Amides of the synthesized peptides of the present invention may also be prepared by techniques well known in the art for converting a carboxylic acid group or precursor, to an amide. A suitable method for amide formation at the C-terminal carboxyl group is to cleave the polypeptide from a solid support with an appropriate amine, or to cleave in the presence of an alcohol, yielding an ester, followed by aminolysis with the desired amine.

Esters of carboxyl groups of the synthesized peptides may be prepared by any of the usual means known in the art for converting a carboxylic acid or precursor to an ester. One suitable method for preparing esters of the subject peptides, when using the Merrifield synthesis technique, is to cleave the completed polypeptide from the resin in the presence of the desired alcohol either under basic or acidic conditions, depending upon the resin. Thus, the C-terminal end of the peptide when freed from the resin is directly esterified without isolation of the free acid.

N-acyl derivatives of an amino group of synthesized peptides may be prepared by utilizing an N-acyl protected amino acid for the final condensation, or by acylating a protected or unprotected peptide. O-acyl derivatives may be prepared for example, by acylation of a free hydroxy peptide or peptide resin. Either acylation may be carried out using standard acylating reagent such as acyl halides, anhydrides, acyl imidazoles, and the like. Both N- and O-acylation may be carried out together, if desired.

PEGylated derivatives and similar conjugates of TNPs and analogues can be prepared by methods used for other NPs (WO2004/047871).

The synthesis may use manual techniques or be completely automated, employing, for example, an Applied BioSystems 431A Peptide Synthesizer (Foster City, Calif.) or a Biosearch SAM II automatic peptide synthesizer (Biosearch, Inc., San Rafael, Calif.), following the instructions provided in the instruction manual and reagents supplied by the manufacturer. Disulfide bonds between Cys residues can be introduced by mild oxidation of the linear peptide by KCN as taught, for example, in U.S. Pat. No. 4,757,048 at Col. 20.

Alternatively, the natriuretic peptides of the invention may be prepared by a recombinant DNA technique. For example, natriuretic peptides may be prepared by a process including the steps of (a) preparing a recombinant polynucleotide comprising a nucleotide sequence encoding a natriuretic peptide of the invention, which nucleotide sequence is operably linked to a regulatory sequence; (b) introducing the recombinant polynucleotide into a suitable host cell; (c) culturing the host cell to express recombinant peptide from the recombinant polynucleotide; and (d) isolating the recombinant peptide. In certain embodiments, the nucleotide sequence encodes at least a portion of the TNPc amino acid sequence set forth in SEQ ID NO: 90, or its fragments, variants and derivatives, illustrative examples of which are set forth in SEQ ID NO: 1-7, 15-81 supra and in SEQ ID NO: 91, 94-114, 117, 118, 120, 123, 124, 126-130, 132-134, 150, 154, 160, 166-169, 173, 176 and 178-182 (see Table 2).

The recombinant polynucleotide is suitably in the form of an expression vector, which can be a self-replicating extra-chromosomal vector such as a plasmid, or a vector that integrates into a host genome. The regulatory sequences will generally need to be appropriate for the host cell used for expression. Numerous types of appropriate expression vectors and suitable regulatory sequences are known in the art for a variety of host cells. Typically, the regulatory sequences include, but are not limited to, promoter sequences, leader or signal sequences, ribosomal binding sites, transcriptional start and stop sequences, translational start and termination sequences, and enhancer or activator sequences. Constitutive or inducible promoters as known in the art are contemplated by the invention. The promoters may be either naturally occurring promoters, or hybrid promoters that combine elements of more than one promoter.

In certain embodiments, the expression vector contains a selectable marker gene to allow the selection of transformed host cells. Selectable marker genes are well known in the art and will vary with the host cell used.

The expression vector may also include a fusion partner (typically provided by the expression vector) so that the recombinant peptide of the invention is expressed as a fusion polypeptide with said fusion partner. The main advantage of fusion partners is that they assist identification and/or purification of said fusion polypeptide. In order to express the fusion polypeptide, it is necessary to ligate a polynucleotide according to the invention into the expression vector so that the translational reading frames of the fusion partner and the polynucleotide coincide. Well known examples of fusion partners include, but are not limited to, glutathione-S-transferase (GST), Fc portion of human IgG, maltose binding protein (MBP) and hexahistidine ($HIS_6$), which are particularly useful for isolation of the fusion polypeptide by affinity chromatography. For the purposes of fusion polypeptide purification by affinity chromatography, relevant matrices for affinity chromatography include, but are not restricted to, glutathione-, amylose-, and nickel- or cobalt-conjugated resins. Many such matrices are available in "kit" form, such as the QIAexpress™ system (Qiagen) useful with ($HIS_6$) fusion partners and the Pharmacia GST purification system. In one embodiment, the recombinant polynucleotide is expressed in the commercial vector pFLAG. Another fusion partner well known in the art is green fluorescent protein (GFP). This fusion partner serves as a fluorescent "tag" which allows the fusion polypeptide of the invention to be identified by fluorescence microscopy or by flow cytometry. The GFP tag is useful when assessing subcellular localization of the fusion polypeptide of the invention, or for isolating cells which express the fusion polypeptide of the invention. Flow cytometric methods such as fluorescence activated cell sorting (FACS) are particularly useful in this latter application. Suitably, the fusion partners also have protease cleavage sites, such as for Factor $X_a$ or Thrombin, which allow the relevant protease to partially digest the fusion polypeptide of the invention and thereby liberate the recombinant polypeptide of the invention therefrom. The liberated polypeptide can then be isolated from the fusion partner by subsequent chromatographic separation. Fusion partners according to the invention also include within their scope "epitope tags", which are usually short peptide sequences for which a specific antibody is available. Well known examples of epitope tags for which specific monoclonal antibodies are readily available include c-Myc, influenza virus, hemagglutinin and FLAG tags.

The step of introducing the recombinant polynucleotide into a host cell may be achieved by any suitable method including transfection, and transformation, the choice of which will be dependent on the host cell employed. Such methods are well known to those of skill in the art.

Recombinant polypeptides of the invention may be produced by culturing a host cell transformed with an expression vector containing nucleic acid encoding a natriuretic peptide the invention. The conditions appropriate for protein expression will vary with the choice of expression vector and the host cell. This is easily ascertained by one skilled in the art through routine experimentation.

Suitable host cells for expression may be prokaryotic or eukaryotic. One preferred host cell for expression of a polypeptide according to the invention is a bacterium. The bacterium used may be *Escherichia coli*. Alternatively, the host cell may be an insect cell such as, for example, SF9 cells that may be utilized with a baculovirus expression system.

The recombinant protein may be conveniently prepared by a person skilled in the art using standard protocols as for example described in Sambrook, et al., (1989, supra), in particular Sections 16 and 17; Ausubel et al., (1998, supra), in particular Chapters 10 and 16; and Coligan et al., CURRENT PROTOCOLS IN PROTEIN SCIENCE (John Wiley & Sons, Inc. 1995-1997), in particular Chapters 1, 5 and 6.

After preparation, the recombinant peptides/polypeptides are tested for their capacity to display at least one activity selected from vasodilatory, natriuretic, diuretic, renin-suppressing, bactericidal, weight-reducing or bone growth plate size-increasing activities, using any suitable assay known to persons of skill in the art.

4. Anti-natriuretic Peptide Antigen-binding Molecules

The invention also provides an antigen-binding molecule that is specifically immuno-interactive with an *Oxyuranus* natriuretic peptide. In one embodiment, the antigen-binding molecules comprise whole polyclonal antibodies. Such antibodies may be prepared, for example, by injecting a polypeptide, fragment, variant or derivative of the invention into a production species, which may include mice or rabbits, to obtain polyclonal antisera. Methods of producing polyclonal antibodies are well known to those skilled in the art. Exemplary protocols which may be used are described for example in Coligan et al., CURRENT PROTOCOLS IN IMMUNOLOGY, (John Wiley & Sons, Inc, 1991), and Ausubel et al., (1994-1998, supra), in particular Section III of Chapter 11.

In lieu of polyclonal antisera obtained in a production species, monoclonal antibodies may be produced using the standard method as described, for example, by Köhler and Milstein (1975, *Nature* 256, 495-497), or by more recent modifications thereof as described, for example, in Coligan et al., (1991, supra) by immortalizing spleen or other antibody producing cells derived from a production species which has been inoculated with one or more of the polypeptides, fragments, variants or derivatives of the invention.

The invention also contemplates as antigen-binding molecules Fv, Fab, Fab' and F(ab')$_2$ immunoglobulin fragments. Alternatively, the antigen-binding molecule may comprise a synthetic stabilized Fv fragment. Exemplary fragments of this type include single chain Fv fragments (sFv, frequently termed scFv) in which a peptide linker is used to bridge the N terminus or C terminus of a V$_H$ domain with the C terminus or N-terminus, respectively, of a V$_L$ domain. ScFv lack all constant parts of whole antibodies and are not able to activate complement. Suitable peptide linkers for joining the V$_H$ and V$_L$ domains are those which allow the V$_H$ and V$_L$ domains to fold into a single polypeptide chain having an antigen binding site with a three dimensional structure similar to that of the antigen binding site of a whole antibody from which the Fv fragment is derived. Linkers having the desired properties may be obtained by the method disclosed in U.S. Pat. No. 4,946,778. However, in some cases a linker is absent. ScFvs may be prepared, for example, in accordance with methods outlined in Kreber et al (Kreber et al. 1997, *J. Immunol. Methods;* 201(1): 35-55). Alternatively, they may be prepared by methods described in U.S. Pat. No. 5,091,513, European Patent No 239,400 or the articles by Winter and Milstein (1991, *Nature* 349:293) and Plückthun et al (1996, *In Antibody engineering: A practical approach.* 203-252).

In another embodiment, the synthetic stabilized Fv fragment comprises a disulfide stabilized Fv (dsFv) in which cysteine residues are introduced into the V$_H$ and V$_L$ domains such that in the fully folded Fv molecule the two residues will form a disulfide bond therebetween. Suitable methods of producing dsFv are described for example in (Glockscuther et al. *Biochem.* 29: 1363-1367; Reiter et al. 1994, *J. Biol. Chem.* 269: 18327-18331; Reiter et al. 1994, *Biochem.* 33: 5451-5459; Reiter et al. 1994. *Cancer Res.* 54: 2714-2718; Webber et al. 1995, *Mol. Immunol.* 32: 249-258).

Also contemplated as antigen-binding molecules are single variable region domains (termed dAbs) as for example disclosed in Ward et al. (1989, *Nature* 341: 544-546); Hamers-Casterman et al. (1993, *Nature*. 363: 446-448); Davies & Riechmann, (1994, *FEBS Lett.* 339: 285-290). Alternatively, the antigen-binding molecule may comprise a "minibody". In this regard, minibodies are small versions of whole antibodies, which encode in a single chain the essential elements of a whole antibody. Suitably, the minibody is comprised of the V$_H$ and V$_L$ domains of a native antibody fused to the hinge region and CH3 domain of the immunoglobulin molecule as, for example, disclosed in U.S. Pat. No. 5,837,821.

In an alternate embodiment, the antigen binding molecule may comprise non-immunoglobulin derived, protein frameworks. For example, reference may be made to Ku & Schultz, (1995, *Proc. Natl. Acad. Sci. USA*, 92: 652-6556) which discloses a four-helix bundle protein cytochrome b562 having two loops randomized to create complementarity determining regions (CDRs), which have been selected for antigen binding.

The antigen-binding molecule may be multivalent (i.e., having more than one antigen binding site). Such multivalent molecules may be specific for one or more antigens. Multivalent molecules of this type may be prepared by dimerisation of two antibody fragments through a cysteinyl-containing peptide as, for example disclosed by Adams et al., (1993, *Cancer Res.* 53: 4026-4034) and Cumber et al. (1992, *J. Immunol.* 149: 120-126). Alternatively, dimerisation may be facilitated by fusion of the antibody fragments to amphiphilic helices that naturally dimerise (Pack P. Plünckthun, 1992, *Biochem.* 31: 1579-1584), or by use of domains (such as the leucine zippers jun and fos) that preferentially heterodimerise (Kostelny et al., 1992, *J. Immunol.* 148: 1547-1553). In an alternate embodiment, the multivalent molecule may comprise a multivalent single chain antibody (multi-scFv) comprising at least two scFvs linked together by a peptide linker. In this regard, non-covalently or covalently linked scFv dimers termed "diabodies" may be used. Multi-scFvs may be bispecific or greater depending on the number of scFvs employed having different antigen binding specificities. Multi-scFvs may be prepared for example by methods disclosed in U.S. Pat. No. 5,892,020.

Phage display and combinatorial methods for generating natriuretic peptide antigen-binding molecules are known in the art (as described in, e.g., Ladner et al. U.S. Pat. No. 5,223,409; Kang et al. International Publication No. WO 92/18619; Dower et al. International Publication No. WO 91/17271; Winter et al. International Publication WO 92/20791; Markland et al. International Publication No. WO 92/15679; Breitling et al. International Publication WO 93/01288; McCafferty et al. International Publication No. WO 92/01047; Garrard et al. International Publication No. WO 92/09690; Ladner et al. International Publication No. WO 90/02809; Fuchs et al. (1991) *Bio/Technology* 9:1370-1372; Hay et al., 1992, *Hum Anihbod Hybridomas* 3:81-85; Huse et al., 1989, *Science* 246:1275-1281; Griffths et al., 1993, *EMBO J.* 12:725-734; Hawkins et al., 1992, *J Mol Biol* 226:889-896; Clackson et al., 1991, *Nature* 352:624-628; Gram et al., 1992, Proc. Natl. Acad. Sci. USA 89:3576-3580; Garrad et al., 1991, *Bio/Technology* 9:1373-1377; Hoogenboom et al., 1991, *Nucleic Acid Res* 19:4133-4137; and Barbas et al., 1991, *Proc. Natl. Acad. Sci. USA* 88:7978-7982).

The antigen-binding molecules can be used to screen expression libraries for variant natriuretic peptides of the invention as described herein. They can also be used to detect and/or isolate the natriuretic peptides of the invention. Thus, the invention also contemplates the use of antigen-binding molecules to isolate *Oxyuranus* natriuretic peptides using, for example, any suitable immunoaffinity based method including, but not limited to, immunochromatography and immunoprecipitation. A preferred method utilizes solid phase adsorption in which anti-natriuretic peptide antigen-binding molecules are attached to a suitable resin, the resin is contacted with a sample suspected of containing a natriuretic peptides, and the natriuretic peptides, if any, are subsequently eluted from the resin. Preferred resins include: Sepharose® (Pharmacia), Poros® resins (Roche Molecular Biochemicals, Indianapolis), Actigel Superflow™ resins (Sterogene Bioseparations Inc., Carlsbad Calif.), and Dynabeads™ (Dynal Inc., Lake Success, N.Y.).

Preferred epitopes encompassed by the antigenic peptide are regions of *Oxyuranus* natriuretic peptides which are located in the N-terminal, central core and especially C-terminal portions, as well as regions with high antigenicity.

The antigen-binding molecule can be coupled to a compound, e.g., a label such as a radioactive nucleus, or imaging agent, e.g. a radioactive, enzymatic, or other, e.g., imaging agent, e.g., a NMR contrast agent. Labels which produce detectable radioactive emissions or fluorescence are preferred.

An anti-natriuretic peptide antigen-binding molecule (e.g., monoclonal antibody) can be used to isolate a natriuretic peptide by standard techniques, such as affinity chromatography or immunoprecipitation. Moreover, an anti-natriuretic peptide antigen-binding molecule can be used to detect natriuretic peptides (e.g., in a cellular lysate or cell supernatant) in order to evaluate the abundance and pattern of expression of the protein. Anti-natriuretic peptide antigen-binding molecules can be used diagnostically to monitor natriuretic peptide levels in tissue as part of a clinical testing procedure (e.g., for the diagnosis, prognosis or monitoring of congestive heart failure). Detection can be facilitated by coupling (i.e., physically linking) the antibody to a detectable substance (i.e., antibody labeling). Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^3H$.

The label may be selected from a group including a chromogen, a catalyst, an enzyme, a fluorophore, a chemiluminescent molecule, a lanthanide ion such as Europium ($Eu^{34}$), a radioisotope and a direct visual label. In the case of a direct visual label, use may be made of a colloidal metallic or non-metallic particle, a dye particle, an enzyme or a substrate, an organic polymer, a latex particle, a liposome, or other vesicle containing a signal producing substance and the like.

A large number of enzymes useful as labels is disclosed in U.S. Pat. No. 4,366,241, U.S. Pat. No. 4,843,000, and U.S. Pat. No. 4,849,338. Enzyme labels useful in the present invention include alkaline phosphatase, horseradish peroxidase, luciferase, P-galactosidase, glucose oxidase, lysozyme, malate dehydrogenase and the like. The enzyme label may be used alone or in combination with a second enzyme in solution.

5. Pharmaceutical Compositions

The invention also provides pharmaceutical compositions that include a natriuretic peptide of the invention and a pharmaceutically acceptable carrier, excipient and/or diluent. The pharmaceutical compositions of the invention can be used to promote or otherwise facilitate at least one activity selected from vasodilatory, natriuretic, diuretic, renin-suppressing, bactericidal, weight-reducing or bone growth plate size-increasing activities, in vertebrate animals including mammals. Accordingly, the compositions are considered useful for treating or preventing a variety of conditions including edematous states such as heart failure, nephrotic syndrome, cirrhosis of the liver, hypertension, kidney failure and the like, bacterial infections, asthma, weight loss, inflammatory-related diseases, erectile dysfunction, hypercholesterolemia, skeletal dysplasias and as a protectant for toxicity of anti-cancer drugs.

The peptide compounds may be formulated into the compositions as neutral or salt forms. Pharmaceutically acceptable non-toxic salts include the acid addition salts (formed with the free amino groups) and which are formed by reaction with inorganic acids such as, for example, hydrochloric, sulfuric or phosphoric acids, or organic acids such as, for example, acetic, oxalic, tartaric, mandelic, citric, malic, and the like. Salts formed with the free carboxyl groups may be derived from inorganic bases such as, for example, sodium, potassium, ammonium, calcium, or ferric hydroxides, and such organic bases such as amines, i.e., isopropylamine, trimethylamine, 2-ethylamino ethanol, histidine, procaine, and the like.

The natriuretic peptides of the invention are suitably administered to a subject, e.g., a human or a non-human mammal, such as a domestic animal, at dosages of at least about 0.01 to about 100 mg/kg, more preferably about 0.05 to about 50 mg/kg, and even more preferably about 0.1 to about 30 mg/kg, of body weight (e.g., about 10 to about 50 ng/kg in dogs), although other dosages may provide beneficial results.

The amount administered will vary depending on various factors including, but not limited to, the agent chosen, the disease, and whether prevention or treatment is to be achieved. Both local and systemic administration are envisioned. Systemic administration is preferred. Thus, administration of the therapeutic agents in accordance with the present invention may be continuous or intermittent, depending, for example, upon the recipient's physiological condition, whether the purpose of the administration is therapeutic or prophylactic, and other factors known to skilled practitioners. The administration of the agents of the invention may be essentially continuous over a preselected period of time or may be in a series of spaced doses.

One or more suitable unit dosage forms comprising a natriuretic peptide of the invention, which may optionally be formulated for sustained release, can be administered by a variety of routes including oral, or parenteral, including by rectal, buccal, vaginal and sublingual, transdermal, subcutaneous, intravenous, intramuscular, intraperitoneal, intrathoracic, intracoronary, intrapulmonary and intranasal routes. The formulations may, where appropriate, be conveniently presented in discrete unit dosage forms and may be prepared by any of the methods well known to pharmacy. Such methods may include the step of bringing into association the therapeutic agent with liquid carriers, solid matrices, semi-solid carriers, finely divided solid carriers or combinations thereof, and then, if necessary, introducing or shaping the product into the desired delivery system.

When the natriuretic peptide of the invention is prepared for oral administration, it is preferably combined with a pharmaceutically acceptable carrier, diluent or excipient to form a pharmaceutical formulation, or unit dosage form. The total active ingredients in such formulations comprise from 0.1 to 99.9% by weight of the formulation. By "pharmaceutically acceptable" it is meant the carrier, diluent, excipient, and/or salt must be compatible with the other ingredients of the formulation, and not deleterious to the recipient thereof. The active ingredient for oral administration may be present as a powder or as granules; as a solution, a suspension or an emulsion; or in achievable base such as a synthetic resin for ingestion of the active ingredients from a chewing gum. The active ingredient may also be presented as a bolus, electuary or paste. A useful reference describing pharmaceutically acceptable carriers, diluents and excipients is Remington's Pharmaceutical Sciences (Mack Publishing Co. N.J. USA, 1991) which is incorporated herein by reference. Supplementary active compounds can also be incorporated into the compositions.

Pharmaceutical formulations containing the natriuretic peptide of the invention can be prepared by procedures known in the art using well known and readily available ingredients. For example, the natriuretic peptide can be formulated with common excipients, diluents, or carriers, and formed into tablets, capsules, suspensions, powders, and the like. Examples of excipients, diluents, and carriers that are suitable for such formulations include the following fillers and extenders such as starch, sugars, mannitol, and silicic derivatives; binding agents such as carboxymethyl cellulose, HPMC and other cellulose derivatives, alginates, gelatin, and polyvinyl-pyrrolidone; moisturising agents such as glycerol; disintegrating agents such as calcium carbonate and sodium bicarbonate; agents for retarding dissolution such as paraffin; resorption accelerators such as quaternary ammonium compounds; surface active agents such as cetyl alcohol, glycerol monostearate; adsorptive carriers such as kaolin and bentonite; and lubricants such as talc, calcium and magnesium stearate, and solid polyethyl glycols.

For example, tablets or caplets containing the nucleic acid molecule or peptide of the invention can include buffering agents such as calcium carbonate, magnesium oxide and magnesium carbonate. Caplets and tablets can also include inactive ingredients such as cellulose, pregelatinized starch, silicon dioxide, hydroxy propyl methyl cellulose, magnesium stearate, microcrystalline cellulose, starch, talc, titanium dioxide, benzoic acid, citric acid, corn starch, mineral oil, polypropylene glycol, sodium phosphate, and zinc stearate, and the like. Hard or soft gelatin capsules containing the nucleic acid molecule or peptide of the invention can contain inactive ingredients such as gelatin, microcrystalline cellulose, sodium lauryl sulfate, starch, talc, and titanium dioxide, and the like, as well as liquid vehicles such as polyethylene glycols (PEGs) and vegetable oil. Moreover, enteric coated caplets or tablets of the nucleic acid molecule or peptide of the invention are designed to resist disintegration in the stomach and dissolve in the more neutral to alkaline environment of the duodenum.

In some embodiments, a natriuretic peptide of the invention is the only component present in the pharmaceutical composition. In some embodiments, the pharmaceutical composition can include an additional component or adjuvant. For example, the composition can include one or more of: an anti-microbial, e.g., an antibiotic, an antiviral, an antifungal, an antiparasitic agent, an anti-inflammatory agent, an antihistamine, an anti-fibrolytic agent, and a growth factor. Examples of antibiotics include tetracycline, ciprofloxacin, gentamycin, cyclosporin cefotaxim, and the like. Examples of antivirals include gangcyclovir, zidovudine, amantidine, vidarabine, ribaravin, trifluridine, acyclovir, dideoxyuridine, and the like. Antifungals include, but are not limited to, diflucan, ketaconizole, nystatin, and the like. Antiparasitic agents such as pentamidine can be included. The composition may further include an anti-inflammatory agent such as I-1-antitrypsin, I-1-antichymotrypsin, and the like. Other compounds that can be included in the composition include anesthetics, e.g., local anesthetics.

The pharmaceutical composition can be formulated to promote stability of a natriuretic peptide of the invention, e.g., to reduce digestion, e.g., autodigestion, of the natriuretic peptide. The stability of the natriuretic peptide can be promoted, for example, by preparing the natriuretic peptide in a pharmaceutical composition having a pH of about 5 to 9, preferably about 6.5 to 7. The stability of the natriuretic peptide can also be stabilized by providing the natriuretic peptide in a pharmaceutical composition, which further includes, e.g., a stabilizer, such as a polyol. In such embodiments, the pharmaceutical composition can include about 5%, 10%, 20% or more of a polyol (or polyols). An example of a polyol which can be used in the pharmaceutical composition is glycerol. In other aspects, the stability of the natriuretic peptide can be increased by providing the natriuretic peptide in a crystallized, freeze-dried or lyophilized form. If the composition is frozen, the composition should be thawed prior to the time of use. In another embodiment, the invention features a composition which includes a natriuretic peptide, e.g., a natriuretic peptide described herein, and which has a pH of about 5 to 9, preferably about 6.5 to 7. The invention also features a composition which includes a natriuretic peptide, e.g., a natriuretic peptide described herein, and a stabilizing agent, e.g., a polyol, e.g., glycerol. The polyol can be present at about 5%, 10% or 20%.

The dosage of the composition comprising the natriuretic peptide depends upon the particular use of the natriuretic peptide, but the dosage should be an effective amount for the composition to perform its intended use. Data obtained from the cell culture assays and animal studies can be used in formulating a range of dosage for use in humans. Generally, for a composition comprising a natriuretic peptide that is an aqueous solution, it is believed that from about 1 mL to about 50 mL of such composition is sufficient to promote a natriuretic activity as described herein. However, depending on the use of the composition, the dosage can range from about 1 mL to about 200 mL.

The pharmaceutical compositions can be included in a container, pack, or dispenser together with instructions for administration.

Also within the scope of the invention are kits comprising a natriuretic peptide described herein. The kit can include one or more other elements including: instructions for use; other reagents, e.g., other therapeutic agents (e.g., one or more of: an anti-microbial, e.g., an antibiotic, an antiviral, an antifungal, an antiparasitic agent, an anti-inflammatory agent, an antihistamine, an anti-fibrolytic agent and an analgesic); a diluent; devices, e.g., containers, e.g., sterile containers, or other materials for preparing the natriuretic peptide for administration; pharmaceutically acceptable carriers (e.g., a stabilizer); and devices or other materials for administration to a subject (e.g., syringes, applicators, bandages, spray or aerosol devices). The instructions can include instructions for therapeutic application including suggested dosages and/or modes of administration, e.g., in a patient with congestive heart failure. In some applications, the natriuretic peptide can be administered in combination with other components and the kit can include instructions on the amount, dosage, and timing of administration of the natriuretic peptide and the other components.

In some embodiments, the natriuretic peptide may be supplied in lyophilized or freeze dried form. In such embodiments, the kit can include one or more of: instructions for thawing and/or hydrolyzing, and a pharmaceutically acceptable carrier or diluent. In some embodiments, the kit can include instructions for a diluent or a premeasured amount of a diluent.

The present invention also contemplates methods for specifically detecting or quantifying different natriuretic peptides, including the TNPs of the present invention, in a biological sample of interest. These methods generally comprise: (a) separating peptides present in the biological sample as a function of their molecular mass (e.g., by a mass spectroscopic technique such as differential time of flight), wherein each peptide correlates with a detectable signal; (b) detecting the detectable signals during, or at the completion of, the separation; and (c) processing the detectable signals to deduce which, if any, natriuretic peptide is present in the biological sample. In some embodiments, the detectable signals are processed by comparing them to a set of reference detectable signals, each of which correlate(s) with a distinct natriuretic peptide, to thereby determine whether any of the sample detectable signals match the reference detectable signals. Advantageously, these methods permit discrimination and quantification of different natriuretic peptides and can aid in the detection of major metabolites (e.g., enzyme cleaved products) that may result in a NP associated condition (e.g., congestive heart failure).

In order that the invention may be readily understood and put into practical effect, particular preferred embodiments will now be described by way of the following non-limiting examples.

EXAMPLES

Example 1

Isolation, Purification and Identification of Peptides from Snake Venom

Materials And Methods

Venom Collection

Venom was collected from specimens of *Oxyuranus microlepidotus* (Inland taipan) from Goydnor's Lagoon, South Australia, Australia and pooled to minimize the effects of individual variations.

Centrifuge Filtration

Venoms were diluted to 10 mg/mL with buffered saline solution, centrifuged at 1,500×g for two hours in Centricon 50 centrifuge filters (Millipore, 50 kDa cut-off), and then the filtrate centrifuge filtered again at 3,000 G using Centricon 10 tubes (Millipore, 10 kDa cut-off). The filtrates from this step were then lyophilized and stored until needed for LC-MS analysis and RP-HPLC analysis.

LC-MS Analysis of Centrifuge Fractionated Venom

Venom fractions <10 kDa were dissolved in 0.1% TFA to a concentration of 1 mg/mL. On-line LC-MS of venoms was performed on a Vydac C18 analytical column (2.1×35 mm, 5μ particle size, 300 Å) with Solvent A (0.05% TFA, $H_2O$) and Solvent B (90% acetonitrile in 0.045% TFA) at a turbospray flow rate of 130 μL/min. The solvent delivery and gradient formation was achieved using an Applied Biosystems 140 B solvent delivery system. The variable gradient was 0-20% B in the first two minutes and then 20-45% B over the next 12 minutes followed by 45-80% B over the next minute. Electrospray mass spectra were acquired on a PE-SCIEX API III triple quadrupole mass spectrometer that was equipped with an Ionspray atmospheric pressure ionisation source. Samples (10 μL) were injected manually into the LC-MS system and analyzed in positive ion mode. Full scan data was acquired at an orifice potential of 80V over the mass range 400-2100 Da with a step size of 0.2 amu. Data processing was performed with the aid of the software package Biomultiview (PE-SCIEX, Canada).

Preparative RP-HPLC

A Vydac Preparative C18 column (20×250 mm, 10μ, 300 Å) was used on a Waters 600 HPLC system and UV absorbance was monitored at 214 nm by a Waters 486 tuneable absorbance detector. Samples were dissolved in 2 mL of solvent A (0.1% trifluoroacetic acid), manually injected and then the column run at 100% A to wash off the concentrated salts present in the >10 kDa fraction. The following gradient conditions of solvent B (90% acetonitrile, 0.09% trifluoroacetic acid) were then used: 0 to 20% in five minutes, (4% gradient) 20% to 60% over forty minutes (1% gradient) and then 60% to 80% in five minutes (4% gradient).

Edman Degradation Sequencing 0.1 mg of pure peptide was dissolved in 100 μL of 0.1 M ammonium bicarbonate at pH 7.0. 10 μL of 0.1 M TCEP (pH 7) was added and incubated at 50° C. for 20-30 minutes. 30 μL of 0.1M maleimide was then added and incubated at 50° C. for a further 20-30 minutes. Maleimide added 97 amu per cysteine and mass spectroscopy showed an increase of 194 Daltons per disulfide bond. The reduced/alkylated peptides were N-terminally sequenced using Edman degradation chemistry on an Applied Biosystems 477A Protein Sequencer.

Results and Discussion

LC-MS analysis of the fractionated venom revealed the presence of components in the 3-4 kDa range (FIG. 1). Three components, with molecular weights of 3651, 3661 and 4112 Daltons, respectively, were purified by preparative RP-HPLC. Edman degradation sequencing provided the full sequences, revealing a significant degree of homology between the venom components and circulating isoforms of ANP/BNP (FIG. 2). As such these components were designated TNPa, TNPb and TNPc, respectively. The nomenclature chosen reflects the common name source (Taipan), structural homology to natriuretic peptides and chronological order of isolation.

Example 2

Synthesis of Natriuretic Peptides

Synthesis and Oxidation

Analogs of the naturally occurring natriuretic peptides were manually synthesized in accordance with known methods previously described for other disulfide bearing peptides (Nielsen et al., 1999 J. Mol. Biol. 289, 1405-1421). In brief, the peptides, including ANP, BNP, and TNP toxins and analogs (see sequences in Tables 1 and 2) were manually assembled using the stepwise in situ neutralization protocol for Boc chemistry. The amino acid side-chain protection was as follows: Cys (MeBzl), Tyr (BrZ), Asn (Xan), Asp (OcHex), selenocys (MeBzl), Lys (ClZ), Gln (Xan) and Ser (Bzl). All the syntheses were performed on either Boc-EGlu-(OBzl)-$OCH_2$-Pam, Boc-EGlu-(OcHx)-$OCH_2$-Pam or Boc-Ala-$OCH_2$-Pam resins. Deprotection and cleavage were carried out in HF:p-cresol:p-thiocresol (9:0.5:0.5) for 1.5 h. The pure, reduced peptides (0.02-0.05 mM) were oxidized in aqueous 0.1M $NH_4HCO_3$ (pH 8.0, adjusted with 0.1 M $NH_4OH$). The peptide solutions were then stirred for 2-4 days at room temperature to achieve oxidation. Oxidized peptides were purified by preparative RP-HPLC on C18 semi-preparative or preparative HPLC columns. HPLC studies were performed on Waters 600E and Shimadzu LC-2010 instruments. All the preparative HPLC was carried out using a Phenomenex $C_{18}$ column (250×21.20 mm, 10 μm). All of the analytical HPLC were carried out using either a Zorbax 300SB-$C_8$ (150×2.1 mm, 5 μm) column or a Phenomenex $C_{18}$ (250×4.6 mm, 10 μm) with a 90% Acetonitrile and 0.043% Trifluoroacetic acid as the eluting buffer B and 1% B per minute as the gradient. Electrospray mass spectra were acquired on a Micromass LCT (UK) which is a liquid chromatography-orthogonal acceleration reflecting TOF mass spectrometer, coupled to an agilent HPLC system.

Analogs prepared on BocGlu-OcHex-Pam resin using in-situ neutralization Boc chemistry and cleaved from resin using HF:p-cresol:p-thiocresol (9:0.5:0.5) were: TNPc Z0, TNPc A7, TNPc K7, TNPc A7S6, TNPc K7S6, TNPc ChA 10, TNPc R18, TNPc U9, U25, TNPc DTT, TNPc BTT, TNPc Nle, TNPc I-28-P, TNPc ATT, TNPc TBT, TDT, H12A TDT and V20A TDT.

After deprotection and cleavage the analogs were lyophilized and folded in ammonium bicarbonate (400 mL, 0.1M, pH 8.1). The only exception being the U9,U25 analog which was folded directly using ammonium formate (0.1 M, 400 mL pH 4.5, adjusted with formic acid). When the folding reaction was completed the pH of the reaction mixtures were lowered to 2.0 with TFA, filtered and subjected to preparative HPLC using Vydac protein and peptide C18 preparative or semi-preparative columns. The solvents were (A) 0.05% TFA in water and (B) 0.05% TFA in acetonitrile:water 90:10; the gradient used was 0.57% B/minute. Analytical HPLC was performed as described above. Mass spectra were recorded on an Applied Biosystems API2000 LC-MSMS mass spectrometer which was connected to an Agilent LC system in positive ion mode (m/z 400-1800, DP 40 V, FP 400 V, EP 10V, IS 5500V), 0.1 amu steps. Data were deconvoluted to obtain the molecular mass from multiply charged species using the Applied Biosystems Bioanalyst software. The peptides were quantified by RP-HPLC using hBNP as an external standard. The samples were found to be 80-90% peptide. The samples that were dispatched to the Baker Institute and provided for cellular assays were from the same batch and had been lyophilized from dilute acetic acid and then acetonitrile/water to remove traces of TFA from the sample.

Analysis

Peptides were quantified initially by triplicate amino acid analysis and then by RP-HPLC (HP 1100) using an external reference standard for each peptide. Mass spectra were acquired on a PE-Sciex API III triple quadrupole electrospray mass spectrometer (MS) in positive ion mode (m/z 500-2000, at 0.1-0.2-Da steps, declustering potentials of 10-90 V, and dwell times of 0.4-1.0 s). Data were deconvoluted (MacSpec 3.2, Sciex, Canada) to obtain the molecular weight from the multiply charged species. MS was used to confirm purity and to monitor peptide oxidation.

Reduction and Alkylation

Purified peptides (~100 pmol) were fully reduced in the presence of TCEP and 50 mM ammonium acetate at pH 8 (37° C. for 1 h) and then alkylated in the presence of maleimide (37° C., 1 h). The alkylated peptides were purified by RP-HPLC, applied to a Biobrene treated glass fiber filter, and analysed by Edman chemistry using an ABI model 470A protein sequencer. Alkylation of peptides with maleimide allowed their cysteine residues to be observed as PTH-cys-maleimide doublets (diastereomers).

Results and Discussion

Figure 3:
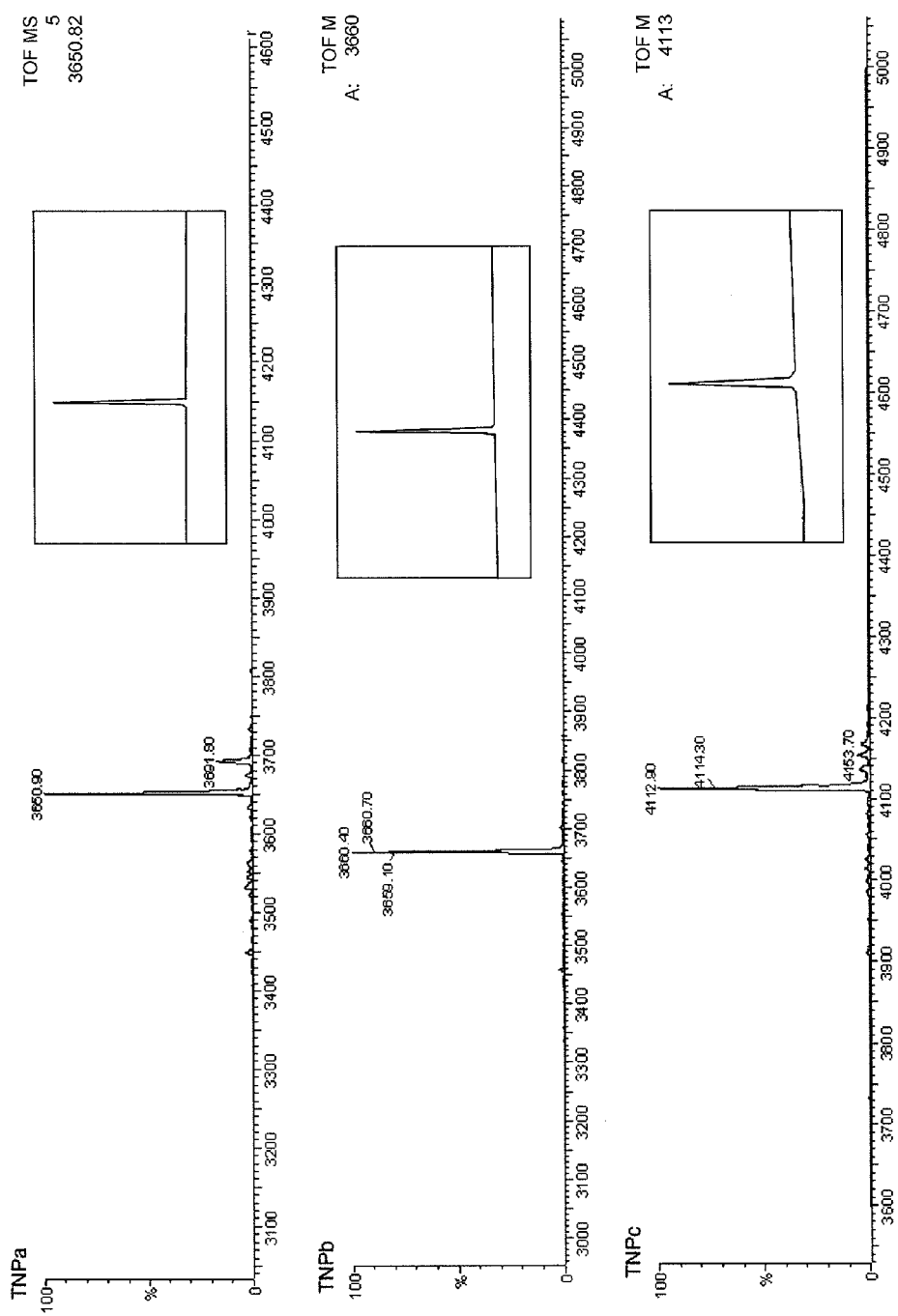
FIG. 3 is a graphical representation showing an ESI-TOF MS and RP-HPLC profile of synthetic TNPa, TNPb and TNPc. Reconstructured Mass in Daltons is given. RP-HPLC was performed on a C18 phenomenex 4.6×250 mm analytical column, with a 1% B/min linear gradient.

Synthetic procedures based on Boc in situ neutralization chemistry for TNP toxins and their analogs has been successfully established. Chain assembly proceeded efficiently with every coupling yield above 99.6% according to the quantitative ninhydrin test. Illustrative examples of the results are provided in FIG. 3.

Examination of the sequences of the peptides showed that despite the strong homology with both ANP and BNP the *O. microlepidotus* venom peptides differ at several key points. The natriuretic peptides can be considered to consist of three distinct regions: the ring structure, the N-terminal head and the C-terminal tail. Within the ring structure, the following observations can be made. TNPa and TNPb have the invariant Arg (i.e., present in the NP signature) at position eight of the loop replaced by an His. Although, this would normally be considered a conservative substitution, Arg→His in TNPc resulted in reduced effects on lowering blood pressure compared to TNPc. This provides support for the notion that the NP signature requires an Arg at this position. Previous examinations within the ring structure of ANP have shed some light on functionality (Watanabe et al., 1988, *Eur. J. Pharmacol.* 147:49-57; Thibault et al., 1995, *Mol. Pharm.* 48: 1046-1053). Replacement of Phe at position 2 within the loop of ANP with the D-amino form of the same amino acid almost completely abolished activity. However, replacement of Gly at position nine within the ring with D-Ala increased the activity. A similar effect to Phe occurred when Asp at position 6 within the ring was replaced with the D-Asp, activity being reduced to only negligible amounts. The presence of Pro in the venom peptides at position five cannot explain any differences in activity as all three *O. microlepidotus* peptides, whether equipotent to ANP or not, contain the residue at this location. These venom peptides are novel in containing prolines at this location.

Strikingly, the C-terminal tails of the TNP molecules shared no homology with this region in ANP or other NPs. The C-terminal tails in TNPs are as long (TNPa and TNPb) or longer than (TNPc) the length previously shown to be the minimum for full activity (Watanabe et al., 1988; Wakitani et al., 1985, *Circ. Res.* 56: 621-627). TNPc has a C-terminal tail, that differs in length and sequence to that of the other TNPs and each of the TNPs contains two prolines within the C-terminal tail. Due to its restrained conformation, prolines are contained within turns in secondary structure. Yet the positions of the prolines differ amongst TNPa/b and TNPb, suggesting that the tails may adopt different conformations. It is notable that the two peptides (TNPa and TNPb) that are inactive in assays specific for ANP/BNP activity have a Pro at a location different than TNPc which is equipotent to ANP. Of interest, substitution of the C-terminal Ile in TNPc by the equivalent Pro in TNPa/b reduces the activity significantly (see Example 8). Considering that all other active NPs have a hydrophobic amino acid (i.e., Val, Ile) in that position, it is reasonable to propose that the NP signature should be considered to extend beyond the loop consensus structure to additionally consider elements of tail structure. The C-terminal region, which is associated with NP stability in vivo, may play a role in protecting the core ring structure via tertiary interactions. The reduced activity of TNPa and TNPb can be explained, at least in part, by the departure (despite its apparent conservative nature) from the consensus NP sequence and the presence of a tail Pro where a hydrophobic residue is found consistently in other NPs. TNPc and its derivatives have superior activity because the NP signature is conserved. Other features present in the TNP family, particularly TNPc, contribute to enhanced stability over ANP (consistent with C-terminal tail theory).

Example 3

Aortic Ring Experiments

Materials And Methods

Male Sprague Dawley rats were killed and the descending thoracic aorta rapidly removed and flushed with physiological solution. After being cleared of adhering fat and connective tissue, 5 mm rings were mounted under 10 g resting tension, between two stainless steel hooks, in organ baths (37° C.) containing carbogenated (95% $O_2$ and 5% $CO_2$) physiological salt solution of the following composition (mM): NaCl, 118.4; $NaHCO_3$, 25; glucose, 11; KCl, 4.7; $MgSO_4$, 1.2; $KH_2PO_4$, 1.2 and $CaCl_2$, 2.5. The lower hook was attached to a tissue holder and the upper hook to a force displacement transducer (Grass FTO3). Where indicated endothelial cells were removed by gentle rubbing of the intimal surface with a wire. To confirm the presence or absence of endothelial cells, tissues were precontracted with a sub-maximal concentration of phenylephrine (0.3 µM) and the response to acetylcholine (ACh, 10 µM) observed. Ach-induced relaxation greater than 80% of maximum indicated the presence of endothelium; whereas Ach-induced relaxation less than 10% indicated the absence of endothelium. Ring preparations under resting tension were conditioned by two contraction/relaxation cycles with 40 mM KCl, contracted by a third application of 40 mM KCl and then relaxed with different doses of the venom peptides. Responses were expressed as a percentage relaxation of the precontraction by KCl.

Results and Discussion

Figure 4:
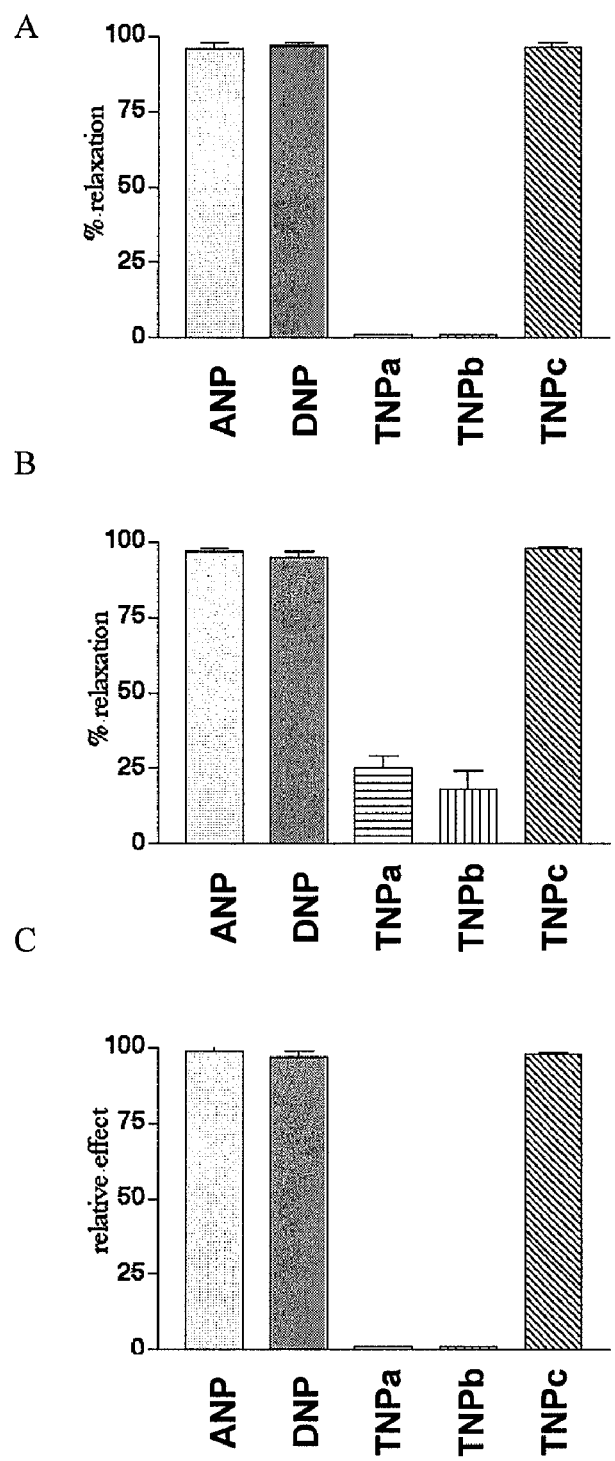
FIG. 4 is a graphical representation showing comparative effects of venom derived natriuretic peptides (0.1 μM) on rat (A) endothelium-intact and (B) endothelium-denuded aortas pre-contracted with 40 mM KCl (N=5). (C) 0.1 μM comparative cGMP production in 293 cells over-expressing GC-A. N=3.

Pharmacological analysis of the peptides showed that the activity profile differs amongst the suite of peptides (FIG. 4) despite the highly conserved sequences. For example, TNPc was equipotent to ANP and DNP in producing a near 100% relaxation in pre-contracted aortae. These effects were consistent between endothelium-intact (NPR-C mediated) and -denuded rings (GC-A mediated). However, TNPa and TNPb produced only minor (approximately 20% maximum) relaxation effects in the endothelium-intact aortic rings and no relaxation in denuded rings.

Figure 5:
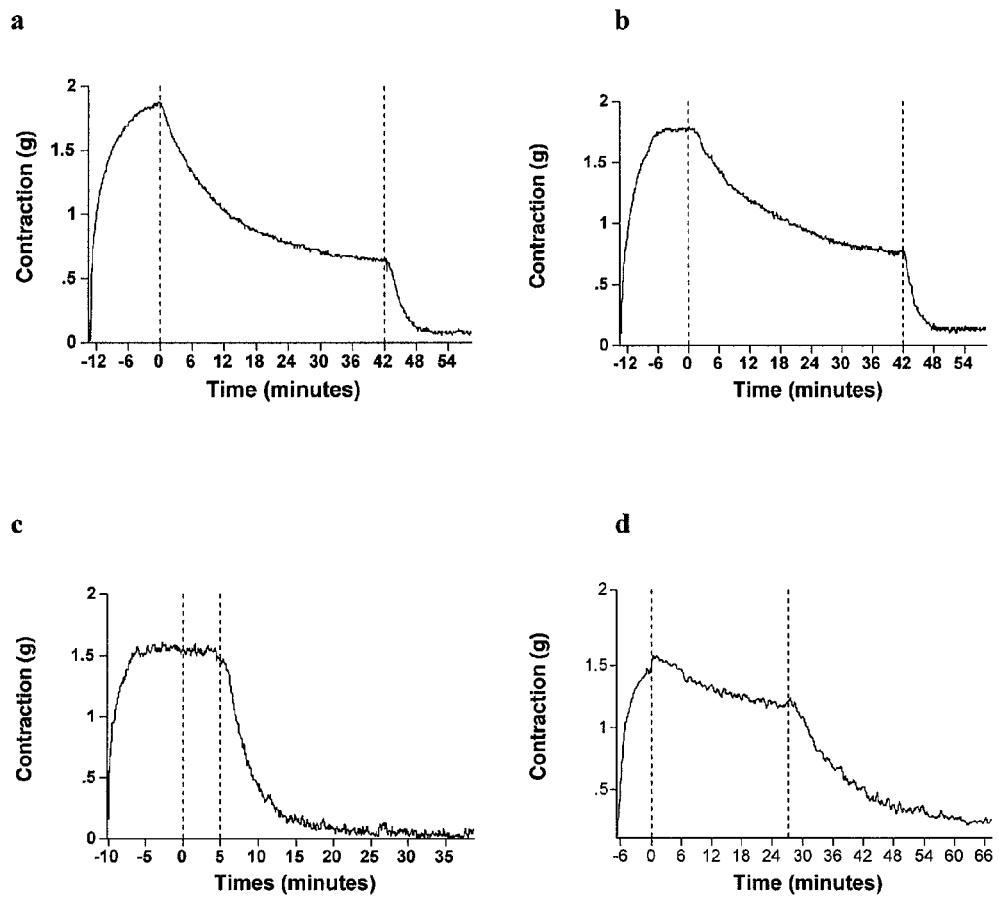
FIG. 5 is a graphical representation showing that TNPa and TNPb lack the ability to competitively inhibit the binding of TNPc to either the endothelium intact or endothelium denuded aortic rings. TNPa (10 nM; t=0) followed by TNPc (0.1 μM; t=42) on (A) endothelium-denuded and (B) endothelium-intact aortas pre-contracted with 40 mM KCl. TNPb (0.1 μM; t=0) followed by TNPc (0.1 μM) on (C) endothelium-denuded (t=5) and (D) endothelium-intact aortas pre-contracted with 40 mM KCl (t=27). N=3. Note that TNPc is able to cause complete inhibition of contraction, while 10-fold higher doses of TNPa and TNPb cause only partial or no inhibition of contraction.

In addition, neither TNPa or TNPb were able to competitively inhibit the binding of TNPc to either the endothelium intact or endothelium denuded aortic rings (FIG. 5, TNPb results shown). Taken together, these results suggest a variation of selectivity amongst the peptides which is dictated by only relatively minor alterations in peptide sequence. The high potency of TNPc provides evidence that this peptide will have an activity profile similar to hANP and BNP.

Example 4

Determination of Cell Cyclic GMP Elevations

Materials And Methods

The human embryonic kidney 293 (HEK-293) cell line was used for the stable expression of rat GC-A (GC-A/293). Cells expressing rat GC-A (GC-A/293) in the HEK-293 cell line were as previously described (Potter L. R., and Garbers D. L., (1992), J Biol Chem. 26, 14531-4) and determination of cGMP elevations was undertaken as previously described (Chrisman et al. T. D., Schulz, S., Potter, L. R. and Garbers, D. L., (1993,) J. Biol. Chem. (1993) 268 (5), 3698-3703). Responses were expressed as a percentage of the effect produced by ANP.

Results and Discussion

The peptides TNPa, TNPb and TNPc were tested on the GC-A receptor overexpressed in HEK-293 cells and cGMP elevations were determined and compared to those of other natriuretic peptides ANP and DNP. These results (FIG. 4C) showed that the O. microlepidotus peptides display a range of activities. For example, TNPc is equipotent to ANP and DNP, whereas TNPa and TNPb displayed lesser effects on cGMP elevations. This result is consistent with those obtained using the aortic ring experiments, suggesting that TNPc is a natriuretic peptide with similar potency to ANP, acting at both the NPR-A and NPR-C receptors.

In summary, in specific tissue and cell-based assays, TNPc is equipotent to DNP and ANP whereas TNPa and TNPb were the first ANP/BNP-like natriuretic peptides to be inactive or only weakly active upon the GC-A cell based assays as well as the endothelium-denuded aortic rings. In addition, these peptides were only weakly active on the NPR-C mediated relaxation in endothelium-intact aortic rings. As demonstrated by their inability to inhibit the binding of TNPc, these peptides do not bind at all, even in an antagonistic manner, to GC-A and have a low affinity for NPR-C. Within the ring structure these peptides have a histidine substituted for the invariant arginine at position eight and contain a proline at ring position five. Uniquely, these peptides contain a proline at residue three of the C-terminal tail, a location previously shown to be crucial for binding. TNPa and TNPb are the first natriuretic peptides with this change in structure of the C-terminal tail and also the first with replacement of a crucial invariant residue within the ring structure. Due to sequential and functional variability, the snake venom natriuretic peptides may represent a distinct group within the natriuretic peptide family, which possesses activity divergent from the rest of the family.

Example 5

Solution Stability of NPs

Methods

Peptides are dissolved at 1 mg/mL in 5 mM sodium acetate buffer/0.9% saline. The samples are stored at 37° C. and aliquots taken at intervals over a 31-day period. For comparison studies, a fresh sample of each peptide is made up from dry lyophilized powder stored at −20° C. at the same concentration in water just prior to evaluation. Samples are evaluated by RP-HPLC/MS using an optimized chromatography program over a mass range of 300-1800 amu.

Example 6

Plasma Stability of Natriuretic Peptides

Materials and Methods

Plasma preparation: Blood samples (from healthy human volunteers) were drawn into a sealed tube containing ethylene diamine tetra-acetic acid (EDTA). After sampling, the plasma was separated by centrifugation at 14,000 rpm for 30 min. Plasma was taken out and stored in separated Eppendorf tubes at −20° C.

Stability assay in human and rat plasma: Human or rat plasma (sample size 200 µL) was incubated at 37° C. for 5 min. 50 µL peptide stock solution (5 mg/mL) was added to the plasma. The vortexed reaction mixture was incubated at 37° C. Sample aliquots of 30 µL were taken from the reaction mixture at sequential intervals of 0 h, 1 h, 2 h, 4 h and 24 h and the sample reaction quenched immediately with 30 µL extraction buffer containing 50% Acetonitrile, 50% 0.1 M NaCl and 1% TFA. The quenched aliquots were cooled in ice for 5 min prior to centrifugation at 14,000 rpm for 15 min. 20 µl of the supernatant from each of the centrifuged aliquots was injected into RP-HPLC for analysis.

Results

These studies were undertaken to evaluate the plasma stability of TNPc at normal body temperature. The results for both rat and human plasma are summarized diagrammatically in FIG. 6A. This shows clearly that TNPc is stable in plasma for at least 24 h at 37° C. (with 72% remaining in human plasma and 76% remaining in rat plasma) The results demonstrate unambiguously that TNPc has a much longer half-life in plasma compared to WT-hANP (55 min in human plasma and 58 min in rat plasma).

Example 7

Stability of Natriuretic Peptides to Enzymatic Degradation

Materials and Methods

The incubation buffer contained 100 mM Tris/HCl and 150 mM NaCl and the pH was adjusted to 7.2-7.4. In each assay, 100 µl of peptide [500 µM] was incubated with 300 µl buffer (with 500 ng Endopeptidase (NEP) or 10 µg Plasmin) at 37° C. 50 µl aliquots were taken at times 5 min, 30 min, 60 min, 90 min, 180 min and 24 h. The reaction was quenched by heating to 100° C. for 4 min and the remaining peptide concentrations measured by RP-HPLC. Note that the levels of Plasmin required to degrade these peptides was several thousands time the levels present in human plasma.

Results

Endopeptidase (EC 3.4.24.11) is an ectoenzyme which is involved with the clearance of NPs in vivo. It inactivates NPs by opening their 17-member ring structure. Plasmin, a serine proteinase, is able to degrade most extracellular proteins. It possesses tryptic-like specificity and hydrolyses protein and peptides at lysyl- and arginyl-bonds. It also has esterolytic activity toward basic amino acid esters and amidolytic activity toward basic amino acid amides. Results from these two assays confirmed the results of the plasma assay: TNPc is more stable than either ANP and BNP, supporting its candidacy as a therapeutic for heart failure (Results are shown in Table 7 and FIGS. 6b-c). The result against NEP is interesting. TNPc did not show any degradation over the 180 min measurement period (by comparison ANP had been completely degraded by that time), while BNP had been significantly degraded. As NEP presents a known degradation pathway for NPs, this result represents a significant advantage for TNPc. It is also evident that the increased NEP stability cannot be explained by the length of the tail region alone as the NEP cleavage site residues at the N-terminal end of the loop region. These results demonstrate that TNPc is more stable than either ANP and BNP, supporting its candidacy as a therapeutic for heart failure.

Example 8

Effect of Natriuretic Peptides on Blood Pressure and Heart Rate in Rabbits

Materials and Methods

Animals

Experiments were conducted using 13 naïve male New Zealand white rabbits, bred from stock and housed at the Baker Heart Research Institute and whose weight ranged from 2.5 to 3.3 kg. Prior to and during experimentation each animal was housed in individual standard rabbit cages, under conditions of constant ambient temperature, constant humidity and normal light/dark cycle (with the lights on from 06:00 to 18:00). Food and water were accessible ad libitum for the duration of the study. All procedures were performed in accordance with the Australian Code of Practice for the Care and Use of Animals for Scientific Purposes (Australian Government Publishing Service, Canberra, Australia, 1990) and were approved by the Animal Experimentation Committee of the Alfred Hospital/Baker Heart Research Institute.

Experimental Procedures

On the day of the experiment, the rabbit was placed in a standard single rabbit holding box (15 cm high and wide and 35 cm long) with wire top and raised wire grid floor. Under local anesthesia (Lignocaine HCl, 1%), the central ear artery and marginal ear vein were catheterized. A one-hour recovery period was allowed before commencing the experiment.

Pulsatile arterial blood pressure was measured with a Statham P231D strain gauge pressure transducer (Statham, Hato Rey, Puerto Rico). Mean arterial pressure (MAP) and heart rate (HR) were digitized and averaged over two-second periods by computer using the LabVIEW programming language (National Instruments, Austin, Tex., USA).

Experimental Design

Each rabbit received up to eight experiments separated by a 1 week recovery. During each experiment, a dose response curve to TNP (a, b, c, c I28P, c R16H, c N7D, c P32R, c Cha-10, c R-18, c A7, c K7, c BTT, c DTT, c A7s6, c K7S6, c Z0, c diseleno and c Nle), DNP, human ANP (WT-hANP), human ANP methionion oxide (hANP m/o) or a control experiment was performed with the drug administered via the marginal ear vein catheter (Table 8). For each experiment there was an initial 60 min acclimatization period and a 45 min period during which baseline cardiovascular parameters were obtained in duplicate. Dose-response curves were performed using 3 increasing doses of the peptides administered using a variable rate infusion pump (Harvard Apparatus, model 22 I/w, South Natick, Mass., USA) at 3, 6, and 12 mL/hr to give doses of 1, 2, and 4 µg/kg/min. These were the same doses as those used for ANP to give a maximum 14% reduction in blood pressure (Woods et al., 1989, *J Cardiovasc* 13 (2): p. 177-185). For the time control experiment, the same volumes of vehicle (0.9% saline) were administered at the same infusion rates. Each dose was infused for 45 min. The order of experiments was randomized and only one dose-response curve was performed in each animal per experiment.

Data Analysis

Two sec averages of all parameters were displayed on the computer and movement artifacts were excluded from the measurements. Data were averaged over 20 mm for each of the control periods, and over the last 15 min of the treatments at each dose. The 3 values for each dose were also averaged to give an "average response" value.

Statistical Analysis

Values were expressed as mean difference from control ±standard error of the difference (SED). The analysis of data was performed by a multi factor split plot (nested) ANOVA which combined a repeated measure within animal design and also allowed for comparisons between groups (treatments as described in Tables 9A and 9B). The total sums of squares (SS) was divided into between-groups and within-groups SS. The latter contained the between treatments SS, between animals SS and animal x treatment interaction for each of the groups (Snedecor G W and Cochran W G. *Statistical Methods*. Ames, Iowa: Iowa State University Press, 1980). Comparisons within each group were made using a set of orthogonal contrasts. The F ratio for each contrast was calculated as the mean square for the contrast (MS) divided by the total residual MS of the groups. Contrasts within groups were made by using a set of comparisons in which the between column SS and the between animal SS were subtracted from the total SS to give the residual SS. The latter were used to calculate the average treatment standard error of the mean (indicating variation within animals). Thus, the estimate of the within group variance was made with a contribution from all the groups.

Compounds Used

The compounds tested are listed in Table 8 and include the Taipan natriuretic peptides TNP—(a, b, c, c I28P, c R16H, c N7D, c P32R, c Cha-10, c R-18, c A7, c K7, cDTT, c BTT, c A7s6, c K7S6, c Z0, c diseleno and c Nle), DNP, human ANP and human ANP methionion oxide. The doses of drugs were expressed in μg of the base and were dissolved in 0.9% saline.

Results and Discussion

Blood Pressure and Heart Rate

In a randomized design, several different natriuretic peptides were examined for cardiovascular effects in separate experiments, over a period of several weeks using conscious rabbits. Over the course of the experimental period, basal values of BP and HR remained constant. During each experiment, 45 min infusions of 1, 2 and 4 μg/kg/min (of ANP or the molar equivalent of the peptide to be tested) were administered intravenously. The results are summarized in Tables 9A and 9B.

The human form of ANP (WT-hANP) markedly lowered MAP ($-15.8\pm0.7$ mmHg, $P<0.001$, Table 9A). It had little overall effect on HR, although there was a modest tachycardia with the first 2 doses. Of the 4 naturally occurring natriuretic-like peptides, only TNPc and DNP reduced MAP, with similar average falls of $-14.9\pm0.7$ mm Hg and $-14.2\pm0.8$ mm Hg, respectively ($P<0.001$, Table 9). There was no difference between these responses and the MAP reduction by WT-hANP. Systolic BP and diastolic BP followed the same trend as MAP. TNPa and TNPb had little or insignificant effects on blood pressure. Only TNPa produced a significant change in HR ($-14\pm4$ bpm, $P<0.05$) and there was a trend for WT-hANP to increase HR but no other effects on HR were noted (Tables 9A and 9B).

Cardiovascular responses to a variant of human ANP, hANP methionine oxide, were compared with those to WT-hANP (Table 6). hANP m/o lowered MAP by an average $-10.6\pm0.9$ mm Hg ($P<0.05$ compared to vehicle) which was less than the response to WT-hANP ($-15.8\pm0.7$ mm Hg, $P<0.01$). Tachycardia of $28\pm7$ bpm ($P<0.01$ compared to vehicle) accompanied the fall in MAP but the variance in HR was also increased, resulting in no difference between the HR effects of the two human forms of ANP. A significant dose response relationship was not observed with administration of any of the taipan natriuretic-like peptides.

Tables 10A and 10B summarize the results of the changes to MAP in response to the highest dose of all the peptides including TNPc analogs. Compared to vehicle, the majority of TNPc analogs produced significant reductions in MAP. Only peptide analogs I28P, R16H, and R-18 (n=5 for each group) did significantly reduce MAP compared to vehicle treatments.

One hour after completion of WT-hANP infusions, there was an increase in MAP of $5.0\pm1.2$ mm Hg ($P<0.05$), an observation consistent with its short half life. In contrast, one hour after the end of TNPc infusion, MAP had not changed, suggesting that TNPc has a greater half life compared to WT-hANP. In support of this view the inventors compared the time taken to recover from a bolus injection of 0.24 mg/kg TNPc and the equivalent molar dose of BNP. In 3 rabbits the time taken to recover to 50% of the peak response for TNPc was 225 minutes and for BNP the time was 80 minutes (n=1). Thus there is a 3-fold longer effective half life with TNPc compared to BNP.

The TNPc analogs of Group 2a (I28P, N7 and P32R) did recover from the hypotension during a further hour after cessation of the infusion (Table 10A). However, there was partial recovery with TNPc N7D (Table 10A).

A longer recovery period was allowed for the peptides studied as part of Group 2b and Group 2c (Table 10B). After TNPc, MAP remained suppressed for 2 hours. TNPc analogs A7, K7, BTT, K7S6 and diseleno TNPc also did not recover after 2 hours whilst MAP of the remaining analogs partially recovered (Cha10, DTT, A7S6, Z0 and Nle TNPc, Table 10B).

In summary, the major findings were that TNPc, when compared to vehicle administration, produced a marked decrease in blood pressure that was similar to the human form of ANP, WT-hANP. TNPc was the most hypotensive taipan natriuretic-like peptide examined whereas the effects of TNPa and TNPb and hANP m/o on blood pressure were similar to those produced by vehicle in conscious normotensive rabbits. TNPc also evoked a prolonged suppression of blood pressure, lasting for at least the 2 hour measurement period. Most TNPc analogs also reduced blood pressure and were long lasting.

Example 9

Effect of Natriuretic Peptides on an Ovine Model of Congestive Heart Failure

The aim of these experiments was to compare the efficacy of TNPc with ANP for the acute treatment of moderate congestive heart failure (CHF). The animal model used was the Ovine model of tachycardia induced CHF.

Materials and Methods

Surgical Procedures

All procedures conform with the *Guide for the Care and Use of Laboratory Animals* published by the US National Institutes of Health (NIH Publication No. 82-23, revised 1996). Six adult crossbred sheep (weight, 50 to 55 kg) were implanted with pacemakers under isoflurane anesthesia and oxygen. A bipolar screw fixation ventricular pacing lead was placed transvenously under fluoroscopic guidance in the apex of the right ventricle. The proximal end of the lead was connected to pacemakers reprogrammed for high-rate pacing (Sigma, Medtronic) that were positioned subcutaneously in the lateral aspect of the neck. Oxytetracycline (5 mL), an antibiotic, and flunixin meglumine (1 mL), an analgesic, were administered subcutaneously prophylactically on the day of surgery. After 3 days of recovery, right ventricular pacing was initiated at 180 bpm and continued for 4 weeks to induce CHF (NYHC III). Animals were anesthetized and an echocardiographic examination and a conductance catheter evaluation were performed.

Experimental Protocol

Details of experimental procedures in 6 sheep are given in Table 11A. Animals were randomized to either TNPc or ANP on two consecutive days, according to the schedule in Table 11B. Studies were conducted over a period of 4 days with two study groups.

On the day of the first experiment, after a control period in which baseline measurements were made, drug infusion via a fore-leg vein using new calibrated Terumo syringe pumps was commenced (TNPc or ANP randomized to days 1 or 2) at 2, 4 and 6 pmol/min/kg, each for 30 min. Echocardiographic and conductance catheter evaluations were performed at 30 min after each drug level. On the second day, the experiment was repeated with the other drug (either TNPc or BNP according to day 1 treatment) at 2, 4 and 6 pmol/min, each for 30 min and echocardiographic and conductance catheter evaluations were performed at 30 min after each drug level. The animal was euthanased at the conclusion of the experiment. Stock solutions of each peptide were made up under sterile conditions using sterile saline, were protected from light with aluminium foil and kept refrigerated.

Data Analysis

Left ventricular (LV) ejection fraction was monitored by echocardiography and the conductance catheter was used to measure LV dP/i, LV end diastolic pressure, LV ESPVR, heart rate and mean arterial pressure (MAP). Values were expressed as mean +/−SEM and were analyzed by Students t-test. A value of p<0.05 was considered significant.

Results and Discussion

ANP at the high dose rate significantly increased LV ejection fraction from baseline and from the low dose (Table 12A). This was not maintained by the end of the of the recovery period (30 min). ANP significantly decreased LV end diastolic pressure at the high dose rate. Once again this was not maintained during the recovery period. A decrease in these parameter values is expected for effective treatment of CHF. Notably, no significant increase in heart rate was observed for ANP, consistent with the notion that NPs do not induce tachycardia. The results from the TNPc infusions were remarkably similar to ANP (Table 12B). Once again there were improvements in the LV ejection fraction and decreases in the LV end diastolic pressure at the high dose rates providing evidence that this peptide is effective in treating CHF. TNPc also reduced −dp/dt by 27%. There were no significant changes in any other parameters associated with either substance. Acute improvements in LV ejection fraction and LV end diastolic pressure in heart failure subjects are a very positive finding for both substances.

Example 10

Effect of Natriuretic Peptides on Cardiovascular Parameters in a Rat Model of Chronic Heart Failure

Materials and Methods

Animals

Experiments were conducted in 10 Sprague-Dawley rats. The rats were bred from stock and housed in the animal facility at the Baker Heart Research Institute. Prior to each experiment, the rats were housed in standard rat cages under conditions of constant ambient temperature, humidity and normal light/dark cycle. All procedures were performed in accordance with the Australian Code of Practice for the Care and Use of Animals for Scientific Purposes (Australian Government Publishing Service, Canberra, Australia, 1990) and were approved by the Animal Experimentation Committee of the Alfred Hospital/Baker Heart Research Institute.

Surgical Procedures

Six rats underwent surgery to occlude the left coronary artery. After anesthetic administration (intraperitoneal injection of 1.5 mL/kg 50% Ketamine 100 mg/mL & 50% Xylazine 20 mg/mL), the left coronary artery was occluded by a suture via open-chest surgery. After surgery, the rats were treated with fluids and with an anti-inflammatory analgesic (Carprofen, 5 mg/kg), an anti-arrhythmia drug (procainamide, 10 mg/kg) and an anti-cholinergic drug (atropine 1 mg/kg) and were monitored for normal mobility, activity and normal eating habits. Six-eight weeks after occlusion, the experiment was conducted.

Experimental Procedures

On the day of the experiment, the rat was anaesthetised with sodium pentobarbital (bolus of 60 mg/kg intraperitoneally, then 0.5 mg/kg/min intravenous infusion after insertion of jugular catheter). A double-lumen catheter was inserted into the jugular vein (for infusion of anaesthetic and peptides) and a catheter was inserted into each of the femoral arteries (for measurement of arterial pressure and for taking blood samples). A Mikro-Tip pressure catheter (model SPR-249 3F, Millar Instruments, Houston, Tex., USA) was passed into the left ventricle via the right carotid artery for recording of left ventricular pressure and the rat was tracheotomized to facilitate spontaneous respiration. A small bore catheter was placed in the bladder for urine collection and held in place with a purse-string suture. Finally, a transit-time ultrasound flow probe (type 2SB, Transonic Systems Inc, Ithaca, N.Y., USA) was placed around the abdominal aorta to measure blood flow.

Experimental Protocol

After the completion of preparations, a 30 min resting period was allowed for cardiovascular parameters to stabilize. The control period followed, during which 0.9% saline was infused at 3 mL/hr for 30 min using a variable rate infusion pump (Harvard Apparatus, model 22 I/w, South Natick, Mass., USA). Urine was collected throughout this period and a blood sample was taken at the end for measurement of hematocrit. Two doses of either TNPc or BNP (50 pmol/kg/min and 100 pmol/kg/min) or vehicle saline were then infused at 3 mL/hr for 30 min each, with urine collected over each period and hematocrit measured at the end. One hour was allowed for recovery of parameters. Each rat received up to 3 drugs, TNPc, BNP or vehicle with order randomized. At the end of the experiment, the animal was euthanased with an overdose of sodium pentobarbital and the heart removed and weighed.

Data Analysis

Two-second averages of all parameters (systolic, diastolic and mean arterial pressure (MAP), heart rate (HR), blood flow and left ventricular pressure (LVP)) were displayed on the computer and movement artifacts were excluded from the measurements. Data was averaged over 30 min for each of the control periods, and over the last 10 min of the treatments at each dose. The two values for each dose were also averaged to give an "average response" value. Urine volume was measured gravimetrically and hematocrit was determined by the capillary tube method. The left ventricle was separated from the remainder of the heart and weighed. It was flattened onto a sheet of grid paper and the size of the infarct estimated by tracing around the tissue.

Statistical Analysis

Values were expressed as mean difference from control ±standard error of the difference (SED). The analysis of data was performed by a multi factor split plot (nested) ANOVA which combined a repeated measure within animal design and also allowed for comparisons between groups (vehicle, BNP and TNPc). The total sums of squares (SS) was divided into between-groups and within-groups SS. The latter contained the between treatments SS, between animals SS and animal x treatment interaction for each of the groups (Snedecor G W and Cochran W G. *Statistical Methods*. Ames, Iowa: Iowa State University Press, 1980. Comparisons within each group were made using a set of orthogonal contrasts.

Results and Discussion

Six anesthetized rats with chronic heart failure were each treated with up to 3 drugs: vehicle (n=4), BNP (n=4) or TNPc (n=6) and 4 normal rats were treated with BNP (n=3) or TNPc (n=1). Data from these experiments are shown in Table 13. Diastolic LVP was higher in the heart failure rats (11±2 mm Hg vs 5±0 mm Hg in normal rats) indicating that those animals had significant infarcts. Diastolic LVP was significantly reduced by both TNPc and BNP in heart failure rats (−1.2±0.5 mm Hg and −1.0±1.0 mm Hg, respectively) compared to vehicle (+1.4±0.9 mm Hg). In heart failure rats, TNPc lowered average MAP by −15.9±4.1 mm Hg which was similar to the response to BNP (−18.1±6.3 mm Hg) but was smaller than the fall in MAP in the normal rat (−23.5 mm Hg). The change in MAP in response to vehicle infusions was minimal (−3.3±1.2 mm Hg). Abdominal aortic blood flow was not altered by either drug in heart failure animals (Table 13). However, in normal rats, blood flow was reduced but only by TNPc (−6.2 mL/min from 18.4 mL/min). TNPc but not BNP enhanced urine production in heart failure rats (+1.4±0.3 mL/hr) but neither peptide altered hematocrit. Direct comparison of the effects of BNP and TNPc in heart failure animals indicated that there were no statistical differences in any parameter supporting the view that both peptides are acting through very similar mechanisms to relieve the hemodynamic consequences of heart failure. At post-mortem, the size of the infarct was found to be an average 22% of the area of the left ventricle.

Example 11

Aortic Ring Experiments on Additional Analogs

Materials and Methods

In addition to the peptides tested in example 3, a series of 13 analogs corresponding to the 2a, 2b and 2c grouping of peptides were examined for their ability to dilate noradrenaline constricted aortic rings. The degree of constriction was expressed as a percentage of the KCl induced constriction. The aortic rings were prepared in a manner similar to the method described in example 3. The peptides tested were ANP, TNPc, TNPc I28P, TNPc P32R, TNPc Cha-10, TNPc R-18, TNPc A7, TNPc K7, TNPc BTT, TNPc DTT, TNPc A7S6, TNPc K7S6, TNPc Z0, TNPc Nle, and TNPc diseleno. In each case there were at least 3 separate aortic rings tested per peptide and all were denuded of endothelium to ensure responses were confined to the GC A receptor.

Results

The vast majority of peptides including TNPc were effective at dilating endothelial denuded aortic rings. The degree of relaxation was closely similar to that produced by ANP which was reduced 66% of the constriction produced by KCl (Table 14). TNPc K7 produced a lesser response compared to ANP (50%) while TNPc R-18 was ineffective. These results confirm the effectiveness of TNPc and the vast majority of peptides but also show that subtle substitutions can alter effectiveness of the TNP like compounds in acting on the GC A receptor. Thus the ability to predict the action of natriuretic peptides cannot be induced intrinsically and must be determined experimentally.

Example 12

Development of an Assay to Measure Response of Cultured Mammalian Cells to Natriuretic Peptide Stimulation Materials and Methods Cell Culture Madin-Darby Canine Kidney (MDCK) cells were maintained in Dulbecco's Modified Eagle Medium (DMEM) (Gibco Invitrogen, Mt Waverley, Australia) supplemented with 5% Foetal Bovine Serum (Cambrex Bio Science, Rockland, USA), 1% Penicillin/Streptomycin (Gibco Invitrogen, Mt Waverley, Australia) and 1% Gluta-MAX (Gibco Invitrogen, Mt Waverley, Australia). Upon reaching confluence, cells were sub-cultured such that they would be 70-90% confluent at time of assay.

cGMP Assay

Cyclic GMP (cGMP) elevation in MDCK cells in response to Natriuretic Peptide stimulation was performed using a cGMP AlphaScreen kit (PerkinElmer, Boston, USA), as follows for normal experiments: Cells were detached, pelleted to remove growth medium, and resuspended in Stimulation Buffer (Hank's Balanced Salt Solution, 0.1% Bovine Serum Albumin [BSA] (Sigma-Aldrich, Castle Hill, Australia), 1 mM 3-Isobutyl-1-methylxanthine [IBMX] (Sigma-Aldrich, Castle Hill, Australia)) and diluted to $6 \times 10^6$ cells per mL (30 000 cells per 5 µL). 5 µL of cells were added to wells of white 384-well OptiPlates (PerkinElmer, Boston, USA), and stimulated with increasing concentrations of peptide for 30 minutes at 37° C. Cells were then lysed with 10 µL Lysis buffer ($dH_2O$, 0.3% Tween-20 (Sigma-Aldrich, Castle Hill, Australia), 5 mM HEPES (JRH Biosciences, Kansas, USA) and 0.1% BSA) and 5 µL acceptor bead mix (10 µL per mL acceptor beads and 1/3000 anti-cGMP antibody (BioVision, Mountain View, USA) in lysis buffer) added per well in the dark. Plates were incubated in the dark at room temperature for 30 minutes, then 5 µL donor bead mix (10 µL per mL donor beads and 0.3 nM biotinylated cGMP in lysis buffer) was added per well in the dark and the plate incubated overnight at room temperature. Signal was read using an EnVision plate reader (PerkinElmer, Boston, USA) and data analysed using Prism software. The cGMP standard curve was performed as per manufacturers instructions. This assay was optimized for cell number, cell passage number and peptide stimulation time to obtain a good signal:noise ratio.

Peptides hBNP was purchased from the American Peptide Company (Sunnyvale, USA) and rANP was purchased from Bachem (Bubendorf, Switzerland). Taipan Natriuretic Peptides and analogues of the naturally occurring Natriuretic Peptides were manually synthesized, deprotected and cleaved from resin in accordance with known methods previously described. In brief, the peptides were manually assembled using stepwise in situ neutralization protocol for Boc chemistry.

Results and Discussion

Assay Development

Figure 7:
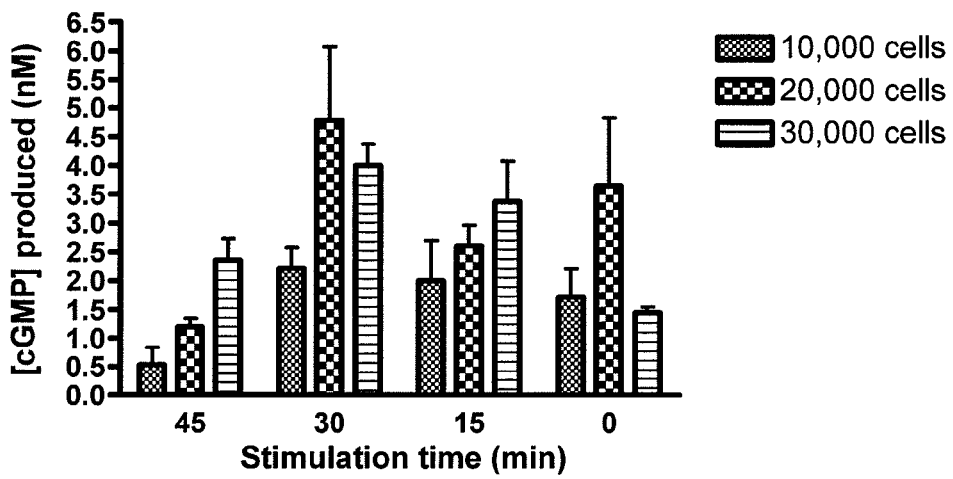
FIG. 7 is a graphical representation showing optimization of cGMP AlphaScreen assay for MDCK cell number and peptide stimulation time. Cells were stimulated for the specified times with 1 nM rat ANP.
Figure 8:
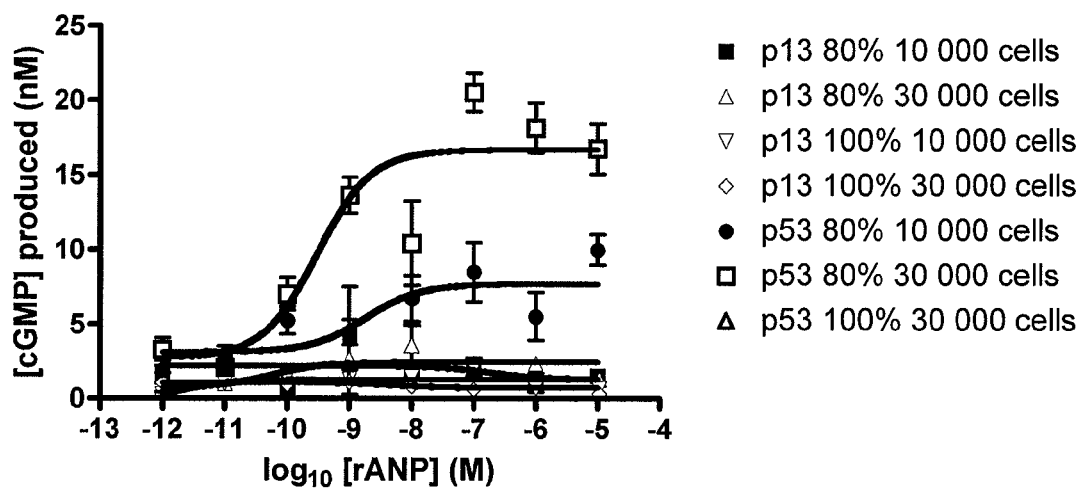
FIG. 8 is a graphical representation showing optimization of cell confluence and passage number. Cells were stimulated with rat ANP (Bachem) for 30 minutes.

MDCK cells are canine kidney epithelial cells isolated from a healthy female animal. They display epithelial characteristics including apical-basolateral polarity. A sensitive assay for measuring cGMP elevation in these cells in response to stimulation with Natriuretic Peptides has been developed and optimized (see FIGS. 7 and 8), using the Perkin Elmer cGMP AlphaScreen kit. cGMP elevations measured in response to Natriuretic Peptide stimulation using this assay represent a Natriuretic Peptide Receptor-A (NPR-A) signaling response. Optimization experiments showed that sub-confluent, late passage cells, stimulated for 30 minutes with Natriuretic Peptide gave the best cGMP response (see FIGS. 1 and 2). After 30 minutes, the response begins to decrease, presumably due to peptide degradation and/or receptor desensitization. Further, it was found that using 30 000 cells per well gave the best signal:noise ratio when late passage cells were used (see FIG. 8).

Example 13

Figure 9A:
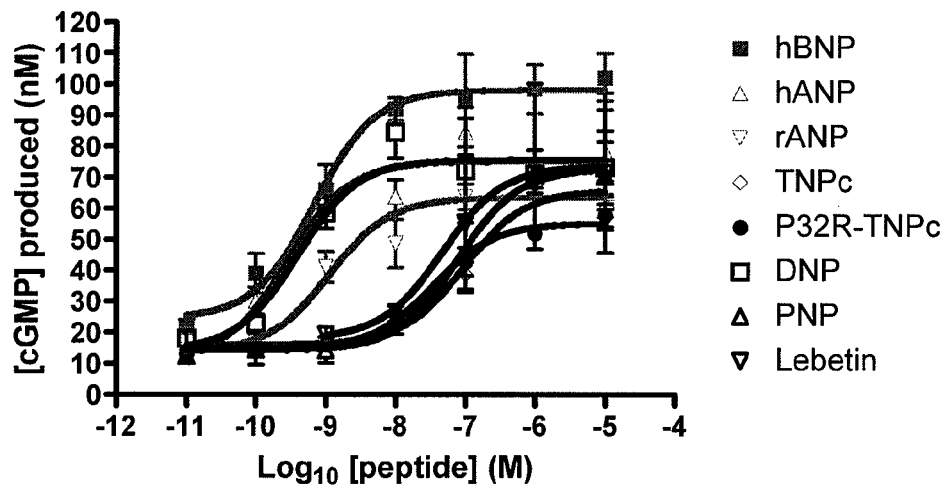
FIG. 9 is a graphical representation depicting representative dose response curves showing cGMP elevation in MDCK cells in response to various Natriuretic Peptides and synthetic analogues (a) (see key). Selected curves are highlighted in the graphs shown in (B) and (C).
Figure 9B:
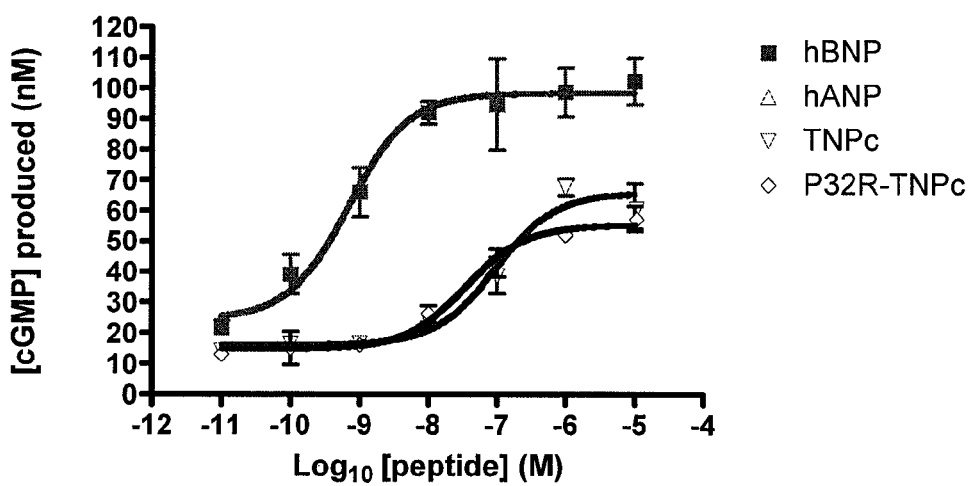
Figure 9C:
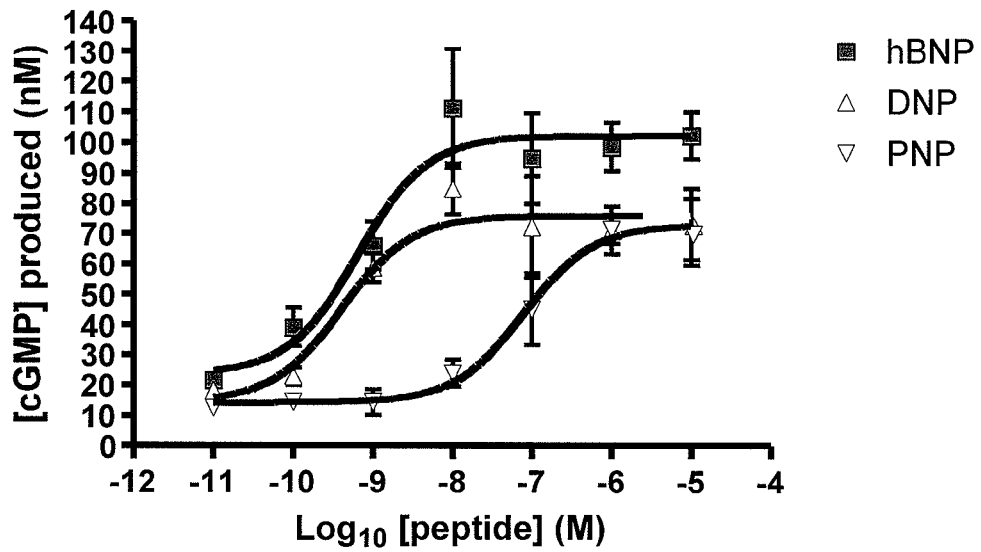

Taipan Natriuretic Peptide C (TNPc) and Synthetic Analogs Thereof Stimulate NPR-A Signaling in MDCK Cells To examine whether TNPc and synthetic analogs produced in the inventors' laboratory could stimulate NPR-A signaling, cGMP elevations in MDCK cells in response to these peptides were measured, as described above. It was found that each of the peptides could stimulate cGMP accumulation in MDCK cells, at varying potencies (see Table 15). Potency is described by the EC50 value, which is the concentration of peptide required to give half of the maximal cGMP response. Representative dose response curves for the different peptides are shown in FIG. 9.

Example 14

Development of an Assay to Measure Response of Cultured Mammalian Cells to Natriuretic Peptide Stimulation Materials and Methods Cell Culture HeLa cells were maintained in RPMI cell culture medium (Gihco Invitrogen, Mt Waverley, Australia) supplemented with 10% Foetal Bovine Serum (Cambrex Bio Science, Rockland, USA). Upon reaching confluence, cells were subcultured such that they would be 70-90% confluent at time of assay.

cGMP Assay

Cyclic GMP (cGMP) elevation in HeLa cells in response to Natriuretic Peptide stimulation was performed using a cGMP AlphaScreen kit (PerkinElmer, Boston, USA), as follows for normal experiments: Cells were detached, pelleted to remove growth medium, and resuspended in Stimulation Buffer (Hank's Balanced Salt Solution, 0.1% Bovine Serum Albumin [BSA] (Sigma-Aldrich, Castle Hill, Australia), 1 mM 3-Isobutyl-1-methylxanthine [IBMX] (Sigma-Aldrich, Castle Hill, Australia)) and diluted to $6 \times 10^6$ cells per mL (30 000 cells per 5 µL). 5 µL of cells were added to wells of white 384-well OptiPlates (PerkinElmer, Boston, USA), and stimulated with increasing concentrations of peptide for 30 minutes at 37° C. Cells were then lysed with 10 µL Lysis buffer ($dH_2O$, 0.3% Tween-20 (Sigma-Aldrich, Castle Hill, Australia), 5 mM HEPES (JRH Biosciences, Kansas, USA) and 0.1% BSA) and 5 µL acceptor bead mix (10 µL per mL acceptor beads and 1/3000 anti-cGMP antibody (BioVision, Mountain View, USA) in lysis buffer) added per well in the dark. Plates were incubated in the dark at room temperature for 30 minutes, then 5 µL donor bead mix (10 µL per ML donor beads and 0.3 nM biotinylated cGMP in lysis buffer) was added per well in the dark and the plate incubated overnight at room temperature. Signal was read using an EnVision plate reader (PerkinElmer, Boston, USA) and data analysed using Prism software. The cGMP standard curve was performed as per manufacturer's instructions. This assay was optimized for cell number, cell passage number and peptide stimulation time to obtain a good signal:noise ratio.

Peptides hBNP was purchased from the American Peptide Company (Sunnyvale, USA) and rANP was purchased from Bachem (Bubendorf, Switzerland). Taipan Natriuretic Peptides and analogues of the naturally occurring Natriuretic Peptides were manually synthesized, deprotected and cleaved from resin in accordance with known methods previously described. In brief, the peptides were manually assembled using stepwise in situ neutralization protocol for Boc chemistry.

Example 15

Figure 10:
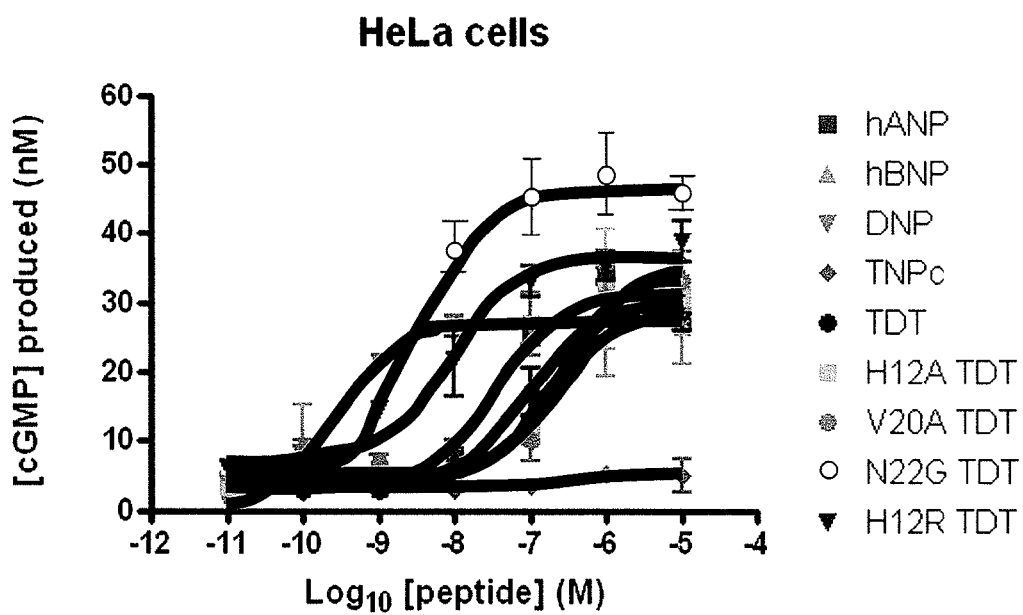
FIG. 10 is a graphical representation showing representative dose response curves showing cGMP elevation in HeLa cells in response to various Natriuretic Peptides and synthetic analogues (a) (see key).

Taipan Natriuretic Peptide C (TNPc) and Synthetic Analogues Thereof Stimulate NPR-A Signaling in HeLa Cells To examine whether TNPc and synthetic analogs produced in the inventors' laboratory could stimulate NPR-A signaling, cGMP elevations in HeLa cells in response to these peptides were measured, as described above. It was found that each of the peptides could stimulate cGMP accumulation in HeLa cells, at varying potencies (Table 16). Potency is described by the EC50 value, which is the concentration of peptide required to give half of the maximal cGMP response. Representative dose response curves for the different peptides are shown in FIG. 10.

Example 16

Stability of TDT to Enzymatic Degradation

Figure 11A:
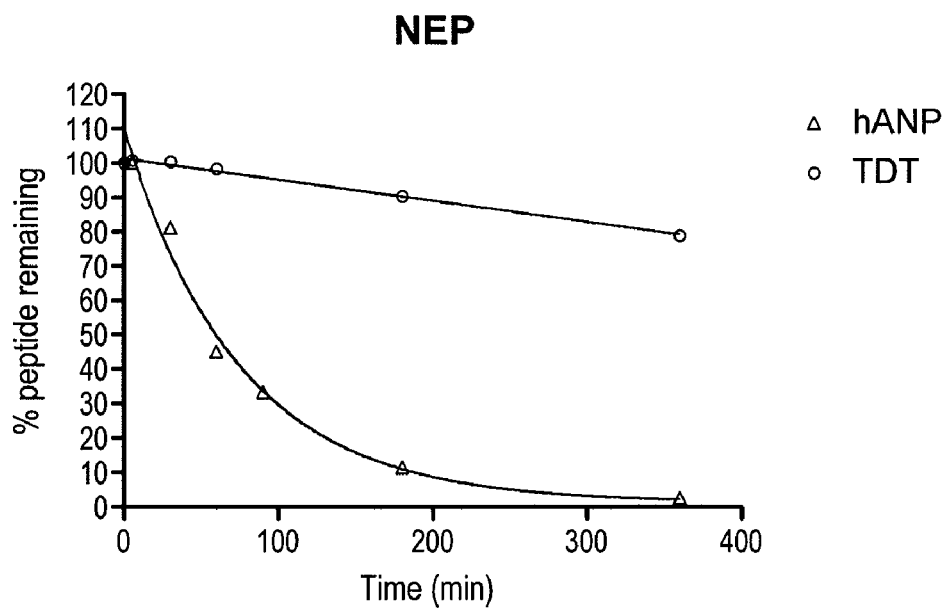
FIG. 11 is a graphical representation showing the comparative stability of TDT and Wt-hANP against (a) NEP, (b) plasmin and (c) pepsin.
Figure 11B:
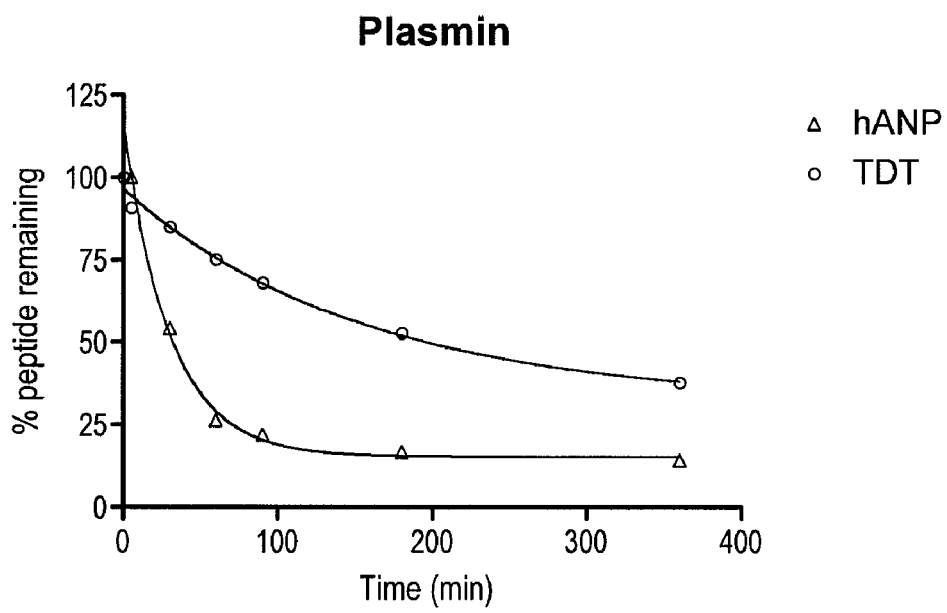
Figure 11C:
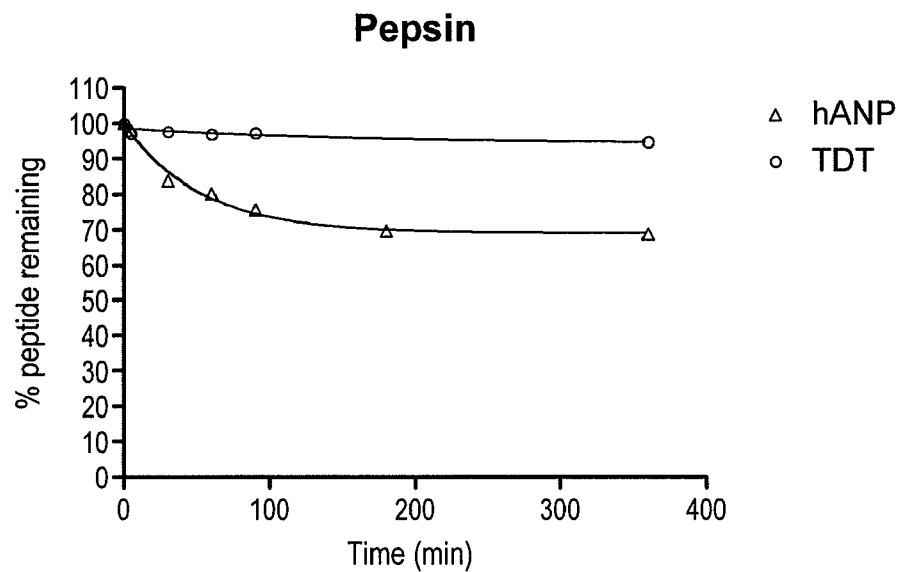

The stability of TDT and was investigated using the same enzymatic degradation assays (NEP, plasmin, pepsin) disclosed in Example 7. Results from all three assays confirmed that TDT is more stable than ANP (see FIGS. 11A-11C). Of interest, TDT showed minimal degradation over the 360 min measurement period (by comparison ANP had been completely degraded by that time). As NEP presents a known degradation pathway for NPs, this result represents a significant advantage for TDT. It is also evident that the increased NEP stability cannot be explained by the length of the tail region alone as the NEP cleavage site residues at the N-terminal end of the loop region. These results demonstrate that TDT is more stable than ANP, supporting its candidacy as a therapeutic for heart failure.

Example 17

Effect of Natriuretic Peptides on Blood Pressure and Heart Rate in Rabbits

Materials and Methods

Animals

Experiments were conducted using 3 naïve male New Zealand white rabbits, bred from stock and housed at the Baker Heart Research Institute and whose weights were 3.2 kg. Prior to and during experimentation each animal was housed in individual standard rabbit cages, under conditions of constant ambient temperature, constant humidity and normal light/dark cycle (with the lights on from 06:00 to 18:00). Food and water were accessible ad libitum for the duration of the study. All procedures were performed in accordance with the Australian Code of Practice for the Care and Use of Animals for Scientific Purposes (Australian Government Publishing Service, Can berra, Australia, 1990) and were approved by the Animal Experimentation Committee of the Alfred Hospital/Baker Heart Research Institute.

Experimental Procedures

The experiments were conducted in conscious normotensive rabbits. On the day of the experiment, the rabbit was placed in a standard single rabbit holding box (15 cm high and wide and 35 cm long) with wire top and raised wire grid floor. Under local anesthesia (Lignocaine HCl, 1%), the central ear artery and marginal ear vein were catheterized. A one-hour recovery period was allowed before commencing the experiment.

Pulsatile arterial blood pressure was measured with a Statham P23ID strain gauge pressure transducer (Statham, Hato Rey, Puerto Rico). Mean arterial pressure (MAP) and heart rate (HR) were digitized and averaged over two-second periods by computer using the LabVIEW programming language (National Instruments, Austin, Tex., USA).

Experimental Design

Each rabbit received two experiments separated by a day's recovery. For each experiment there was an initial 60 min acclimatization period and a 30 min period during which baseline cardiovascular parameters were obtained. A bolus dose of one of the TDT analogs, [N22G]TDT and H12R-TDT, was then given intravenously at a dose of 0.24 mg/kg. Blood pressure and heart rate were recorded for 3-4 hours. Only one drug was administered in each animal per experiment.

Data Analysis

Two sec averages of all parameters were displayed on the computer and movement artifacts were excluded from the measurements. Data were averaged over 30 min for each of the control periods, and over 15 min of the treatment when the MAP had reached a minimum. The values from each rabbit for each analog were averaged to give an "average response" value. Values were expressed as mean difference from control ±standard error of the difference (SED).

Compounds Used

The compounds were [N22G]TDT and H12R-TDT and were dissolved in 0.9% saline.

Results and Discussion

Blood Pressure and Heart Rate

Two different natriuretic peptides were examined for cardiovascular effects in separate experiments, using conscious rabbits. Over the course of the experimental period, basal values of BP and HR remained constant. During each experiment, a bolus dose of 0.24 mg/kg of the peptide to be tested was administered intravenously.

Figure 12:
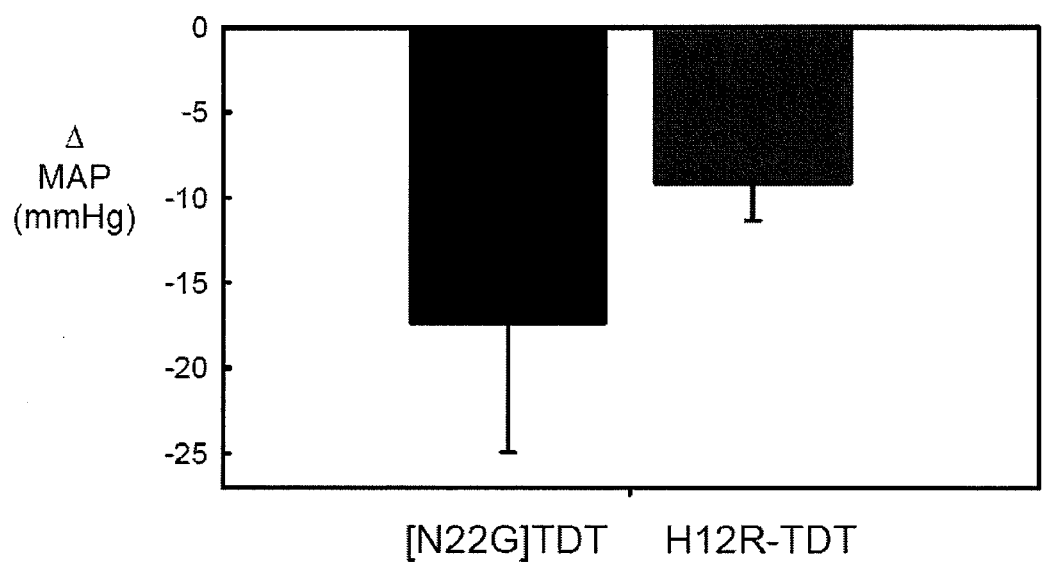
FIG. 12 is a graphical representation showing that analogs [N22G]TDT and H12R-TDT markedly lower MAP in conscious rabbits.

Both analogs [N22G]TDT and H12R-TDT markedly lowered MAP (−17.4±7.6 mmHg and −9.2±2.2 mmHg, respectively, FIG. 12). These effects occurred on average 140 minutes and 97 minutes after administration of [N22G]TDT and H12R-TDT, respectively. [N22G]TDT had little effect on HR whilst H12R-TDT evoked a small bradycardia (−7±5 b/min).

The disclosure of every patent, patent application, and publication cited herein is hereby incorporated herein by reference in its entirety.

The citation of any reference herein should not be construed as an admission that such reference is available as "Prior Art" to the instant application.

Throughout the specification the aim has been to describe the preferred embodiments of the invention without limiting the invention to any one embodiment or specific collection of features. Those of skill in the art will therefore appreciate that, in light of the instant disclosure, various modifications and changes can be made in the particular embodiments exemplified without departing from the scope of the present invention. All such modifications and changes are intended to be included within the scope of the appended claims.

TABLE 1

SEQUENCES OF KNOWN NATRIURETIC PEPTIDES IN HUMAN AND SNAKE

| Natriuretic Peptide | Sequence | SEQ ID |
|---|---|---|
| hANP | SLRRSSCFGGRMDRIGAQSGLGCNSFRY | SEQ ID NO: 82 |
| hBNP | SPKMVQGSGCFGRKMDRISSSSGLGCKVLRRH | SEQ ID NO: 83 |
| hCNP | YKGANKKGLSKGCFGLKLDRIGSMSGLGC | SEQ ID NO: 84 |
| DNP | EVKYDPCFGHKIDRINHVSNLGCPSLRDPRPNAPSTSA | SEQ ID NO: 85 |
| Lebetin 2 isoform α | GDNKPPKKGPPNGCFGHKIDRIGSHSGLGCNKVDDNKG | SEQ ID NO: 86 |
| PNP | GENEPPKKKAPDGCFGHKIDRIGSHSGLGCNKFKPGH | SEQ ID NO: 87 |
| NP consensus | CFGXXXDRIXXXSXLGC | SEQ ID NO: 88 |

TABLE 2

SEQUENCES OF NOVEL TNPs AND THEIR SYNTHETIC ANALOGUES.

| NAME | SEQUENCE | SEQUENCE ID |
|---|---|---|
| TNPa | SDSKIGDGCFGLPLDHIGSVSGLGCNRPVQNRPKK | SEQ ID NO: 89 |
| TNPb | SDPKIGDGCFGLPLDHIGSVSGLGCNRPVQNRPKK | SEQ ID NO: 90 |
| TNPc | SDSKIGNGCFGFPLDRIGSVSGLGCNRIMQNPPKKFSGE | SEQ ID NO: 91 |
| R32-TNPc | SDSKIGNGCFGFPLDRIGSVSGLGCNRIMQNRPKKFSGE | SEQ ID NO: 92 |
| H16-TNPc | SDSKIGNGCFGFPLDHIGSVSGLGCNRIMQNPPKKFSGE | SEQ ID NO: 93 |
| P28-TNPc | SDSKIGNGCFGFPLDRIGSVSGLGCNRPMQNPPKKFSGE | SEQ ID NO: 94 |
| V29-TNPc | SDSKIGNGCFGFPLDRIGSVSGLGCNRIVQNPPKKFSGE | SEQ ID NO: 95 |
| R29-TNPc | SDSKIGNGCFGFPLDRIGSVSGLGCNRIRQNPPKKFSGE | SEQ ID NO: 96 |
| K26-TNPc | SDSKIGNGCFGFPLDRIGSVSGLGCKRTMQNRPKKFSGE | SEQ ID NO: 97 |
| U9, U25-TNPc | SDSKIGNGUFGFPLDRIGSVSGLGUNRIMQNPPKKFSGE | SEQ ID NO: 98 |
| U25-TNPc | SDSKIGNGCFGFPLDRIGSVSGLGUNRIMQNPPKKFSGE | SEQ ID NO: 99 |
| U9-TNPc | SDSKIGNGUFGFPLDRIGSVSGLGCNRIMQNPPKKFSGE | SEQ ID NO: 100 |
| Q7-TNPc | SDSKIGQGCFGFPLDRIGSVSGLGCNRIMQNPPKKFSGE | SEQ ID NO: 101 |
| A7-TNPc | SDSKIGAGCFGFPLDRIGSVSGLGCNRIMQNPPKKFSGE | SEQ ID NO: 102 |
| K7-TNPc | SDSKIGKGCFGFPLDRIGSVSGLGCNRIMQNPPKKFSGE | SEQ ID NO: 103 |
| S6, K7-TNPc | SDSKISKGCFGFPLDRIGSVSGLGCNRIMQNPPKKFSGE | SEQ ID NO: 104 |
| S7-TNPc | SDSKIGSGCFGFPLDRIGSVSGLGCNRIMQNPPKKFSGE | SEQ ID NO: 105 |
| R6, S7-TNPc | SDSKIRSGCFGFPLDRIGSVSGLGCNRIMQNPPKKFSGE | SEQ ID NO: 106 |
| Nle29-TNPc | SDSKIGNGCFGFPLDRIGSVSGLGCNRInQNPPKKFSGE | SEQ ID NO: 107 |
| A31-TNPc | SDSKIGNGCFGFPLDRIGSVSGLGCNRIMQAPPKKFSGE | SEQ ID NO: 108 |
| Q31-TNPc | SDSKIGNGCFGFPLDRIGSVSGLGCNRIMQQPPKKFSGE | SEQ ID NO: 109 |
| A31, O32-TNPc | SDSKIGNGCFGFPLDRIGSVSGLGCNRIMQAOPKKFSGE | SEQ ID NO: 110 |
| Q31, O32-TNPc | SDSKIGNGCFGFPLDRIGSVSGLGCNRIMQQOPKKFSGE | SEQ ID NO: 111 |
| Z0-TNPc | ZSDSKIGNGCFGFPLDRIGSVSGLGCNRIMQNPPKKFSGE | SEQ ID NO: 112 |
| A7, U9, U25, Nle29, A31-TNPc | SDSKIGAGUFGFPLDRIGSVSGLGTINRInQAPPKKFSGE | SEQ ID NO: 113 |
| Z0, A7, U9, U25, Nle29, A31-TNPc | ZSDSKIGAGUFGFPLDRIGSVSGLGUNRInQAPPKKFSGE | SEQ ID NO: 114 |
| BBT | SPKMVQGSGCFGRKMDRISSSSGLGCNRIMQNPPKKFSGE | SEQ ID NO: 115 |
| BTB | SPKMVQGSGCFGFPLDRIGSVSGLGCKVLRRH | SEQ ID NO: 116 |
| TBB | SDSKIGNGCFGRKMDRISSSSGLGCKVLRRH | SEQ ID NO: 117 |
| BTT | SPKMVQGSGCFGFPLDRIGSVSGLGCNRIMQNPPKKFSGE | SEQ ID NO: 118 |
| TBT | SDSKIGNGCFGRKMDRISSSSGLGCNRIMQNPPKKFSGE | SEQ ID NO: 119 |
| TTB | SDSKIGNGCFGFPLDRIGSVSGLGCKVLRRH | SEQ ID NO: 120 |
| AAT | SLRRSSCFGGRMDRIGAQSGLGCNRIMQNPPKKFSGE | SEQ ID NO: 121 |
| ATA | SLRRSSCFGFPLDRIGSVSGLGCNSFRY | SEQ ID NO: 122 |
| TAA | SDSKIGNGCFGGRMDRIGAQSGLGCNSFRY | SEQ ID NO: 123 |
| ATT | SLRRSSCFGFPLDRIGSVSGLGCNRIMQNPPKKFSGE | SEQ ID NO: 124 |
| TAT | SDSKIGNGCFGGRMDRIGAQSGLGCNRIMQNPPKKFSGE | SEQ ID NO: 125 |

TABLE 2-continued

SEQUENCES OF NOVEL TNPs AND THEIR SYNTHETIC ANALOGUES.

| NAME | SEQUENCE | SEQUENCE ID |
| --- | --- | --- |
| TTA | SDSKIGNGCFGFPLDRIGSVSGLGCNSFRY | SEQ ID NO: 126 |
| DDT | EVKYDPCFGHKTDRINHVSNLGCNRIMQNPPKKFSGE | SEQ ID NO: 127 |
| DTD | EVKYDPCFGFPLDRIGSVSGLGCPSLRDPRPNAPSTSA | SEQ ID NO: 128 |
| TDD | SDSKIGNGCFGHKTDRINHVSNLGCPSLRDPRPNAPSTSA | SEQ ID NO: 129 |
| DTT | EVKYDPCFGFPLDRIGSVSGLGCNRIMQNPPKKFSGE | SEQ ID NO: 130 |
| TDT | SDSKIGNGCFGHKIDRINHVSNLGCNRIMQNPPKKFSGE | SEQ ID NO: 131 |
| TTD | EVKYDPCFGFPLDRIGSVSGLGCPSLRDPRPNAPSTSA | SEQ ID NO: 132 |
| TLT | SDSKIGNGCFGHKIDRIGSHSGLGCNRIMQNPPKKFSGE | SEQ ID NO: 133 |
| DLT | EVKYDPCFGHKIDRIGSHSGLGCNRIMQNPPKKFSGE | SEQ ID NO: 134 |
| Z1-TNPc | ZDSKIGNGCFGFPLDRIGSVSGLGCNRIMQNPPKKFSGE | SEQ ID NO: 135 |
| A4-TNPc | SDSAIGNGCFGFPLDRIGSVSGLGCNRIMQNPPKKFSGE | SEQ ID NO: 136 |
| A5-TNPc | SDSKAGNGCFGFPLDRIGSVSGLGCNRIMQNPPKKFSGE | SEQ ID NO: 137 |
| A10-TNPc | SDSKIGNGCAGFPLDRIGSVSGLGCNRIMQNPPKKFSGE | SEQ ID NO: 138 |
| A12-TNPc | SDSKIGNGCFGAPLDRIGSVSGLGCNRIMQNPPKKFSGE | SEQ ID NO: 139 |
| A14-TNPc | SDSKIGNGCFGFPADRIGSVSGLGCNRIMQNPPKKFSGE | SEQ ID NO: 140 |
| A15-TNPc | SDSKIGNGCFGFPLARTGSVSGLGCNRIMQNPPKKFSGE | SEQ ID NO: 141 |
| A16-TNPc | SDSKIGNGCFGFPLDATGSVSGLGCNRIMQNPPKKFSGE | SEQ ID NO: 142 |
| A17-TNPc | SDSKIGNGCFGFPLDPAGSVSGLGCNRIMQNPPKKFSGE | SEQ ID NO: 143 |
| A20-TNPc | SDSKIGNGCFGFPLDRIGSASGLGCNRIMQNPPKKFSGE | SEQ ID NO: 144 |
| A23-TNPc | SDSKIGNGCFGFPLDRIGSVSGAGCNRIMQNPPKKFSGE | SEQ ID NO: 145 |
| A26-TNPc | SDSKIGNGCFGFPLDRIGSVSGLGCARIMQNPPKKFSGE | SEQ ID NO: 146 |
| A27-TNPc | SDSKIGNGCFGFPLDRIGSVSGLGCNAIMQNPPKKFSGE | SEQ ID NO: 147 |
| A28-TNPc | SDSKIGNGCFGFPLDRIGSVSGLGCNRAMQNPPKKFSGE | SEQ ID NO: 148 |
| A29-TNPc | SDSKIGNGCFGFPLDRIGSVSGLGCNRIAQNPPKKFSGE | SEQ ID NO: 149 |
| A30-TNPc | SDSKIGNGCFGFPLDRIGSVSGLGCNRIMANPPKKFSGE | SEQ ID NO: 150 |
| A31-TNPc | SDSKIGNGCFGFPLDRIGSVSGLGCNRIMQAPPKKFSGE | SEQ ID NO: 151 |
| A34-TNPc | SDSKIGNGCFGFPLDRIGSVSGLGCNRIMQNPPAKFSGE | SEQ ID NO: 152 |
| A35-TNPc | SDSKIGNGCFGFPLDRIGSVSGLGCNRIMQNPPKAFSGE | SEQ ID NO: 153 |
| A36-TNPc | SDSKIGNGCFGFPLDRIGSVSGLGCNRIMQNPPKKASGE | SEQ ID NO: 154 |
| A39-TNPc | SDSKIGNGCFGFPLDRIGSVSGLGCNRIMQNPPKKFSGA | SEQ ID NO: 155 |
| Q4-TNPc | SDSQTGNGCFGFPLDRIGSVSGLGCNRIMQNPPKKFSGE | SEQ ID NO: 156 |
| Q16-TNPc | SDSKIGNGCFGFPLDQTGSVSGLGCNRIMQNPPKKFSGE | SEQ ID NO: 157 |
| Q27-TNPc | SDSKIGNGCFGFPLDRIGSVSGLGCNQIMQNPPKKFSGE | SEQ ID NO: 158 |
| Q34-TNPc | SDSKIGNGCFGFPLDRIGSVSGLGCNRIMQNPPQKFSGE | SEQ ID NO: 159 |
| Q35-TNPc | SDSKIGNGCFGFPLDRIGSVSGLGCNRIMQNPPKQFSGE | SEQ ID NO: 160 |
| P31, R32-TNPc | SDSKIGNGCFGFPLDRIGSVSGLGCNRIMQPRPKKFSGE | SEQ ID NO: 161 |
| E4-TNPc | SDSETGNGCFGFPLDRIGSVSGLGCNRIMQNPPKKFSGE | SEQ ID NO: 162 |
| E16-TNPc | SDSKIGNGCFGFPLDETGSVSGLGCNRIMQNPPKKFSGE | SEQ ID NO: 163 |

TABLE 2-continued

SEQUENCES OF NOVEL TNPs AND THEIR SYNTHETIC ANALOGUES.

| NAME | SEQUENCE | SEQUENCE ID |
|---|---|---|
| E27-TNPc | SDSKIGNGCFGFPLDRIGSVSGLGCNEIMQNPPKKFSGE | SEQ ID NO: 164 |
| E34-TNPc | SDSKIGNGCFGFPLDRIGSVSGLGCNRIMQNPPEKFSGE | SEQ ID NO: 165 |
| E35-TNPc | SDSKIGNGCFGFPLDRIGSVSGLGCNRIMQNPPKEFSGE | SEQ ID NO: 166 |
| K26, V27, L28, R29, R30, H31-TNPc | SDSKIGNGCFGFPLDRIGSVSGLGCKVLRRHPPKKFSGE | SEQ ID NO: 167 |
| Y10-TNPc | SDSKIGNGCFGYPLDRIGSVSGLGCNRIMQNPPKKFSGE | SEQ ID NO: 168 |
| TNPc-NH2 | SDSKIGNGCFGFPLDRIGSVSGLGCNRIMQNPPKKFSGENH2 | SEQ ID NO: 169 |
| Z1-TNPc-NH2 | ZDSKIGNGCFGFPLDRIGSVSGLGCNRIMQNPPKKFSGENH2 | SEQ ID NO: 170 |
| L5-TNPc | SDSKLGNGCFGFPLDRIGSVSGLGCNRIMQNPPKKFSGE | SEQ ID NO: 171 |
| L10-TNPc | SDSKIGNGCLGFPLDRIGSVSGLGCNRIMQNPPKKFSGE | SEQ ID NO: 172 |
| L12-TNPc | SDSKIGNGCFGLPLDRIGSVSGLGCNRIMQNPPKKFSGE | SEQ ID NO: 173 |
| L20-TNPc | SDSKIGNGCFGFPLDRIGSLSGLGCNRIMQNPPKKFSGE | SEQ ID NO: 174 |
| L27-TNPc | SDSKIGNGCFGFPLDRIGSVSGLGCNLIMQNPPKKFSGE | SEQ ID NO: 175 |
| L28-TNPc | SDSKIGNGCFGFPLDRIGSVSGLGCNRLMQNPPKKFSGE | SEQ ID NO: 176 |
| L29-TNPc | SDSKIGNGCFGFPLDRIGSVSGLGCNRILQNPPKKFSGE | SEQ ID NO: 177 |
| L30-TNPc | SDSKIGNGCFGFPLDRIGSVSGLGCNRIMLNPPKKFSGE | SEQ ID NO: 178 |
| L36-TNPc | SDSKIGNGCFGFPLDRIGSVSGLGCNRIMQNPPKKLSGE | SEQ ID NO: 179 |
| L17-TNPc | SDSKIGNGCFGFPLDRLGSVSGLGCNRIMQNPPKKFSGE | SEQ ID NO: 180 |
| R12-TNPc | SDSKIGNGCFGRPLDRIGSVSGLGCNRIMQNPPKKFSGE | SEQ ID NO: 181 |
| K13-TNPc | SDSKIGNGCFGFKLDRIGSVSGLGCNRIMQNPPKKFSGE | SEQ ID NO: 182 |
| R13-TNPc | SDSKIGNGCFGFRLDRIGSVSGLGCNRIMQNPPKKFSGE | SEQ ID NO: 183 |
| R18-TNPc | SDSKIGNGCFGFPLDRIRSVSGLGCNRIMQNPPKKFSGE | SEQ ID NO: 184 |
| A7, R18, U9, U25, Nle29-TNPc | SDSKIGAGUFGFPLDRIRSVSGLGUNRInQNPPKKFSGE | SEQ ID NO: 185 |
| A7, R18, U9, U25, Nle29, A31-TNPc | SDSKIGAGUFGFPLDRIRSVSGLGUNRInQAPPKKFSGE | SEQ ID NO: 186 |
| CHA10-TNPc | SDSKIGNGCChaGFPLDRIGSVSGLGCNRIMQNPPKKFSGE | SEQ ID NO: 187 |
| S6, A7-TNPc | SDSKISAGCFGFPLDRIGSVSGLGCNRIMQNPPKKFSGE | SEQ ID NO: 188 |
| H12A TDT | SDSKIGNGCFGAKTDRINHVSNLGCNRIMQNPPKKFSGE | SEQ ID NO: 193 |
| V20A TDT | SDSKIGNGCFGHKIDRINHASNLGCNRIMQNPPKKFSGE | SEQ ID NO: 194 |
| N22G TDT | SDSKIGNGCFGHKIDRINHVSGLGCNRIMQNPPKKFSGE | SEQ ID NO: 195 |
| H12R TDT | SDSKIGNGCFGRKTDRINHVSNLGCNRIMQNPPKKFSGE | SEQ ID NO: 196 |

U = Selenocysteine; O = hydroxyproline, Z = pyroglutamate

TABLE 3

AMINO ACID SUB-CLASSIFICATION

| Sub-classes | Amino acids |
|---|---|
| Acidic | Aspartic acid, Glutamic acid |
| Basic | Noncyclic: Arginine, Lysine; Cyclic: Histidine |
| Charged | Aspartic acid, Glutamic acid, Arginine, Lysine, Histidine |
| Small | Glycine, Serine, Alanine, Threonine, Proline |
| Polar/neutral | Asparagine, Histidine, Glutamine, Cysteine, Serine, Threonine |
| Polar/large | Asparagine, Glutamine |

TABLE 3-continued

AMINO ACID SUB-CLASSIFICATION

| Sub-classes | Amino acids |
|---|---|
| Hydrophobic | Tyrosine, Valine, Isoleucine, Leucine, Methionine, Phenylalanine, Tryptophan |
| Aromatic | Tryptophan, Tyrosine, Phenylalanine |
| Residues that influence chain orientation | Glycine and Proline |

TABLE 4

ABBREVIATIONS FOR AMINO ACIDS

| Amino Acid | 1-Letter Symbol | 3-Letter Symbol |
|---|---|---|
| Alanine | A | Ala |
| Arginine | R | Arg |
| Asparagine | N | Asn |
| Aspartic acid | D | Asp |
| Cysteine | C | Cys |
| Glutamine | Q | Gln |
| Glutamic acid | E | Glu |
| Glycine | G | Gly |
| Histidine | H | His |
| Isoleucine | I | Ile |
| Pyroglutamate | Z | Pyr |
| Leucine | L | Leu |
| Lysine | K | Lys |
| Methionine | M | Met |
| Phenylalanine | F | Phe |
| Proline | P | Pro |
| Serine | S | Ser |
| Threonine | T | Thr |
| Tryptophan | W | Trp |
| Tyrosine | Y | Tyr |
| Valine | V | Val |
| Norleucine | n | Nle |

TABLE 5

EXEMPLARY AND PREFERRED AMINO ACID SUBSTITUTIONS

| Original Residue | Exemplary Substitutions | Preferred Substitutions |
|---|---|---|
| Ala | Val, Leu, Ile | Val |
| Arg | Lys, Gln, Asn | Lys |
| Asn | Gln, His, Lys, Arg, Asp | Gln |
| Asp | Glu, Asn | Glu |
| Cys | Ser | Ser |
| Gln | Asn, His, Lys, | Asn |
| Glu | Asp, Lys, Gla | Asp |
| Gly | Pro | Pro |
| His | Asn, Gln, Lys, Arg | Arg |
| Ile | Leu, Val, Met, Ala, Phe, Norleu | Leu |
| Leu | Norleu, Ile, Val, Met, Ala, Phe | Ile |
| Lys | Arg, Gln, Asn, Orn | Arg |
| Met | Leu, Ile, Phe, Nle | Leu |
| Phe | Leu, Val, Ile, Ala | Leu |
| Pro | Gly, Hyp, Ser, Thr | Gly |
| Ser | Thr | Thr |
| Thr | Ser | Ser |
| Trp | Tyr | Tyr |
| Tyr | Trp, Phe, Thr, Ser | Phe |
| Val | Ile, Leu, Met, Phe, Ala, Nle | Leu |

TABLE 6

Non-Conventional Amino Acids

| | |
|---|---|
| α-aminobutyric acid | L-N-methylalanine |
| α-amino-α-methylbutyrate | L-N-methylarginine |
| aminocyclopropane-carboxylate | L-N-methylasparagine |
| aminoisobutyric acid | L-N-methylaspartic acid |
| aminonorbornyl-carboxylate | L-N-methylcysteine |
| cyclohexylalanine | L-N-methylglutamine |
| cyclopentylalanine | L-N-methylglutamic acid |
| L-N-methylisoleucine | L-N-methylhistidine |
| D-alanine | L-N-methylleucine |
| D-arginine | L-N-methyllysine |
| D-aspartic acid | L-N-methylmethionine |
| D-cysteine | L-N-methylnorleucine |
| D-glutamate | L-N-methylnorvaline |
| D-glutamic acid | L-N-methylornithine |
| D-histidine | L-N-methylphenylalanine |
| D-isoleucine | L-N-methylproline |
| D-leucine | L-N-medlylserine |
| D-lysine | L-N-methylthreonine |
| D-methionine | L-N-methyltryptophan |
| D-ornithine | L-N-methyltyrosine |
| D-phenylalanine | L-N-methylvaline |
| D-proline | L-N-methylethylglycine |
| D-serine | L-N-methyl-t-butylglycine |
| D-threonine | L-norleucine |
| D-tryptophan | L-norvaline |
| D-tyrosine | α-methyl-aminoisobutyrate |
| D-valine | α-methyl-γ-aminobutyrate |
| D-α-methylalanine | α-methylcyclohexylalanine |
| D-α-methylarginine | α-methylcylcopentylalanine |
| D-α-methylasparagine | α-methyl-α-napthylalanine |
| D-α-methylaspartate | α-methylpenicillamine |
| D-α-methylcysteine | N-(4-aminobutyl)glycine |
| D-α-methylglutamine | N-(2-aminoethyl)glycine |
| D-α-methylhistidine | N-(3-aminopropyl)glycine |
| D-α-methylisoleucine | N-amino-α-methylbutyrate |
| D-α-methylleucine | α-napthylalanine |
| D-α-methyllysine | N-benzylglycine |
| D-α-methylmethionine | N-(2-carbamylediyl)glycine |
| D-α-methylornithiine | N-(carbamylmethyl)glycine |
| D-α-methylphenylalanine | N-(2-carboxyethyl)glycine |
| D-α-methylproline | N-(carboxymethyl)glycine |
| D-α-methylserine | N-cyclobutylglycine |
| D-α-methylthreonine | N-cycloheptylglycine |
| D-α-methyltryptophan | N-cyclohexylglycine |
| D-α-methyltyrosine | N-cyclodecylglycine |
| L-α-methylleucine | L-α-methyllysine |
| L-α-methylmethionine | L-α-methylnorleucine |
| L-α-methylnorvatine | L-α-methylornithine |
| L-α-methylphenylalanine | L-α-methylproline |
| L-α-methylserine | L-α-methylthreonine |
| L-α-methyltryptophan | L-α-methyltyrosine |
| L-α-methylvaline | L-N-methylhomophenylalanine |
| N-(N-(2,2-diphenylethyl carbamylmethyl)glycine | N-(N-(3,3-diphenylpropyl carbamylmethyl)glycine |
| 1-carboxy-1-(2,2-diphenyl-ethyl amino)cyclopropane | |

TABLE 7

PEPTIDE HALF LIFE IN PLASMIN
One phase exponential decay; best fit values

| | TNPc | DNP | BNP | ANP |
|---|---|---|---|---|
| SPAN | 0.8454 | 0.7306 | 0.9926 | 0.9579 |
| K | 0.02935 | 0.02381 | 0.053 | 0.3413 |
| PLATEAU | 0.1128 | 0.1675 | 0.03403 | 0.04207 |
| HalfLife (min) | 23.61 | 29.11 | 13.08 | 2.031 |

TABLE 8

PEPTIDES TESTED AND THEIR GROUPINGS

| Group 1 TNP variants | Group 2a TNPc variants | Group 2b TNPc variants | Group 2c TNPc variants | Group 3 Human ANP |
|---|---|---|---|---|
| vehicle | vehicle | vehicle | vehicle | vehicle |
| WT-hANP | TNPc | TNPc | TNPc | WT-hANP |
| TNPa | TNPc 128P | TNPc Cha-10 | TNPc A7S6 | hANP m/o |
| TNPb | TNPc R16H | TNPc R-18 | TNPc K7S6 | |
| TNPc | TNPc N7D | TNPc A7 | TNPc Zo | |
| DNP | TNPc P32R | TNPc K7 | TNPc Nle | |
| | | TNPc BTT | *TNPc diSec | |
| | | TNPc DTT | | |

Group 1: TNP peptides are compared with human ANP
Group 2: TNPc variants are compared with TNPc
Group 3: Human ANP variants are compared with human ANP
*TNPc diSec denotes U9,U25-TNPc or diseleno TNPc

TABLE 9A

EFFECT OF INTRAVENOUS VEH, WT-HANP, TNPA, TNPB, TNPC AND DNP IN CONSCIOUS RABBITS

| | n | Dose (μg/kg/min) 1.0 | 2.0 | 4.0 | SED | Linear Trend | Non Linear | Average Response SED | Significance Veh vs treatment | Significance WT-hANP vs treatment |
|---|---|---|---|---|---|---|---|---|---|---|
| Veh | 10 | | | | | | | | | |
| Systolic BP (mmHg) | | −3.0 | −5.9 | −7.5 | 1.6 | * | NS | −5.5 ± 0.9 | | |
| Diastolic BP (mmHg) | | −5.8 | −6.7 | −5.4 | 1.1 | NS | NS | −5.9 ± 0.6 | | |
| Mean BP (mmHg) | | −5.9 | −7.3 | −6.8 | 1.1 | NS | NS | −6.7 ± 0.7 | | |
| HR (bpm) | | −2.8 | 3.6 | 12.9 | 7.3 | NS | NS | 4.6 ± 4.2 | | |
| WT-hANP | 8 | | | | | | | | | |
| Systolic BP (mmHg) | | −10.6 | −13.0 | −14.5 | 1.6 | NS | NS | −12.7 ± 0.9 | *** | |
| Diastolic BP (mmHg) | | −9.7 | −12.3 | −14.4 | 1.4 | * | NS | −12.1 ± 0.8 | *** | |
| Mean BP (mmHg) | | −13.1 | −15.7 | −18.5 | 1.3 | ** | NS | −15.8 ± 0.7 | *** | |
| HR (bpm) | | 17.1 | 19.0 | 9.0 | 5.5 | NS | NS | 15.1 ± 3.2 | NS | |
| TNPa | 5 | | | | | | | | | |
| Systolic BP (mmHg) | | −2.8 | −4.9 | −9.4 | 2.3 | * | NS | −5.7 ± 1.3 | NS | *** |
| Diastolic BP (mmHg) | | −6.0 | −7.7 | −9.9 | 1.6 | NS | NS | −7.9 ± 0.9 | NS | * |
| Mean BP (mmHg) | | −6.4 | −8.0 | −11.6 | 1.8 | NS | NS | −8.7 ± 1.1 | NS | *** |
| HR (bpm) | | −16.1 | −15.9 | −9.8 | 6.6 | NS | NS | −13.9 ± 3.8 | * | *** |
| TNPb | 5 | | | | | | | | | |
| Systolic BP (mmHg) | | −7.9 | −8.8 | −10.0 | 2.4 | NS | NS | −8.9 ± 1.4 | NS | NS |
| Diastolic BP (mmHg) | | −7.0 | −7.9 | −8.6 | 1.6 | NS | NS | −7.8 ± 0.9 | NS | * |
| Mean BP (mmHg) | | −8.0 | −9.8 | −11.0 | 1.8 | NS | NS | −9.6 ± 1.1 | NS | *** |
| HR (bpm) | | −3.9 | −5.1 | 4.7 | 6.0 | NS | NS | −1.4 ± 3.5 | NS | NS |
| TNPc | 5 | | | | | | | | | |
| Systolic BP (mmHg) | | −9.1 | −15.6 | −14.9 | 1.3 | NS | NS | −13.2 ± 0.8 | *** | NS |
| Diastolic BP (mmHg) | | −10.0 | −14.7 | −12.8 | 1.1 | NS | NS | −12.5 ± 0.6 | *** | NS |
| Mean BP (mmHg) | | −11.0 | −17.7 | −15.9 | 1.2 | NS | NS | −14.9 ± 0.7 | *** | NS |
| HR (bpm) | | −3.5 | 3.7 | 13.8 | 6.6 | NS | NS | 4.7 ± 3.8 | NS | NS |
| DNP | 5 | | | | | | | | | |
| Systolic BP (mmHg) | | −11.7 | −11.9 | −16.4 | 1.4 | NS | NS | −13.3 ± 0.8 | *** | NS |
| Diastolic BP (mmHg) | | −8.5 | −6.9 | −11.7 | 1.6 | NS | NS | −9.0 ± 0.9 | NS | NS |
| Mean BP (mmHg) | | −13.0 | −12.6 | −17.2 | 1.4 | NS | NS | −14.2 ± 0.8 | *** | NS |
| HR (bpm) | | 17.5 | 25.9 | 8.5 | 11.1 | NS | NS | 17.3 ± 6.4 | NS | NS |

Values are mean difference from control and SED indicating group variance
Significance:
* $P < 0.05$,
** $P < 0.01$,
*** $P < 0.001$,
NS $P > 0.05$

TABLE 9B

VEHICLE VS WT-HANP AND HANP M/O IN CONSCIOUS RABBITS

|  |  | Dose (mg/kg/min) | | | | Linear | Non | Average | Significance | |
|---|---|---|---|---|---|---|---|---|---|---|
|  |  |  |  |  |  |  |  |  | Vehicle vs | WT-hANP vs |
|  | n | 1 | 2 | 4 | SED | Trend | Linear | Response SED | treatment | hANP m/o |
| Vehicle | 10 | | | | | | | | | |
| Systolic BP (mmHg) |  | −3.0 | −5.9 | −7.5 | 1.6 | NS | NS | −5.5 ± 0.9 | | |
| Diastolic BP (mmHg) |  | −5.8 | −6.7 | −5.4 | 1.1 | NS | NS | −5.9 ± 0.6 | | |
| Mean BP (mmHg) |  | −5.9 | −7.3 | −6.8 | 1.1 | NS | NS | −6.7 ± 0.7 | | |
| HR (bpm) |  | −3 | 4 | 13 | 7 | NS | NS | 5 ± 4 | | |
| WT-hANP | 8 | | | | | | | | | |
| Systolic BP (mmHg) |  | −10.6 | −13.0 | −14.5 | 1.6 | NS | NS | −12.7 ± 0.9 | *** | |
| Diastolic BP (mmHg) |  | −9.7 | −12.3 | −14.4 | 1.4 | * | NS | −12.1 ± 0.8 | *** | |
| Mean BP (mmHg) |  | −13.1 | −15.7 | −18.5 | 1.3 | * | NS | −15.8 ± 0.7 | *** | |
| HR (bpm) |  | 17 | 19 | 9 | 5 | NS | NS | 15 ± 3 | NS | |
| hANP m/o | 8 | | | | | | | | | |
| Systolic BP (mmHg) |  | −3.1 | −11.8 | −10.5 | 1.5 | ** | * | −8.5 ± 0.8 | NS | * |
| Diastolic BP (mmHg) |  | −7.6 | −10.0 | −8.1 | 1.7 | NS | NS | −8.6 ± 1.0 | NS | NS |
| Mean BP (mmHg) |  | −8.2 | −12.3 | −11.2 | 1.5 | NS | NS | −10.6 ± 0.9 | * | ** |
| HR (bpm) |  | 7 | 27 | 48 | 11 | * | NS | 27 ± 7 | * | NS |

Values are mean difference and SED indicating group variance

Significance:

* P < 0.05,

** P < 0.01,

*** P < 0.001,

NS P > 0.05

TABLE 10A

CHANGE OF MEAN BLOOD PRESSURE DURING THE INFUSION OF GROUP 1, 2A AND 3 PEPTIDES (HIGHEST DOSE) AND ALSO AFTER 1 HOUR RECOVERY PERIOD IN CONSCIOUS RABBITS

| Treatment | n | Treatment Effect | Significance | MAP at Final dose | Recovery | Recovery Delta SED | Significance |
|---|---|---|---|---|---|---|---|
| Group 1 & 3 | | | | | | | |
| Veh | 10 | −6.8 |  | 67.9 | 67.7 | −0.1 ± 0.8 |  |
| WT-hANP | 8 | −18.5 | *** | 54.2 | 59.2 | 5.0 ± 1.2 | * |
| hANP-m/o | 5 | −11.2 | NS | 60.6 | 62.4 | 1.8 ± 2.4 | NS |
| DNP | 5 | −17.2 | ** | 58.9 | 61.4 | 2.5 ± 1.1 | NS |
| TNPa | 5 | −11.6 | NS | 62.3 | 65.3 | 3.0 ± 2.9 | NS |
| TNPb | 5 | −11.0 | NS | 64.7 | 68.2 | 3.5 ± 2.3 | NS |
| TNPc | 5 | −15.9 | ** | 56.1 | 56.6 | 0.5 ± 2.5 | NS |
| Group 2A | | | | | | | |
| Vehicle | 10 | −6.8 |  | 67.9 | 67.7 | −0.1 ± 0.8 |  |
| TNPc | 6 | −14.5 | * | 58.9 | 58.8 | −0.1 ± 2.2 | NS |
| TNPc I28P | 5 | −9.1 | NS | 65.4 | 66.6 | 1.2 ± 2.4 | NS |
| TNPc R16H | 5 | −7.3 | NS | 65.6 | 67.6 | 2.0 ± 3.9 | NS |
| TNPc N7D | 5 | −19.8 | *** | 57.5 | 67.5 | 10.0 ± 5.3 | * |
| TNPc P32R | 5 | −19.9 | *** | 57.5 | 57.6 | 0.1 ± 1.4 | NS |

Values are mean and SEM indicating group variance

Significance:

* P < 0.05,

** P < 0.01,

*** P < 0.001,

NS P > 0.05 compared to vehicle

TABLE 10B

CHANGE OF MEAN BLOOD PRESSURE DURING THE INFUSION OF GROUP 2B AND 2C PEPTIDES AND ALSO AFTER A 2 HOUR RECOVERY PERIOD IN CONSCIOUS RABBITS

| Treatment | n | Treatment Effect | Significance | MAP at final dose | Recovery | Recovery Delta SED | Significance |
|---|---|---|---|---|---|---|---|
| GROUP 2B | | | | | | | |
| Vehicle | 10 | −2.9 | | 70.3 | 68.2 | −2.2 ± 1.1 | |
| TNPc | 6 | −14.5 | *** | 58.9 | 58.8 | −0.1 ± 2.2 | NS |
| TNPc cha-10 | 6 | −10.8 | * | 67.3 | 76.5 | 9.1 ± 3.9 | * |
| TNPc R-18 | 5 | −9.0 | NS | 63.5 | 67.4 | 3.8 ± 1.6 | NS |
| TNPc A7 | 5 | −11.2 | * | 64.0 | 71.3 | 7.3 ± 2.9 | NS |
| TNPc K7 | 5 | −14.1 | ** | 59.0 | 62.4 | 3.4 ± 1.9 | NS |
| TNPc BTT | 5 | −10.8 | * | 63.4 | 65.4 | 2.1 ± 1.5 | NS |
| TNPc DTT | 5 | −12.4 | ** | 58.6 | 70.3 | 11.7 ± 5.2 | ** |
| GROUP 2C | | | | | | | |
| Vehicle | 10 | −2.9 | | 70.3 | 68.2 | −2.2 ± 1.1 | |
| TNPc | 4 | −12.2 | ** | 61.3 | 66.1 | 4.8 ± 4.1 | NS |
| TNPc A7S6 | 3 | −12.9 | * | 56.3 | 66.8 | 10.5 ± 3.1 | ** |
| TNPc K7S6 | 3 | −12.6 | * | 60.3 | 64.2 | 3.9 ± 2.6 | NS |
| TNPc Z0 | 3 | −11.0 | * | 63.3 | 72.2 | 9.0 ± 1.0 | ** |
| diselenoTNPc | 3 | −12.6 | * | 61.0 | 65.8 | 4.8 ± 0.3 | NS |
| Nle TNPc | 2 | −13.6 | ** | 53.4 | 64.5 | 11.0 ± 3.0 | ** |

Values are mean and mean difference from Control ± SED.
Significance:
(*) borderline $P < 0.1$,
* $P < 0.05$,
** $P < 0.01$,
*** $P < 0.001$,
NS $P > 0.05$ compared to vehicle.
Contrasts are Bonferroni adjusted P values

TABLE 11A

DRUG CONCENTRATIONS AND INFUSION LEVELS

| Animal ID | Drug Conc ng/mL | Low ng/min | Low Total | Low Inf ml/min | Hi ng/min | Hi Total | Hi Inf ml/min |
|---|---|---|---|---|---|---|---|
| 100 | 2000 | 945 | 28350 | 0.47 | 4536 | 136080 | 2.27 |
| 226 | | 1120 | 33600 | 0.56 | 5376 | 161280 | 2.69 |
| 81 | | 910 | 27300 | 0.46 | 4368 | 131040 | 2.18 |
| 229 | | 910 | 27300 | 0.46 | 4368 | 131040 | 2.18 |
| 236 | | 1207.5 | 36225 | 0.60 | 5796 | 173880 | 2.90 |
| 207 | | 910 | 27300 | 0.46 | 4368 | 131040 | 2.18 |

TABLE 11B

DOSAGE SCHEDULE

| Animal ID | Weight kg | Day 1 | Day 2 | Start Date |
|---|---|---|---|---|
| 100 | 54 | ANP | TNP | 19 May 2005 |
| 226 | 64 | TNP | ANP | 19 May 2005 |
| 81 | 52 | ANP | TNP | 19 May 2005 |
| 229 | 52 | TNP | ANP | 23 May 2005 |
| 236 | 69 | ANP | TNP | 23 May 2005 |
| 207 | 52 | TNP | ANP | 23 May 2005 |

TABLE 12A

EFFECTS OF ANP ON HEMODYNAMIC PARAMETERS IN CHF-INDUCED SHEEP

| | ejection fraction | EDP | +dP/dt | −dP/dt | ESPR slope | heart rate |
|---|---|---|---|---|---|---|
| baseline | 37.38 ± 2.60 | 7.67 ± 2.06 | 1292.50 ± 191.39 | 1535.33 ± 160.82 | 2.97 ± 0.69 | 98.83 ± 8.39 |
| low | 42.17 ± 2.57 | 5.83 ± 2.82 | 949.33 ± 45.10 | 1336.50 ± 189.70 | 2.85 ± 0.44 | 91.00 ± 8.49 |
| high | 54.50 ± 3.94*#§ | 3.33 ± 3.08*# | 1047.00 ± 39.92 | 1332.17 ± 164.33 | 3.04 ± 0.42 | 96.33 ± 7.77 |
| recovery | 41.00 ± 2.99 | 6.33 ± 3.20 | 1035.83 ± 58.66 | 1232.17 ± 176.54 | 3.44 ± 0.59 | 91.00 ± 4.09 |

*$p < 0.05$ vs baseline;
$p < 0.05$ vs low;
§$p < 0.05$ vs recovery

TABLE 12B

EFFECTS OF TNPC ON HEMODYNAMIC PARAMETERS IN CHF-INDUCED SHEEP

| | ejection fraction | EDP | +dP/dt | −dP/dt | ESPR slope | heart rate |
|---|---|---|---|---|---|---|
| baseline | 41.00 ± 3.16 | 8.50 ± 1.65 | 1271.83 ± 203.40 | 1774.67 ± 168.58 | 2.53 ± 0.24 | 103.83 ± 7.27 |
| low | 48.17 ± 4.66 | 5.83 ± 1.51 | 1079.67 ± 182.62 | 1469.50 ± 252.11* | 2.72 ± 0.56 | 98.00 ± 9.71 |
| high | 61.83 ± 6.01*#§ | 4.17 ± 1.30#§ | 1078.00 ± 132.83 | 1298.00 ± 145.72* | 3.78 ± 0.73 | 100.67 ± 5.90 |
| recovery | 42.33 ± 4.79 | 7.67 ± 0.33 | 1064.83 ± 51.53 | 1201.50 ± 200.38* | 3.35 ± 0.63 | 98.00 ± 3.58 |

*$p < 0.05$ vs baseline;
$p < 0.05$ vs low;
§$p < 0.05$ vs recovery

TABLE 13

EFFECTS OF TNPc AND BNP ON HEMODYNAMIC PARAMETERS IN RAT MODEL OF CHRONIC HEART FAILURE

| | | Dose (pmol/kg/min) | | | | Average drug | Significance | | |
|---|---|---|---|---|---|---|---|---|---|
| | | | | | | | Veh (HF) vs Peptide | Normal vs HF | TNPc vs BNP |
| | n | 50 | 100 | Recovery | SED | response SED | (HF) | (TNPc or BNP) | (N or HF) |
| Veh (HF) | 4 | | | | | | | | |
| Mean BP (mmHg) | | −1.0 | −5.6 | −7.0 | 2.1 | −3.3 ± 1.2 | | | |
| HR (bpm) | | 5.1 | −6.1 | −14.1 | 5.8 | −0.5 ± 3.4 | | | |
| Diastolic LVP (mmHg) | | 1.2 | 1.6 | 1.7 | 1.6 | 1.4 ± 0.9 | | | |
| Blood Flow (ml/min) | | −1.0 | −1.2 | −1.1 | 1.3 | −1.1 ± 0.7 | | | |
| Conductance (ml/min/mmHg) | | −0.4 | −0.2 | −0.1 | 0.6 | −0.3 ± 0.3 | | | |
| HCT (%) | | 1.5 | 0.8 | 2.6 | 2.5 | 1.2 ± 1.4 | | | |
| Urine Flow (ml/hr) | | −0.1 | −0.1 | 0.0 | 0.5 | −0.1 ± 0.3 | | | |
| BNP (HF) | 4 | | | | | | | | |
| Mean BP (mmHg) | | −9.6 | −26.5 | −14.6 | 11.0 | −18.1 ± 6.3 | * | NS | |
| HR (bpm) | | −12.3 | −40.5 | −41.7 | 39.8 | −26.4 ± 23.0 | (*) | NS | |
| Diastolic LVP (mmHg) | | −0.7 | −1.2 | 1.9 | 1.7 | −1.0 ± 1.0 | * | NS | |
| Blood Flow (ml/min) | | −1.6 | −2.9 | −1.0 | 0.8 | −2.2 ± 0.4 | NS | NS | |
| Conductance (ml/min/mmHg) | | −0.3 | 0.2 | 0.5 | 0.5 | −0.1 ± 0.3 | NS | * | |
| HCT (%) | | 1.9 | 0.3 | −1.3 | 1.4 | 1.1 ± 0.8 | NS | NS | |
| Urine Flow (ml/hr) | | 0.8 | 0.7 | −0.2 | 0.5 | 0.7 ± 0.3 | NS | NS | |
| TNPc (HF) | 6 | | | | | | | | |
| Mean BP (mmHg) | | −11.8 | −20.1 | −13.6 | 7.1 | −15.9 ± 4.1 | * | NS | NS |
| HR (bpm) | | −5.2 | −14.8 | −16.5 | 12.0 | −10.0 ± 6.9 | NS | NS | NS |
| Diastolic LVP (mmHg) | | −0.9 | −1.6 | −1.4 | 0.8 | −1.2 ± 0.5 | ** | NS | NS |
| Blood Flow (ml/min) | | −1.6 | −2.9 | −0.5 | 0.8 | −2.2 ± 0.5 | NS | ** | NS |
| Conductance (ml/min/mmHg) | | −0.2 | −0.4 | 0.6 | 0.5 | −0.3 ± 0.3 | NS | NS | NS |
| HCT (%) | | 1.5 | 2.4 | 0.8 | 0.9 | 1.9 ± 0.5 | NS | * | NS |
| Urine Flow (ml/hr) | | 1.0 | 1.7 | 0.9 | 0.5 | 1.4 ± 0.3 | ** | NS | NS |
| BNP (Normal) | 3 | | | | | | | | |
| Mean BP (mmHg) | | −6.4 | −14.9 | −14.1 | 8.1 | −10.7 ± 4.7 | | | |
| HR (BPM) | | −16.6 | −5.3 | 1.3 | 12.4 | −10.9 ± 7.1 | | | |
| Diastolic LVP (mmHg) | | −0.1 | 0.1 | −0.2 | 0.5 | 0.0 ± 0.3 | | | |
| Blood Flow (ml/min) | | −1.9 | −2.6 | −3.6 | 1.7 | −2.2 ± 1.0 | | | |
| Conductance (ml/min/mmHg) | | −1.1 | −1.2 | −1.3 | 0.7 | −1.1 ± 0.4 | | | |
| HCT (%) | | 1.0 | 3.5 | −0.3 | 1.0 | 2.2 ± 0.6 | | | |
| Urine Flow (ml/hr) | | 0.2 | 0.7 | 0.6 | 0.6 | 0.5 ± 0.4 | | | |
| TNPc (Normal) | 1 | | | | | | | | |
| Mean BP (mmHg) | | −21.0 | −25.9 | −4.1 | | −23.5 | | | NS |
| HR (BPM) | | −13.5 | −23.6 | −17.9 | | −18.6 | | | NS |
| Diastolic LVP (mmHg) | | −1.4 | −0.9 | −0.6 | | −1.1 | | | NS |
| Blood Flow (ml/min) | | −5.2 | −7.3 | −3.0 | | −6.2 | | | ** |
| Conductance (ml/min/mmHg) | | −1.1 | −2.1 | −1.3 | | −1.6 | | | NS |
| HCT (%) | | −1.7 | −3.5 | 3.1 | | −2.6 | | | * |
| Urine Flow (ml/hr) | | 0.4 | 0.9 | 0.6 | | 0.7 | | | NS |

Values are mean changes from control ± SED.
* $P < 0.05$,
** $P < 0.01$,
(*) $0.05 < P < 0.1$.

TABLE 14

MEAN RELAXATION OF DENUDED AORTIC RINGS EXPRESSED AS % OF KCL RESPONSE
GC-A mediated

| Group | Treatment | Mean relaxation SEM | Sig |
|---|---|---|---|
| | ANP | 66.5 ± 2.3 | |
| Group | TNPc | 55.0 ± 10.7 | NS |
| | TNPc I28P | 52.6 ± 5.0 | NS |
| | TNPc P32R | 66.4 ± 8.8 | NS |
| Group | TNPc Cha-10 | 64.2 ± 4.2 | NS |
| | TNPc R-18 | 0.5 ± 0.5 | *** |
| | TNPc A7 | 32.9 ± 4.5 | * |
| | TNPc K7 | 46.1 ± 13.5 | NS |
| | TNPc BTT | 62.1 ± 6.6 | NS |
| | TNPc DTT | 58.9 ± 6.7 | NS |
| Group 2c: | TNPc A7S6 | 43.1 ± 8.6 | NS |
| | TNPc K7S6 | 43.8 ± 4.3 | NS |
| | TNPc Z0 | 61.5 ± 5.5 | NS |
| | TNPc Nle | 61.0 ± 2.5 | NS |
| | TNPc diseleno | 60.5 ± 9.6 | NS |

Values are mean and SEM indicating group variance
Significance:
* $P < 0.05$,
** $P < 0.01$,
*** $P < 0.001$,
NS $P > 0.05$ compared to ANP

TABLE 15

STIMULATION BY VARIOUS PEPTIDES OF cGMP ACCUMULATION IN MDCK CELLS

| Peptide | EC50 (M) ± Standard Error | $-\text{Log}_{10}$ EC50 (pEC50) ± Standard Error | n |
|---|---|---|---|
| hBNP | 9.065e−010 ± 2.527e−010 | 9.165 ± 0.1039 | 10 |
| hANP | 1.645e−008 ± 1.053e−008 | 8.792 ± 0.2718 | 11 |
| rANP | 8.468e−009 ± 6.764e−009 | 8.761 ± 0.2936 | 7 |
| TNPc | 1.840e−007 ± 6.549e−008 | 6.928 ± 0.1122 | 12 |
| CHA10-TNPc | 1.444e−008 | 7.84 | 1 |
| P32R-TNPc | 9.907e−008 ± 8.144e−008 | 7.680 ± 0.5322 | 4 |
| N7D-TNPc | 2.624e−008 ± 3.100e−010 | 7.585 ± 0.005000 | 2 |
| R18-TNPc | 7.003e−007 ± 6.291e−007 | 6.777 ± 0.5812 | 3 |
| Nle-TNPc | 3.989e−007 ± 1.870e−007 | 6.497 ± 0.2017 | 3 |
| Sec2-TNPc | 6.386e−008 ± 3.503e−008 | 7.463 ± 0.4096 | 3 |
| K7-TNPc | 5.275e−008 ± 3.079e−008 | 7.443 ± 0.2700 | 3 |
| K7S6-TNPc | 5.239e−008 ± 2.817e−008 | 7.567 ± 0.4397 | 3 |
| A7-TNPc | 1.613e−007 ± 5.838e−008 | 6.867 ± 0.1915 | 3 |
| A7S6-TNPc | 1.692e−007 ± 6.979e−008 | 6.897 ± 0.2652 | 3 |
| I28P-TNPc | 1.188e−006 ± 6.075e−007 | 5.995 ± 0.2450 | 2 |
| Z0-TNPc | 9.706e−007 ± 8.613e−007 | 6.507 ± 0.4715 | 3 |
| DTT | 2.124e−008 ± 7.235e−009 | 7.723 ± 0.1425 | 3 |
| BTT | 7.062e−009 ± 1.513e−009 | 8.177 ± 0.1049 | 3 |
| DNP | 1.846e−006 ± 1.846e−006 | 8.080 ± 1.411 | 2 |
| PNP | 3.471e−007 ± 2.688e−007 | 6.660 ± 0.4500 | 2 |
| Lebetin | 2.675e−008 ± 1.027e−008 | 7.637 ± 0.1619 | 3 |

TABLE 16

STIMULATION BY VARIOUS PEPTIDES OF cGMP ACCUMULATION IN HELA CELLS

| Peptide | EC50 (M) | $-\text{Log}_{10}$EC50 (pEC50) ± Standard Error | n |
|---|---|---|---|
| hBNP | 1.47E−07 | −6.9197 ± 0.2966 | 3 |
| hANP | 4.81E−08 | −7.3287 ± 0.1564 | 3 |
| DNP | 3.92E−10 | −9.4177 ± 0.1651 | 3 |
| TNPc | 1.24E−01 | −3.9078 ± 2.7360 | 3 |
| TDT | 7.04E−08 | −7.208 ± 0.1468 | 3 |
| H12A-TDT | 2.29E−07 | −6.6483 ± 0.1815 | 3 |
| V20A-TDT | 4.55E−07 | −6.4183 ± 0.1660 | 3 |
| N22G-TDT | 3.14E−09 | −8.503 ± 0.2301 | 1 |
| H12R-TDT | 8.89E−09 | −8.051 ± 0.1789 | 1 |

What is claimed is:

1. An isolated protein having natriuretic activity in vertebrate animals including mammals, wherein the compound has a formula, comprising:

N-CORE-C wherein:
"N" is a peptide having a sequence of SEQ ID NO: 202,
"CORE" is a peptide having a sequence of SEQ ID NO: 203,
"C" is a peptide having a sequence of SEQ ID NO: 204, and
two C residues within SEQ ID NO: 203 are connected by a bridging bond, or a pharmaceutically acceptable salt thereof.

2. The compound according to claim 1, wherein Xaa at position 3 within SEQ ID NO:202 is selected from P or S.

3. The compound according to claim 1, wherein Xaa at position 7 within SEQ ID NO: 202 is selected from the group consisting of Q, D, or N, or modified D-forms of the foregoing thereof, L-N-methyl glutamine, D-α-methyl glutamine, L-N-methyl aspartic acid, and L-N-methyl asparagine.

4. The compound according to claim 1, wherein Xaa at position 4 within SEQ ID NO:203 is selected from G, F, L, H or R.

5. The compound according to claim 1, wherein Xaa at position 6 within SEQ ID NO:203 is selected from L, I or M.

6. The compound according to claim 1, wherein Xaa at position 10 within SEQ ID NO:203 is selected from G, S or N.

7. The compound according to claim 1, wherein Xaa at position 11 within SEQ ID NO:203 is selected from A, S or H.

8. The compound according to claim 1, wherein Xaa at position 12 within SEQ ID NO:203 is selected from S, V, M or Q.

9. The compound according to claim 1, wherein Xaa at position 14 within SEQ ID NO:203 is selected from G or N.

10. The compound according to claim 1, wherein Xaa at position 3 within SEQ ID NO:204 is selected from P or I.

11. The compound according to claim 1, wherein Xaa at position 4 within SEQ ID NO:204 is selected from V or M.

12. The compound according to claim 1, wherein Xaa at position 7 within SEQ ID NO:204 is selected from R or P.

13. The compound according to claim 1, wherein Xaa at position 7 within SEQ ID NO:204 is Pro.

14. The compound according to claim 1, wherein Xaa at position 7 within SEQ ID NO:202 is Gln.

15. The compound according to claim 1, wherein Xaa at position 4 within SEQ ID NO:204 is norleucine (Nle).

16. The compound according to claim 1, wherein one or both C residues within SEQ ID NO:203 are replaced by selenocysteine.

17. The compound according to claim 1, wherein the N-terminus is blocked by pGlu, Pro, Hyp or any N-acetylated residue.

18. The compound according to claim 1, wherein the C-terminus is blocked by amidation or cyclization.

19. A compound according to claim 1, wherein the formula further comprises the sequence set forth in SEQ ID NO:14 at its C-terminal end.

20. The compound according to claim 1, wherein the bridging bond that connects the two C residues within SEQ ID NO:203 is selected from the group consisting of a disulfide bond, a lanthionine bond, a diselenide or mixed sulfide-selenide bond, a methylene bond, a dimethylene bridge, a sulfide/methylene bond, an amide bond and an ester bond.

21. The compound according to claim 20, wherein the bridging bond is a disulfide bond.

22. An isolated protein having natriuretic activity in vertebrate animals including mammals, wherein the compound comprises any one of the sequences set forth in SEQ ID NO: 131 and 194-196.

23. A pharmaceutical composition comprising a compound according to claim 1, and a pharmaceutically acceptable carrier, excipient and/or diluent.

24. An isolated proteinaceous compound having at least one activity selected from vasodilatory natriuretic diuretic, renin-suppressing, bactericidal, weight-reducing or bone growth plate size-increasing activities, in vertebrate animals including mammals, wherein the compound comprises the sequence set forth in SEQ ID NO:193.

25. The compound according to claim 1, wherein the protein comprises the sequence set forth in SEQ ID NO:14 at its N terminus.

26. The compound according to claim 11, wherein Xaa at position 4 within SEQ ID NO:204 is valine (Val).

* * * * *